US010060932B2

(12) United States Patent
West et al.

(10) Patent No.: US 10,060,932 B2
(45) Date of Patent: Aug. 28, 2018

(54) BIOMARKERS OF AUTISM SPECTRUM DISORDER

(71) Applicant: STEMINA BIOMARKER DISCOVERY, Madison, WI (US)

(72) Inventors: Paul West, Arena, WI (US); Robert E. Burrier, Verona, WI (US); Laura Egnash, DeForest, WI (US); Alan Smith, Madison, WI (US); Preeti Bais, Unionville, CT (US)

(73) Assignee: Stemina Biomarker Discovery, Inc., Madison, WI (US)

( * ) Notice: Subject to any disclaimer, the term of this patent is extended or adjusted under 35 U.S.C. 154(b) by 0 days.

(21) Appl. No.: 14/903,717

(22) PCT Filed: Jul. 3, 2014

(86) PCT No.: PCT/US2014/045397
§ 371 (c)(1),
(2) Date: Jan. 8, 2016

(87) PCT Pub. No.: WO2015/006160
PCT Pub. Date: Jan. 15, 2015

(65) Prior Publication Data
US 2016/0169915 A1    Jun. 16, 2016

Related U.S. Application Data

(60) Provisional application No. 61/844,128, filed on Jul. 9, 2013, provisional application No. 61/996,835, filed on May 14, 2014.

(51) Int. Cl.
| | | |
|---|---|---|
| *G01N 33/50* | (2006.01) | |
| *G01N 33/48* | (2006.01) | |
| *G01N 33/483* | (2006.01) | |
| *G01N 33/49* | (2006.01) | |
| *G01N 33/52* | (2006.01) | |
| *G01N 33/561* | (2006.01) | |
| *A61K 49/00* | (2006.01) | |
| *A61B 5/00* | (2006.01) | |
| *G01N 33/68* | (2006.01) | |
| *G01N 30/72* | (2006.01) | |
| *G01N 33/487* | (2006.01) | |
| *G06F 19/00* | (2018.01) | |

(52) U.S. Cl.
CPC ......... *G01N 33/6896* (2013.01); *G01N 30/72* (2013.01); *G01N 33/487* (2013.01); *G01N 33/50* (2013.01); *G01N 2570/00* (2013.01); *G01N 2800/28* (2013.01); *G01N 2800/50* (2013.01); *G06F 19/707* (2013.01)

(58) Field of Classification Search
CPC ............ C12Q 2565/627; C12Q 1/6816; C12Q 1/6858; C12Q 1/6872; G01N 33/6848; G01N 33/92; G01N 2800/52; G01N 30/72; G01N 2560/00; G01N 2800/28; G01N 2800/2871; G01N 2800/50; G01N 33/487; G01N 33/50; G01N 33/5308; G01N 33/58; G01N 33/6812; G01N 33/6851; G01N 33/6896; Y10T 436/24; Y10T 436/25; Y10T 436/811; H01J 49/00; H01J 49/0027; G06K 9/00496; G06K 9/00543; G06F 19/22
See application file for complete search history.

(56) References Cited

U.S. PATENT DOCUMENTS

| | | | |
|---|---|---|---|
| 5,686,311 A * | 11/1997 | Shaw | ...................... G01N 33/70 436/811 |
| 6,365,593 B2 | 4/2002 | Rusche et al. | |
| 6,708,064 B2 * | 3/2004 | Rezai | ................. A61N 1/36082 607/2 |
| 7,329,489 B2 | 2/2008 | Kaddurah-Daouk et al. | |
| 7,433,787 B2 | 10/2008 | Barrett, Jr. et al. | |
| 7,550,258 B2 | 6/2009 | Kaddurah-Daouk et al. | |
| 7,553,616 B2 | 6/2009 | Kaddurah-Daouk et al. | |
| 7,561,975 B2 | 7/2009 | Young et al. | |
| 7,604,948 B2 * | 10/2009 | Amaral | ............ G01N 33/56972 435/7.1 |

(Continued)

FOREIGN PATENT DOCUMENTS

| | | | |
|---|---|---|---|
| WO | WO 2006/090185 A1 | 8/2006 | |
| WO | WO2006/121952 * | 11/2006 | ............... C12Q 1/00 |
| WO | WO 2006/121952 A2 | 11/2006 | |
| WO | WO 2011/139914 A1 | 11/2011 | |
| WO | WO 2014/043793 A1 | 3/2014 | |

OTHER PUBLICATIONS

Kappelman et al. Inflamm. Bowel Dis. 2008; 14: S6-S8.*
International Search Report and Written Opinion for PCT/US2014/045397; issued by the United States Patent and Trademark Office, dated Nov. 14, 2014; 16 pgs.
International Preliminary Report on Patentability for PCT/US2014/045397; issued by the International Bureau of WIPO, dated Jan. 21, 2016; 14 pgs.

(Continued)

*Primary Examiner* — Chang-Yu Wang
(74) *Attorney, Agent, or Firm* — Mueting, Raasch & Gebhardt, P.A.

(57) ABSTRACT

Methods for identifying metabolic signatures in blood plasma which are unique to autism are described herein. Samples are analyzed using multiple chromatographic-mass spectrometry-based techniques to orthogonally measure a broad range of small molecular weight metabolites differentially produced in autistic patient samples versus non-autistic control samples. These individual metabolites or a panel of such metabolites serve as metabolic signatures of autism. Such metabolic signatures are used in diagnostic methods to accurately identify individuals with autism spectrum disorder (ASD).

8 Claims, 13 Drawing Sheets

(56) References Cited

U.S. PATENT DOCUMENTS

| | | | |
|---|---|---|---|
| 7,623,927 B2* | 11/2009 | Rezai | A61N 1/36082 607/2 |
| 7,635,556 B2 | 12/2009 | Kaddurah-Daouk et al. | |
| 7,682,783 B2 | 3/2010 | Kaddurah-Daouk et al. | |
| 7,884,318 B2 | 2/2011 | Milgram et al. | |
| 7,910,301 B2 | 3/2011 | Kaddurah-Daouk et al. | |
| 7,947,453 B2 | 5/2011 | Kaddurah-Daouk et al. | |
| 7,949,475 B2 | 5/2011 | Barrett, Jr. et al. | |
| 8,131,473 B1 | 3/2012 | Coffin et al. | |
| 8,175,816 B2 | 5/2012 | Barrett, Jr. et al. | |
| 8,273,575 B2 | 9/2012 | Goodenowe | |
| 8,679,457 B2* | 3/2014 | Alexander | G01N 33/564 424/9.1 |
| 8,980,548 B2* | 3/2015 | Shuster | G01N 33/5091 435/6.1 |
| 9,176,113 B1* | 11/2015 | Geigenmuller | G01N 33/50 |
| 2002/0151939 A1* | 10/2002 | Rezai | A61N 1/36082 607/40 |
| 2003/0181954 A1* | 9/2003 | Rezai | A61N 1/36082 607/45 |
| 2004/0172091 A1* | 9/2004 | Rezai | A61N 1/36082 607/45 |
| 2007/0003922 A1* | 1/2007 | Amaral | G01N 33/56972 435/4 |
| 2008/0154332 A1* | 6/2008 | Rezai | A61N 1/36089 607/45 |
| 2011/0229883 A1 | 9/2011 | Spur et al. | |
| 2011/0312019 A1 | 12/2011 | West et al. | |
| 2012/0003158 A1* | 1/2012 | Alexander | G01N 33/564 424/9.2 |
| 2012/0157289 A1 | 7/2012 | Barr et al. | |
| 2012/0187289 A1 | 7/2012 | Barr | |
| 2012/0190055 A1 | 7/2012 | Cezar et al. | |
| 2013/0115649 A1* | 5/2013 | Shuster | G01N 33/5091 435/29 |
| 2013/0217647 A1* | 8/2013 | Shuster | G01N 33/57434 514/51 |
| 2014/0065132 A1* | 3/2014 | Hsiao | C07K 16/18 424/130.1 |
| 2014/0156573 A1* | 6/2014 | Szyperski | G06F 19/345 706/12 |
| 2014/0303228 A1* | 10/2014 | Lawton | G01N 33/6896 514/419 |
| 2014/0343865 A1* | 11/2014 | Brown | G01N 33/5011 702/19 |
| 2015/0293072 A1* | 10/2015 | Geigenmuller | G01N 33/50 250/282 |
| 2015/0294081 A1* | 10/2015 | Geigenmuller | G06F 19/345 506/12 |
| 2015/0301025 A1* | 10/2015 | Smith | G01N 33/5073 435/7.92 |
| 2015/0362510 A1* | 12/2015 | Gall | G06F 19/3431 435/7.92 |
| 2016/0091480 A1* | 3/2016 | Geigenmuller | G06F 19/345 506/12 |
| 2016/0091481 A1* | 3/2016 | Geigenmuller | G01N 33/50 250/282 |

OTHER PUBLICATIONS

Adams et al., "Nutritional and metabolic status of children with autism vs. neurotypical children, and the association with autism severity," *Nutr Metab (Lond)*, 2011; 8:34.

Aldred et al., "Plasma Amino Acid Levels in Children with Autism and Their Families," *J Autism Dev Disord*, Feb. 2003; 33(1):93-97.

Ashwood et al., "In search of cellular immunophenotypes in the blood of children with autism," *PLoS One*, 2011; 6(5):e19299.

Beaudet, Arthur L., "Preventable Forms of Autism?" *Science*, Oct. 19, 2012;338:342-343.

Belgard et al., "Population structure confounds autism genetic classifier," *Mol Psychiatry*, 2014; 19(4):405-7.

Beloborodova et al., "Effect of phenolic acids of microbial origin on production of reactive oxygen species in mitochondria and neutrophils," *J Biomed Sci*, 2012; 19:89.

Berg and Geschwind, "Autism genetics: searching for specificity and convergence," *Genome Biol*, 2012; 13:247.

Blumberg et al., "Changes in Prevalence of parent reported autism spectrum disorder in school aged U.S. children: 2007 to 2011-2012," *National Health Statistics Reports*, 2013, 65: 1-11.

Boccuto et al., "Prevalence of SHANK3 variants in patients with different subtypes of autism spectrum disorders," *Eur J Hum Genet*, 2013; 21(3):310-6. doi: 10.1038/ejhg.2012.175. Epub Aug. 15, 2012.

Boccuto et al., Decreased tryphtophan metabolism in patients with autism spectrum disorders. *Molecular Autism* 2013; 4:16.

Bogdanov et al., "Metabolomic profiling to develop blood biomarkers for Parkinson's disease," *Brain*, 2008; 131(Pt 2):389-96.

Bucan et al., "Genome-wide analyses of exonic copy number variants in a family-based study point to novel autism susceptibility genes," *PLoS Genet*, 2009; 5:e1000536.

Burrier et al., Abstract "A Metabolic Profile of Autism Spectrum Disorder from Autism Phenome Project Patient Plasma," Abstract No. 17556, The 13th Annual International Meeting for Autism Research (IMFAR), May 15-17, 2014, Atlanta, GA (abstracts embargoed until May 14, 2014), accessed at https://imfar.confex.com/imfar/2014/webprogram/Paper17556.html on Oct. 5, 2016.

Burrier et al., Poster "Mass Spectrometry Metabolomics Based Biomarkers for Detection of Autism Spectrum Disorder from Patient Blood Samples," Poster No. 175.093, The 13th Annual International Meeting for Autism Research (IMFAR), May 15-17, 2014, Atlanta, GA, presented May 17, 2016.

Centers for Disease Control and Prevention, "Prevalence of autism spectrum disorders—Autism and Developmental Disabilities Monitoring Network, 14 Sites, United States, 2008," *MMWR*, 2012; 61:1-9.

Centers for Disease Control and Prevention, "Prevalence of Autism Spectrum Disorder Among Children Aged 8 Years—Autism and Developmental Disabilities Monitoring Network, 11 sites, United States, 2010," *MMWR Surveill Summ*, Mar. 28, 2014; 63(2):1-21.

Dawson et al., "Randomized, controlled trial of an intervention for toddlers with autism: the early start Denver model," *Pediatrics*, 2010; 125(1):e17-23.

El-Ansary et al., "Plasma fatty acids as diagnostic markers in autistic patients from Saudi Arabia," *Lipids Health Dis*, 2011; 10:62.

Engel, Jeff, "Stemina's Autism Blood Test Shows Early Promise, Has Lots to Prove," Xconomy.com [online]. Nov. 10, 2014; retrieved from the Internet at http://www.xconomy.com/wisconsin/2014/11/10/steminas-autism-blood-test-shows-early-primise-has-lots-to-prove/ [retrieved online—Sep. 20, 2016] 3 pgs.

Evans et al., "Integrated, Nontargeted Ultrahigh Performance Liquid Chromatography/Electrospray Ionization Tandem Mass Spectrometry Platform for the Identification and Relative Quantification of the Small-Molecule Complement of Biological Systems," *Anal Chem*, 2009; 81:6656-6667.

Frye et al., Unique acyl-carnitine profiles are potential biomarkers for acquired mitochondrial disease in autism spectrum disorder, *Transl Psychiatry*, 2013; 3:e220.

Geier et al., "A Prospective Study of Transsulfuration Biomarkers in Autistic Disorders," *Neurochem Res*, 2009;34: 386-393.

Ghezzo et al., "Oxidative Stress and Erythrocyte Membrane Alterations in Children with Autism: Correlation with Clinical Features," *PLoS One*, 2013; 8:e66418.

Giuliva et al., "Mitochondrial Dysfunction in Autism," *JAMA*, 2010; 304(21):2389-2396.

Haury et al., "The influence of feature selection methods on accuracy, stability and interpretability of molecular signatures," *PLoS One*, 2011; 6:e28210.

Jaeken et al., "An Infantile Autistic Syndrome Characterised by the Presence of Succinylpurines in Body Fluids," *The Lancet*, Nov. 10, 1984; 2(8411):1058-1061.

James et al., "Metabolic biomarkers of increased oxidative stress and impared methylation capacity in children with autism," *Am J Clin Nutr*, 2004; 80:1611-1617.

(56) References Cited

OTHER PUBLICATIONS

James et al., "Efficacy of methylcobalamin and folinic acid treatment on glutathione redox status in children with autism," *Am J Clin Nutr*, 2009; 89:425-430.
Kleinstreuer et al., "Identifying developmental toxicity pathways for a subset of ToxCast Chemicals using human embryonic stem cells and metabolomics," *Toxicol Appl Pharmacol*, 2011; 257(1):111-121.
Kong et al., "Characteristics and predicitive value of blood transcriptome signature in males with autism spectrum disorders," *PloS One*, 2012; 7(12): e49475.
Lee and Tierney, "Hypothesis: The Role of Sterols in Autism Spectrum Disorder," *Autism Res Treat*, 2011; 653570:1-7.
Mew et al., "Clinical outcomes of neonatal onset proximal versus distal urea cycle disorders do not differ," *J Pediatr*, 2013; 162(2):324-9.
Momeni et al., "A novel blood-based biomarker for detection of autism spectrum disorders," *Transl Psychiatry*, 2012; 2:e91.
Mulle et al., "The gut microbiome: a new frontier in autism research," *Curr Psychiatry Rep*, 2013; 15(2):337.
Novarino et al., "Mutations in BCKD-kinase lead to a potentially treatable form of autism with epilepsy," *Science*, 2012; 338:394-397.
Payakachat et al., "Autism spectrum disorders: a review of measures for clinical, health services and cost-effectiveness applications," *Expert Rev Pharmacoecon Outcomes Res*, 2012;12:485-503.
Prentice et al., "The Furan Fatty Acid Metabolited CMPF is Eleveated in Diabetes and Induces β Cell Dysfunction," *Cell Metabolism*, 2014;19:653-666.
Quinones et al., "Metabolomics tools for identifying biomarkers for neuropsychiatric diseases," *Neurbiol of Disease*, 2009;35:165-176.
Rolf et al., "Serotonin and amino acid content in platelets of autistic children," *Acta Psychiatr Scand*, 1993; 87:312-316.
Rossignol and Frye, "A review of research trends in physiological abnormalities in autism spectrum disorders: immune dysregulation, inflammation, oxidative stress, mitochondrial dysfunction and environmental toxicant exposures," *Mol Psychiatry*, 2012; 17:389-401.
Safiulina et al., "Dehydroepiandrosterone inhibits complex I of the mitochondrial respiratory chain and is neurotoxic in vitro and in vivo at high concentrations," *Toxicol Sci*, 2006; 93:348-356.
Scribner et al., "Results of Analysis of the Fungicide Chlorothalonil, Its Degradation Products, and Other Selected Pesticides at 22 Surface-Water Sites in Five Southern States," *U.S. Geological Survey Toxic Substances Hydrology Program*, Open File Report 2006-1207; 2003-2004: 69 pgs.
Sing et al., "ROCR: visualizing classifier performance in R," *Bioinformatics*, 2005; 21:3940-3941.
Skafidas et al., "Predicting the diagnosis of autism spectrum disorder using gene pathway analysis," *Mol Psychiatry*, 2014; 19(4):504-10.
State and Sestan, "Neuroscience. The emerging biology of autism spectrum disorders," *Science*, 2012; 337:1301-1303.
Valerio et al., "Branched-chain amino acids, mitochondrial biogenesis, and healthspan: an evolutionary perspective," *Aging* (Albany NY), 2011; 3:464-478.
van den Berg et al., "Centering, scaling, and transformations: improving the biological information content of metabolomics data," *BMC Genomics*, 2006; 7:142.
Villas-Boas et al., "Mass Spectrometry in Metabolome Analysis," *Mass Spec Rev*, 2005;24:613-646.
Vinaixa et al., "A Guideline to Univariate Statistical Analysis for LC/MS-based Untargeted Metabolomics-Derived Data," *Metabolites*, 2012; 2:775-795.
Wang et al., "Common genetic variants on 5p14.1 associate with autism spectrum disorders," *Nature*, 2009; 459:528-533.
West et al., "Metabolomics as a Tool for Discovery of biomarkers of Autism Spectrum Disorder in the Blood Plasma of Children" *PLOS One*, Nov. 2014; 9(11): e112445: 13 pgs.

Yap et al., 2010, "Urinary metabolic phenotyping differentiates children with autism from their unaffected siblings and age-matched controls," *J Proteome Res*, 2010; 9:2996-3004.
Zablotsky et al., "Estimated Prevalence of Autism and Other Developmental Disabilities Following Questionnaire Changes in the 2014 National Health Interview Survey," *Natl Health Stat Reports*, Nov. 13, 2015; 87: 21 pgs.
Ming et al., "Metabolic perturbance in autism spectrum disorders: a metabolomics study," *J Proteome Res*, 2012; 11:5856-5862.
Extended European Search Report for Application No. 14822642.6 dated Dec. 9, 2016 (10 pages).
Communication issued in Europe for Application No. 14822642.6 dated Aug. 23, 2017 (7 pages).
Emond, Patrick et al., "GC-MS-based Urine Metabolic Profiling of Autism Spectrum Disorders", *Analytical and Bioanalytical Chemistry*, vol. 405, No. 15, Apr. 10, 2013, pp. 5291-5300.
Denoroy, Luc et al., "Ultra High Performance Liquid Chromatography as a Tool for the Discovery and the Analysis of Biomarkers of Diseases: A Review", *Journal of Chromatography B; Biomedical Sciences & Applications*, vol. 927, Dec. 22, 2012, pp. 37-53.
Jaisson, Stephane et al., "Quantification of Plasma Homocitrulline Using Hydrophilic Interaction Liquid Chromatography (HILIC) Coupled to Tandem Mass Spectrometry", Analytical and Bioanalytical Chemistry, vol. 402, No. 4, Dec. 12, 2011, pp. 1635-1641.
Al-Gandani et al., "Metabolic biomarkers related to oxidative stress and antioxidant status in Saudi Autistic Children," *Clin Biochem*, 2009; 42(10-11):1032-1040.
Arnold et al., "Plasma amino acids profiles in children with autism: potential risk of nutritional deficiencies," *J Autism Dev Disord*, Aug. 2003; 33(4):449-454.
Benjamini and Hochberg, "Controlling the false discovery rate: a practical and powerful approach to multiple testing," *J R Stat Soc Ser B*, 1995; 57:289-300.
Blaylock, "A possible central mechanism in autism spectrum disorders, part 2: Immunoexcitotoxicity," *Altern Ther Health Med*, 2009; 15(1):60-67.
Blaylock, "A possible central mechanism in autism spectrum disorders, part 3: the role of excitotoxin food additives and the synergistic effects of other environmental toxins," *Altern Ther Health Med*, 2009; 15(2):56-60.
Brown and Austin, "Autistic disorder and phospholipids: A review," *Prostaglandins Leukot Essent Fatty Acids*, 2011; 84 (1-2):25-30.
Bruce et al., "Evaluation of a protocol for metabolic profiling studies on human blood plasma by combined ultra-performance liquid chromatography/mass spectrometry: From extraction to data analysis," *Anal Biochem*; 2008; 372:237-249.
Corbett et al., "A proteomic study of autism from children with autism showing differential expression of apolipoprotiens and complement proteins," *Mol Psychiatry*, 2007; 12:292-306.
Cortes and Vapnik, "Support-vector networks," *Mach Learn*, 1995; 20:273-297.
Damodaran and Arumugam, "Urinary oxidative stress markers in children with autism," *Redox Rep*, 2011; 16:216-222.
Dunn et al., "Measuring the metabolome: current analytical technologies," *Analyst*, 2005; 130:606-625.
Fiehn et al., "Quality control for plant metabolomics: reporting MSI-compliant studies," *Plant J*, 2008; 53:691-704.
Fiehn and Kind, "Metabolite profiling in blood plasma," *Metabolomics: Methods and Protocols*. Weckwerth W (ed.), Humana Press, Totowa NJ, ISBN13: 978-1-59745-244-1. Methods in Molecular Biology, 2006; 358:3-18.
Ferreiro-Vera et al., "Comparison of sample preparation approaches for phospholipids profiling in human serum by liquid chromatography—tandem mass spectrometry," *J Chromatogr A*, 2012; 1240:21-28.
Ganz, "The lifetime distribution of the incremental societal costs of autism," *Arch Pediatr Adolesc Med*, 2007; 161:343-349.
Geier et al., "A prospective assessment of androgen levels in patients with autistic spectrum disorders: biochemical underpinnings and suggested therapies," *Neuro Endocrinol Lett*, 2007; 28(5):565-73.

(56) References Cited

OTHER PUBLICATIONS

Gika et al., "Hydrophilic interaction and reversed-phase ultra-performance liquid chromatography TOF-MS for metabonomic analysis of Zucker rat urine," *J Sep Sci*, 2008; 31:1598-1608.
Gross, "Accurate masses for structure confirmation," *J Am Soc Mass Spectrom*, 1994; 5:57.
Horai et al., "MassBank: a public repository for sharing mass spectral data for life sciences," *J Mass Spectrom*, 2010; 45:703-714.
Huguet et al., "The genetic landscapes of autism spectrum disorders," *Annu Rev Genomics Hum Genet*, 2013; 14:191-213.
James et al., "Cellular and mitochondrial glutathione redox imbalance in lymphoblastoid cells derived from children with autism," *FASEB J*, 2009; 23(8):2374-83.
Jiye et al., "Extraction and GC/MS analysis of the human blood plasma metabolome," *Anal Chem*, 2004; 77(24):8086-8094.
Kanehisa, "A database for post-genome analysis," *Trends Genet*, 1997; 13:375-376.
Kind et al., "A comprehensive urinary metabolomic approach for identifying kidney cancer," *Anal Biochem*, 2007; 363(2):185-95.
Kuhn, "Building predictive models in R using the caret package," *J Stat Softw*, 2008; 28:1-26.
Lawton et al., "Analysis of the adult human plasma metabolome," *Pharmacogenomics*, 2008; 9(4):383-397.
Lombard J, "Autism: a mitochondrial disorder?" *Medical Hypotheses* 1998; 50:497-500.
Manzi et al., "Autism and metabolic diseases," *J Child Neurol.*, 2008; 23:307-314.
Marazziti et al., "Psychiatric disorders and mitochondrial dysfunctions," *Eur Rev Med Pharmacol Sci*, 2012; 16:270-275.
Moreno-Fuenmayor et al., "Plasma excitatory amino acids in autism," *Invest Clin*, 1996; 37:113-128.
Müller and Kölker, "Reduction of lysine intake while avoiding malnutrition—major goals and major problems in dietary treatment of glutaryl-CoA dehydrogenase deficiency," *J Inherit Metab Dis*, 2004; 27:903-910.
Napolioni et al., "The mitochondrial aspartate/glutamate carrier AGC1 and calcium homeostasis: physiological links and abnormalities in autism," *Mol Neurobiol*, 2011; 44:83-92.
Orchard et al., "Five years of progress in the Standardization of Proteomics Data 4th Annual Spring Workshop of the HUPO-Proteomics Standards Initiative Apr. 23-25, 2007 Ecole Nationale Supérieure (ENS), Lyon, France," *Proteomics*, 2007; 7:3436-3440.
Palmieri, "The mitochondrial transporter family (SLC25): physiological and pathological implications," *Pflugers Arch*, 2004; 447:689-709.
Pastural et al., "Novel plasma phospholipid biomarkers of autism: mitochondrial dysfunction as a putative causative mechanism," *Prostaglandins, Leukotrienes and Fatty Acids*, 2009; 81:253-264.
Prince and Marcotte, "Chromatographic alignment of ESI-LC-MS proteomics data sets by ordered bijective interpolated warping," *Anal Chem*, 2006; 78:6140-6152.
Rochfort, S: Metabolomics Reviewed: A New "Omics" Platform Technology for Systems Biology and Implications for Natural Products Research, *J Nat Prod*, 2005; 68:1813-1820.
Serkova et al., "NMR-based metabolomics: translational application and treatment of cancer," *Curr Opin Mol Ther*, 2007; 9(6):572-85.
Shinohe et al., "Increased serum levels of glutamate in adult patients with autism," *Prog Neuropsychopharmacol Biol Psychiatry*, 2006; 30:1472-1477.
Smith et al., "XCMS: processing mass spectrometry data for metabolite profiling using nonlinear peak alignment, matching, and identification," *Anal Chem*, 2006; 78:779-787.
Smith et al., "METLIN: a metabolite mass spectral database," *Ther Drug Monit*, 2005; 27:747-751.
Strous et al., "Lowered DHEA-S Plasma Levels in Adult Individuals with autistic disorder," *Eur Neuropsychopharmacol*, 2005; 15(3):305-309.
Thompson, "Autism research and services for young children: history, progress and challenges," *J Appl Res Intellect Disabil*, 2013; 26:81-107.
Tordjman et al., "Plasma androgens in autism," *J Autism Dev Disord*, 1995; 25(3):295-304.
Walsh et al., "In search of biomarkers for autism: scientific, social and ethical challenges," *Nat Rev Neurosci.*, 2011; 12(10):603-12.
Whiteley et al., "Spot urinary creatinine excretion in pervasive developmental disorders," *Pediatr Int*, 2006; 48:292-297.
Zoroglu et al., "Increased oxidative stress and altered activities of erythrocyte free radical scavenging enzymes in autism," *Eur Arch Psychiatry Clin Neurosci*, 2004; 254:143-147.

\* cited by examiner

Figure 13

Autism Feature Categories

Lysine Degradation
- *Homocitrulline*
- *Glutaric acid*
- Saccharopine
- *5-Aminovaleric acid*

Glycolysis
- Lactate
- *Succinate*
- *Citrate*
- Isocitrate

Sterols
- DHEAS
- DHA
- Androsterone sulfate
- 27-Norcholesterol
- Mevalanolactone

Phospholipds
- Lyso PE
- PE
- Long chain Fas
- LysoPC

Urea Cycle
- *Aspartate*
- Glutamate
- Acetylornithine

Serine Metabolsim
- *Serine*
- Homocysteic acid
- Valine
- Cystine
- Hydroxyacetone
- Phosphohydroxypyruvate

Branched Chain Ketoacid Dehyd Kinase (BCKDK)
- *Valine*
- *Isoleucine*
- Ketoleucine

Trp/Serotonin Metabolism
- *Indole-3-lactate*

Thymine Degradation
- *3-Amino isobutyrate*

BIOMARKERS OF AUTISM SPECTRUM DISORDER

CONTINUING APPLICATION DATA

This application is the § 371 U.S. National Stage of International Application No. PCT/US2014/045397, filed 3 Jul. 2014, which claims the benefit of U.S. Provisional Application Ser. No. 61/844,128, filed Jul. 9, 2013, and U.S. Provisional Application Ser. No. 61/996,835, filed May 14, 2014, each of which is incorporated by reference herein.

BACKGROUND

Autism spectrum disorder (ASD) is a lifelong neurodevelopmental disorder characterized by social deficits, impaired verbal and nonverbal communication and repetitive movements or circumscribed interests (see, for example, American Psychiatric Association (2013) Desk Reference to the Diagnostic Criteria from DSM-5, 5th ed. Washington, D.C.; American Psychiatric Association). About 1 in 68 children are identified with autism spectrum disorder according to estimates from CDC's Autism and Developmental Disabilities Monitoring (ADDM) Network (Centers for Disease Control and Prevention, 2014, *MMWR Surveill Summn;* 63:1-21). The current process for a clinical diagnosis includes establishing a developmental history and assessments of behavioral characteristics such as speech, language, intellectual abilities, and educational or vocational attainment. Patients can be reliably diagnosed through behavioral testing at age 2 years. However, for a variety of reasons, the average age of diagnosis is 4.5 years. It is increasingly recognized that detection of ASD at the earliest age possible age is important for initiating optimally effective intervention and results in better patient and family outcomes (Payakachat et al., 2012, *Expert Rev Pharnmacoecon Outcomes Res;* 12:485-503; and Thompson, 2013, *J Appl Res Intellect Disabil;* 26:81-107). Establishing personalized therapy for children with ASD at the earliest age possible improves outcomes including a higher level of cognitive and social function and improved communication as well as decreased financial and emotional burden on families (Dawson et al., 2010, *Pediatrics;* 125:e17-23; and Ganz, 2007, *Arch Pediatr Adolesc Med;* 161:343-349). Thus, the development of a biologically-based blood test to aid in the assessment of risk for a diagnosis of ASD at an early age would facilitate implementing intensive behavioral therapy at the earliest age possible and would be beneficial to patients, families and medical providers.

SUMMARY OF THE INVENTION

The present invention includes a method for identifying a metabolomic signature characteristic for autism in a human, the method including:

a) assaying a collection of biosamples isolated from autistic subjects for one or a plurality of small molecule metabolites by gas chromatography mass spectrometry (GCMS);

b) assaying a collection of biosamples isolated from non-autistic control subjects for one or a plurality of small molecule metabolites by GCMS;

c) identifying one or a plurality of small molecule metabolites assayed by GCMS that are differentially produced in autistic subjects as compared to non-autistic control subjects;

d) assaying the collection of biosamples isolated from autistic subjects for one or a plurality of small molecule metabolites by one or more untargeted liquid chromatography-high resolution mass spectrometry methodologies (LC/HRMS);

e) assaying the collection of biosamples isolated from non-autistic control subjects for one or a plurality of small molecule metabolites by one or more untargeted LC/HRMS methodologies;

f) identifying one or a plurality of small molecule metabolites assayed by the one or more untargeted LC/HRMS methodologies that are differentially produced in autistic subjects as compared to non-autistic control subjects;

g) combining the plurality of small molecule metabolites identified by step c) and step f) to form a training set of small molecule metabolites; and h) selecting from the training set a subset of small molecule metabolites with a statistically significant abundance difference in the collection of biosamples isolated form autistic patients as compared to the collection of biosamples isolated from control non-autistic control subjects;

wherein the subset of small molecules of step h) includes a metabolomic signature for autism in a human.

In some aspects of the methods of the present invention, assaying biosamples by one or more untargeted liquid chromatography-high resolution mass spectrometry methodologies (LC/HRMS) includes assaying the biosamples by C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg).

The present invention includes a method for identifying a metabolomic signature characteristic for autism in a human, the method including:

assaying a collection of biosamples isolated from autistic subjects for one or a plurality of small molecule metabolites by two or more methodologies selected from gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg);

assaying a collection of biosamples isolated from non-autistic control subjects for one or a plurality of small molecule metabolites by the same two or more methodologies selected from GC-MS, C8pos, C8neg, HILICpos, and/or HILICneg; and identifying for each of the two or methodologies one or a plurality of small molecule metabolites that are differentially produced in autistic subjects as compared to non-autistic control subjects;

combining the plurality of small molecule metabolites that are differentially produced in autistic subjects as compared to non-autistic control subjects identified by each of the two or more methodologies to form a training set of small molecule metabolites; and selecting from the training set a subset of small molecule metabolites with a statistically significant abundance difference in the biosamples isolated from autistic subjects as compared to the biosamples isolated from control non-autistic control subjects;

wherein the subset of small molecules with a statistically significant abundance difference in the biosamples isolated from autistic subjects as compared to the biosamples isolated from control non-autistic control subjects includes a metabolomic signature for autism.

In some aspects, biosamples are assayed by three or more methodologies selected from gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg).

In some aspects, biosamples are assayed by four or more methodologies selected from gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg).

In some aspects, biosamples are assayed by gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and hydrophilic interaction liquid chromatography coupled to electrospray ionization in negative ion polarity (HILICneg).

The present invention includes a method for identifying a metabolomic signature characteristic for autism in a human, the method including:

a) assaying a collection of biosamples isolated from autistic subjects for one or a plurality of small molecule metabolites by gas chromatography mass spectrometry (GCMS);

b) assaying a collection of biosamples isolated from non-autistic control subjects for one or a plurality of small molecule metabolites by GCMS;

c) identifying one or a plurality of small molecule metabolites assayed by GCMS that are differentially produced in autistic subjects as compared to non-autistic control subjects;

d) assaying the collection of biosamples isolated from autistic subjects for one or a plurality of small molecule metabolites by C8 liquid chromatography coupled to electrospray ionization in positive ion polarity (C8pos);

e) assaying the collection of biosamples isolated from non-autistic control subjects for one or a plurality of small molecule metabolites by C8pos;

f) identifying one or a plurality of small molecule metabolites assayed by C8pos that are differentially produced in autistic subjects as compared to non-autistic control subjects;

g) assaying the collection of biosamples isolated from autistic subjects for one or a plurality of small molecule metabolites by C8 liquid chromatography coupled to electrospray ionization in negative ion polarity (C8neg);

h) assaying the collection of biosamples isolated from non-autistic control subjects for one or a plurality of small molecule metabolites by C8neg;

i) identifying one or a plurality of small molecule metabolites assayed by C8neg that are differentially produced in autistic subjects as compared to non-autistic control subjects;

j) assaying the collection of biosamples isolated from autistic subjects for one or a plurality of small molecule metabolites by hydrophilic interaction liquid chromatography coupled to electrospray ionization in positive ion polarity (HILICpos);

k) assaying the collection of biosamples isolated from non-autistic control subjects for one or a plurality of small molecule metabolites by HILICpos;

l) identifying one or a plurality of small molecule metabolites assayed by HILICpos that are differentially produced in autistic subjects as compared to non-autistic control subjects;

m) assaying the collection of biosamples isolated from autistic subjects for one or a plurality of small molecule metabolites by hydrophilic interaction liquid chromatography coupled to electrospray ionization in negative ion polarity (HILICneg);

n) assaying the collection of biosamples isolated from non-autistic control subjects for one or a plurality of small molecule metabolites by HILICneg;

o) identifying one or a plurality of small molecule metabolites assayed by HILICneg that are differentially produced in autistic subjects as compared to non-autistic control subjects;

p) combining the plurality of small molecule metabolites identified by step c), step f), step I), step l), and step o) to form a training set of small molecule metabolites; and q) selecting from the training set a subset of small molecule metabolites with a statistically significant abundance difference in the collection of biosamples isolated form autistic patients as compared to the collection of biosamples isolated from control non-autistic control subjects;

wherein the subset of small molecules of step q) includes a metabolomic signature for autism in a human.

In some aspects, the training set a subset of small molecule metabolites with a statistically significant abundance difference in the collection of biosamples isolated from autistic patients as compared to the collection of biosamples isolated from control non-autistic control subjects are selecting by univariate analysis, multivariate analysis, machine learning analysis, support vector machine analysis (SVM), and/or partial least squares analysis (PLS).

With any of the methods of the present invention, a small molecule metabolite may have a molecular weight of from about 10 Daltons to about 3000 Daltons.

With any of the methods of the present invention, a biosample may be cerebrospinal fluid, brain tissue, amniotic fluid, blood, serum, plasma, amniotic fluid, or urine.

With any of the methods of the present invention, the biosample may be plasma.

With any of the methods of the present invention, the metabolomic signature for autism includes one or more of the 179 metabolites listed in Table 6.

With any of the methods of the present invention, the metabolomic signature for autism includes at least 40 of the metabolites listed in Table 6.

With any of the methods of the present invention, the metabolomic signature for autism includes about 80 to about 160 of the metabolites listed in Table 6.

With any of the methods of the present invention, the metabolomic signature for autism includes any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one metabolites of homocitrulline, 2-hydroxyvaleric acid, cystine, aspartic acid, isoleucine, creatinine, serine, 4-hydroxyphenyllactic acid, citric acid, glutamic acid, lactic acid, DHEA sulfate, glutaric acid, 5-hydroxynorvaline, heptadecanoic acid, 5-aminovaleric acid lactam, succinic acid, myristic acid, 2-hydroxyvaleric acid, methylhexadecanoic acid, and/or 3-aminoisobutyric acid.

With any of the methods of the present invention, the metabolomic signature for autism includes any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one or more metabolites, any twenty two or more metabolites, any twenty three or more metabolites, any twenty four or more metabolites, any twenty five or more metabolites, and/or twenty six metabolites of 2-aminooctanoic acid, acesulfame, ADMA, choline, CMPF, cysteine, cystinc, DHEA sulfate (DHEAS), glycine, glycocholic acid, hypoxanthine, indoleacrylic acid, indoxyl sulfate, LysoPC (16:1(9Z)), LysoPE(0:0/18:1(9Z)), LysoPE(22:6(4Z,7Z, 10Z,13Z,16Z19Z)/0:0), LysoPE(22:6(4Z,7Z,10Z,13Z,16Z, 19Z)/0:0), methionine, p-cresol sulfate, phenylalanine, phenyllactic acid, proline, serotonin, tryptophan, uric acid, and/or valine.

With any of the methods of the present invention, the metabolomic signature for autism includes any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one or more metabolites, any twenty two or more metabolites, any twenty three or more metabolites, any twenty four or more metabolites, any twenty five or more metabolites, any twenty six metabolites or more metabolites, any twenty seven metabolites or more metabolites, any twenty eight metabolites or more metabolites, and/or twenty nine metabolites of homocitrulline, glutaric acid, saccharopine, 5-aminovaleric acid, lactate, succinate, isocitrate, DHEAS, DHA, androsterone sulfate, 27-norcholesterol, Lyso PE, PE, long chain Fas, LysoPC, aspartate, glutamate, acetylornithine, valine, isoleucine, ketoleucine, serine, homocysteic acid, valine, cystine, hydroxyacetone, phosphohydroxypyruvate, indole-3-lactate, and/or 3-amino isobutyrate.

With any of the methods of the present invention, a metabolic signature for autism may demonstrate decreased homocitrulline, increased glutaric acid, increased saccharopine, increased 5-aminovaleric acid, increased lactate, increased succinate, decreased isocitrate, increased DHEAS, increased DHA, increased androsterone sulfate, increased 27-norcholesterol, decreased Lyso PE, decreased PE, decreased long chain Fas, decreased LysoPC, increased asparate, increased glutamate, increased acetylornithine, decreased valine, decreased isoleucine, increased ketoleucine, increased serine, decreased homocysteic acid, decreased valine, decreased cystine, increased hydroxyacetone, increased phosphohydroxypyruvate, decreased indole-3-lactate, and/or increased 3-amino isobutyrate.

With any of the methods of the present invention, the metabolomic signature for autism includes homocitrulline.

With any of the methods of the present invention, the metabolomic signature for autism includes decreased homocitrulline.

Any of the methods of the present invention may further include a step of determining a chemical identity for one or a plurality of the cellular metabolites. In some aspects, the chemical identity of one or a plurality of the cellular metabolites is determined using molecular exact mass for the metabolite or mass spectrometry fragmentation patterns of the metabolites.

Any of the methods of the present invention may further include determining a ratio of two or more small molecule metabolites.

Any of the methods of the present invention may further include a combination assessment of the relative abundance of two or more small molecule metabolites.

With any of the methods of the present invention, the biosamples from autistic subjects autistic subjects are obtained from a phenotypic subpopulation of autism subjects and wherein the metabolomic signature for autism includes a metabolomic signature for the phenotypic subpopulation of autism subjects. In some aspects the phenotypic subpopulation of autism subjects includes low function autism (LFA) or high function autism (HFA).

The present invention includes a metabolomic signature for autism produced according to a method as described above.

The present invention includes a metabolomic signature for autism, the metabolomic signature including any one or more features, two or more features, three or more features, four or more features, five or more features, six or more features, seven or more features, eight or more features, nine or more features, ten or more features, eleven or more features, twelve or more features, thirteen or more features, fourteen or more features, fifteen or more features, sixteen or more features, seventeen or more features, eighteen or more features, nineteen or more features, twenty or more features, or twenty one features of homocitrulline, 2-hydroxyvaleric acid, cystine, aspartic acid, isoleucine, creatinine, serine, 4-hydroxyphenyllactic acid, citric acid, glutamic acid, lactic acid, DHEA sulfate, glutaric acid, 5-hydroxynorvaline, heptadecanoic acid, 5-aminovaleric acid lactam, succinic acid, myristic acid, 2-hydroxyvaleric acid, methylhexadecanoic acid, and/or 3-aminoisobutyric acid.

The present invention includes a metabolomic signature for autism, the metabolomic signature including any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one or more metabolites, any twenty two or more metabolites, any twenty three or more metabolites, any twenty four or more metabolites, any twenty five or more metabolites, and/or twenty six metabolites of 2-aminooctanoic acid, acesulfame, ADMA, choline, CMPF, cysteine, cystine, DHEA sulfate (DHEAS), glycine, glycocholic acid, hypoxanthine, indoleacrylic acid, indoxyl sulfate, LysoPC (16:1(9Z)), LysoPE(0:0/18:1(9Z)), LysoPE(22:6(4Z,7Z, 10Z,13Z,16Z,19Z)/0:0), LysoPE(22:6(4Z,7Z,10Z,13Z,16Z, 19Z)/0:0), methionine, p-cresol sulfate, phenylalanine, phenyllactic acid, proline, serotonin, tryptophan, uric acid, and/or valine.

The present invention includes a metabolomic signature for autism, the metabolomic signature including one or more of the features set forth in Table 6.

The present invention includes a metabolomic signature for autism including at least 40 of the metabolites listed in Table 6.

The present invention includes a metabolomic signature for autism including about 80 to about 160 of the metabolites listed in Table 6.

In some aspects of a metabolomic signature for autism of the present invention, a signature may include homocitrulline. In some aspects of the metabolic signature, homocitrulline is decreased.

In some aspects of a metabolomic signature for autism of the present invention, the metabolic signature is indicative of high functioning autism (HFA) and/or low functioning autism (LFA).

In some aspects of a metabolomic signature for autism of the present invention, the metabolomic signature for autism includes any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one or more metabolites, any twenty two or more metabolites, any twenty three or more metabolites, any twenty four or more metabolites, any twenty five or more metabolites, any twenty six metabolites or more metabolites, any twenty seven metabolites or more metabolites, any twenty eight metabolites or more metabolites, and/or twenty nine metabolites of homocitrulline, glutaric acid, saccharopine, 5-aminovaleric acid, lactate, succinate, isocitrate, DHEAS, DHA, androsterone sulfate, 27-norcholesterol, Lyso PE, PE, long chain Fas, LysoPC, asparate, glutamate, acetylornithine, valine, isoleucine, ketoleucine, serine, homocysteic acid, valine, cystine, hydroxyacetone, phosphohydroxypyruvate, indole-3-lactate, and/or 3-amino isobutyrate.

In some aspects of a metabolomic signature for autism of the present invention, the metabolomic signature for autism includes decreased homocitrulline, increased glutaric acid, increased saccharopine, increased 5-aminovaleric acid, increased lactate, increased succinate, decreased isocitrate, increased DHEAS, increased DHA, increased androsterone sulfate, increased 27-norcholesterol, decreased Lyso PE, decreased PE, decreased long chain Fas, decreased LysoPC, increased asparate, increased glutamate, increased acetylornithine, decreased valine, decreased isoleucine, increased ketoleucine, increased serine, decreased homocysteic acid, decreased valine, decreased cystine, increased hydroxyacetone, increased phosphohydroxypyruvate, decreased indole-3-lactate, and/or increased 3-amino isobutyrate.

The present invention includes a method for assessing a subjects risk for autism, the method including:

assaying a biosample from the subject for one or a plurality of small molecule metabolites by one or more methodologies selected from gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg);

quantifying the amount of one or more of the 179 small molecule metabolites listed in Table 6;

wherein a statistically significant abundance difference as compared to non-autistic controls in one or more of the 179 small molecule metabolites listed in Table 6 indicates an increased risk of autism.

The present invention includes a method for assessing a subjects risk for autism, the method including assaying a biosample from the subject for one or a plurality of small molecule metabolites; and quantifying the amount of one or more of the 179 small molecule metabolites listed in Table 6; wherein a statistically significant abundance difference as compared to non-autistic controls in one or more of the 179 small molecule metabolites listed in Table 6 indicates an increased risk of autism. In some aspects, the biosample is assayed by one or more methodologies selected from gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg).

In some aspects of a method for assessing a subjects risk for autism of the present invention, a statistically significant abundance difference as compared to non-autistic controls of at least 40 of the metabolites listed in Table 6 indicates an increased risk of autism.

In some aspects of a method for assessing a subjects risk for autism of the present invention, a statistically significant abundance difference as compared to non-autistic controls of about 80 to about 160 of the metabolites listed in Table 6 indicates an increased risk of autism.

In some aspects of a method for assessing a subjects risk for autism of the present invention, a statistically significant abundance difference as compared to non-autistic controls of any one or more any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one metabolites of homocitrulline, 2-hydroxyvaleric acid, cystine, aspartic acid, isoleucine, creatinine, serine, 4-hydroxyphenyllactic acid, citric acid, glutamic acid, lactic acid, DHEA sulfate, glutaric acid, 5-hydroxynorvaline, heptadecanoic acid, 5-aminovaleric acid lactam, succinic acid, myristic acid, 2-hydroxyvaleric acid, methylhexadecanoic acid, and/or 3-aminoisobutyric acid indicates an increased risk of autism.

In some aspects of a method for assessing a subjects risk for autism of the present invention, a statistically significant abundance difference as compared to non-autistic controls of any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one or more metabolites, any twenty two or more metabolites, any twenty three or more metabolites, any twenty four or more metabolites, any twenty five or more metabolites, and/or twenty six metabolites of 2-aminooctanoic acid, acesulfarne, ADMA, choline, CMPF, cysteine, cystine, DHEA sulfate (DHEAS), glycine, glycocholic acid, hypoxanthine, indoleacrylic acid, indoxyl sulfate, LysoPC(16:1(9Z)), LysoPE(0:0/18:1 (9Z)), LysoPE (22:6(4Z,7Z,10Z,13Z,16Z,19Z)/0:0), LysoPE(22:6(4Z,7Z, 10Z,13Z,16Z,19Z)/0:0), methionine, p-cresol sulfate, phenylalanine, phenyllactic acid, proline, serotonin, tryptophan, uric acid, and/or valine indicates an increased risk of autism.

In some aspects of a method for assessing a subjects risk for autism of the present invention, a statistically significant abundance difference as compared to non-autistic controls of any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one or more metabolites, any twenty two or more metabolites, any twenty three or more metabolites, any twenty four or more metabolites, any twenty five or more metabolites, any twenty six metabolites or more metabolites, any twenty seven metabolites or more metabolites, any twenty eight metabolites or more metabolites, and/or twenty nine metabolites of homocitrulline, glutaric acid, saccharopine, 5-aminovaleric acid, lactate, succinate, isocitrate, DHEAS, DHA, androsterone sulfate, 27-norcholesterol, Lyso PE, PE, long chain Fas, LysoPC, asparate, glutamate, acetylornithine, valine, isoleucine, ketoleucine, serine, homocysteic acid, valine, cystine, hydroxyacetone, phosphohydroxypyruvate, indole-3-lactate, and/or 3-amino isobutyrate indicates an increased risk of autism.

In some aspects of a method for assessing a subjects risk for autism of the present invention, decreased homocitrulline, increased glutaric acid, increased saccharopine, increased 5-aminovaleric acid, increased lactate, increased succinate, decreased isocitrate, increased DHEAS, increased DHA, increased androsterone sulfate, increased 27-norcholesterol, decreased Lyso PE, decreased PE, decreased long chain Fas, decreased LysoPC, increased asparate, increased glutamate, increased acetylornithine, decreased valine, decreased isoleucine, increased ketoleucine, increased serine, decreased homocysteic acid, decreased valine, decreased cystine, increased hydroxyacetone, increased phosphohydroxypyruvate, decreased indole-3-lactate, and/or increased 3-amino isobutyrate is indicative of autism.

In some aspects of a method for assessing a subjects risk for autism of the present invention, a statistically significant abundance difference as compared to non-autistic controls of homocitrulline indicates an increased risk of autism.

In some aspects of a method for assessing a subjects risk for autism of the present invention, the method further includes determining a ratio of two or more small molecule metabolites.

In some aspects of a method for assessing a subjects risk for autism of the present invention, the method further includes a combination assessment of the relative abundance of two or more small molecule metabolites.

In some aspects of a method for assessing a subjects risk for autism of the present invention, a biosample may be cerebrospinal fluid, brain tissue, amniotic fluid, blood, serum, plasma, amniotic fluid, or urine.

In some aspects of a method for assessing a subjects risk for autism of the present invention, a biosample may be plasma.

In some aspects of a method for assessing a subjects risk for autism of the present invention, the subject is less than two years of age.

In some aspects of a method for assessing a subjects risk for autism of the present invention, the metabolic signature is indicative of a phenotypic subpopulation of autism subjects.

In some aspects of a method for assessing a subjects risk for autism of the present invention, the metabolic signature is indicative of high functioning autism (HFA) and/or low functioning autism (LFA).

The terms used in the specification generally have their ordinary meanings in the art, within the context of the invention, and in the specific context where each term is used. Some terms have been more specifically defined below to provide additional guidance to the practitioner regarding the description of the invention.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 13. Autism Feature Categories. Arrow indicates direction of fold change. Italicized type indicates confirmed molecules. Bold type indicates mitochondrial connection.

DETAILED DESCRIPTION OF ILLUSTRATIVE EMBODIMENTS

Figure 1:
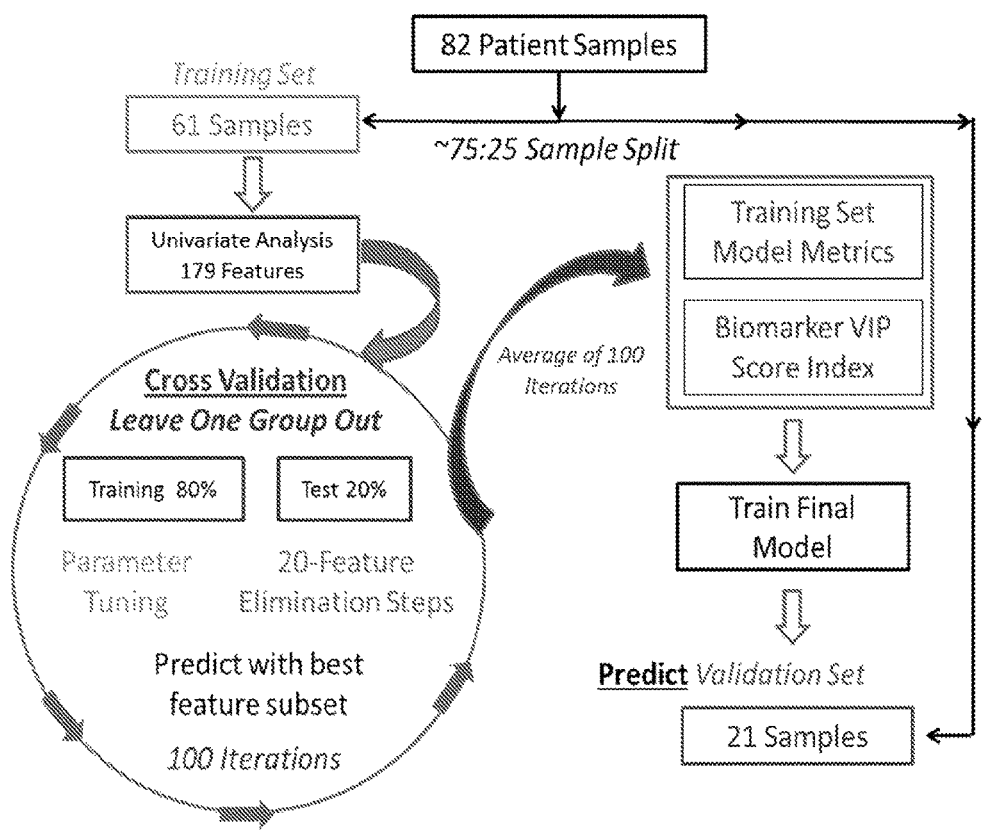
FIG. 1. Classification modeling process. A three-layer nested cross-validation approach was applied using both PLS-DA and SVM modeling methods to determine significant features capable of classifying children with ASD from TD children. The 179 features of the training set were analyzed using a leave-one-group-out cross-validation loop as described. The results from this cross-validation process were used to estimate model performance and create a robust feature VIP score index to rank the ASD versus TD classification importance of each of the 179 features. These feature ranks were used to evaluate the performance of the molecular signature using an independent validation set.

The present invention includes methods for the identification of metabolic biomarkers characteristic of autism spectrum disorder (ASD) in humans. A metabolomics-based approach was used to identify a plurality of metabolic biomarkers that are differentially produced in autistic patients relative to typically developing individuals. Samples are analyzed using multiple high resolution mass spectrometry-based techniques to orthogonally measure a broad range of small molecular weight metabolites differentially produced in autistic patient samples versus non-autistic control samples. These individual metabolites or a panel of such metabolites serve as metabolic signatures of autism. Such metabolic signatures are used in diagnostic methods to accurately identify individuals with autism spectrum disorder (ASD).

As there is not one universal chromatographic mass spectrometric technique capable of detecting all of the metabolites in a biosample, with the present invention multiple high resolution mass spectrometry-based techniques are used, each independently measuring a broad range of small molecular weight metabolites differentially produced in autistic patient samples versus non-autistic control samples. Any of a number of known high resolution mass spectrometry-based techniques may be used to independently measure a broad range of small molecular weight metabolites differentially produced in autistic patient samples versus non-autistic control samples. For example, samples may be assayed using at least two, at least three, at least four, at least five, or at least six different high resolution mass spectrometry-based techniques.

In some aspect, any combination of one or more gas chromatography-mass spectrometry (GC-MS) methodologies and/or one or more liquid chromatography-high resolution mass spectrometry (LC-HRMS) methodologies may be used. In some aspects, a GC-MS method may be targeted. In some aspects, a LC-HRMS method may be untargeted. Subsequently, in some embodiments, tandem mass spectrometry (MS-MS) methods may be employed for the structural confirmation of metabolites. LC-HRMS methodologies may include C8 chromatography and/or Hydrophilic Interaction Liquid Chromatography (HILIC) chromatography. Either of C8 chromatography or HILIC chromatography may be coupled to electrospray ionization in both positive and negative ion polarities, resulting in multiple data acquisitions per sample.

In some embodiments, samples may be analyzed using five different chromatographic-mass spectrometry-based methods, GC-MS and four untargeted LC-HRMS methods. The four untargeted LC-HRMS methods may include C8 chromatography and HILIC chromatography, both coupled to electrospray ionization in both positive and negative ion polarities, resulting in 4 separate data acquisitions per sample, to orthogonally measure a broad range of metabolites in blood plasma. Univariate, multivariate, and machine learning methods may be used to develop models in which the importance of features used for the determination of biomarkers to distinguish samples from the children with ASD from samples from the TD children were ranked. A training set of samples may be used for univariate and multivariate analysis to build the classification models. Additional samples may be used as an independent validation test set.

Statistical models were created using different combinations of the significant mass features. In one embodiment, these models generated a set of 179 features that were altered in abundance in the ASD samples and a subset of these features could properly classify the ASD and TD samples in the independent validation set with a maximum accuracy of 81%.

As used herein, a "training set" is a set of data used in various areas of information science to discover potentially predictive relationships. Training sets are used in artificial intelligence, machine learning, genetic programming, intelligent systems, and statistics. In all these fields, a training set has much the same role and is often used in conjunction with a test set.

As used herein, a "test set" is a set of data used in various areas of information science to assess the strength and utility of a predictive relationship. Test sets are used in artificial intelligence, machine learning, genetic programming, intelligent systems, and statistics. In all these fields, a test set has much the same role.

Data collected during analysis may be quantified for one or more than one metabolite. Quantifying data may be obtained by measuring the levels or intensities of specific metabolites present in a sample. The quantifying data may be compared to corresponding data from one or more than one reference sample. A "reference sample" is any suitable reference sample for the particular disease state. For example, a reference sample may be a sample from a control individual, i.e., a person not suffering from ASD with or without a family history of ASD (also referred to herein as a "typically developing individual," or "normal" counterpart. A reference sample may also be a sample obtained from a patient clinically diagnosed with ASD. As would be understood by a person of skill in the art, more than one reference sample may be used for comparison to the quantifying data.

As used herein, the term "metabolite" or "cellular metabolite" refers to specific small molecules, the levels or intensities of which are measured in a sample, and that may be used as markers to diagnose a disease state. As used herein, the term "feature" refers to a single small metabolite, or a fragment of a metabolite. Metabolites include, but are not limited to, sugars, organic acids, amino acids, fatty acids, hormones, vitamins, acids, bases, lipids, glycosides, amines, oximes, esters, dipeptides, tripeptides, cholesterols, oxysterols, glycerols, steroids, oligopeptides (less than about 100 amino acids in length), as well as ionic fragments thereof. In some aspects, metabolites are less than about 3000 Daltons in molecular weight. In some aspects, metabolites are less than about 1500 Daltons in molecular weight. In some aspects, metabolites are from about 10 to about 3000 Daltons in molecular weight. In some aspects, metabolites are from about 50 to about 3000 Daltons in molecular weight. In some aspects, metabolites are from about 10 Daltons to about 1500 Dalton in molecular weight. In some aspects, metabolites are from about 50 Daltons to about 1500 Dalton in molecular weight.

As used herein, the term "biomarker" or "metabolic biomarker" refers to metabolites that exhibit statistically significant alterations between diseased and controls.

The terms "metabolic signature" and "biomarker profile" as used herein refer to one or a plurality of metabolites identified by the inventive methods. A metabolic signature of autism is a population of cellular metabolites that are significantly altered in autistic patient biofluids, providing a molecular fingerprint of autism spectral disorders. Such a metabolic signature of autism may be used to diagnose autism in an individual.

The invention provides methods for identifying metabolites in biofluids of individuals with autism. Said metabolites are found using the methods described herein to be differentially secreted in patient tissues or biofluids. These metabolites may be found in either greater or lesser amounts in autistic as compared to non-autistic individuals. Thus, the present invention includes a blood test for the diagnosis of ASD. ASD is a lifelong neurodevelopmental disorder characterized by deficits in social interaction, communication and repetitive or stereotypical behaviors which has recently seen a dramatic increase in prevalence, reaching an estimate of 1 in 50 school-aged children. Earlier diagnosis and treatment is important for optimal therapeutic outcomes. The blood test of the present invention can be performed at an earlier age will have a dramatic impact on earlier therapeutic interventions and better outcomes for ASD children.

Metabolic biomarkers may be identified by their unique molecular mass and consistency, thus the actual identity of the underlying compound that corresponds to the biomarker is not required for the practice of this invention. Biomarkers may be identified using, for example, Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, tandem mass spectrometry (e.g., MS/MS, MS/MS/MS, ESI-MS/MS etc.), secondary ion mass spectrometry (SIMS), and/or ion mobility spectrometry (e.g. GC-IMS, IMS-MS, LC-IMS, LC-IMS-MS etc.). Alternatively, certain biomarkers can be identified by, for example, gene expression analysis, including real-time PCR, RT-PCR, Northern analysis, and in situ hybridization.

In some aspects, a method for identifying a metabolomic signature characteristic for autism in a human may include one or more of the steps:

assaying a collection of biosamples isolated from autistic subjects for one or a plurality of small molecule metabolites by two or more methodologies selected from gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg);

assaying a collection of biosamples isolated from non-autistic control subjects for one or a plurality of small molecule metabolites by the same two or more methodologies selected from GC-MS, C8pos, C8neg, HILICpos, and/or HILICneg;

identifying for each of the two or methodologies one or a plurality of small molecule metabolites that are differentially produced in autistic subjects as compared to non-autistic control subjects;

combining the plurality of small molecule metabolites that are differentially produced in autistic subjects as compared to non-autistic control subjects identified by each of the two or more methodologies to form a training set of small molecule metabolites; and selecting from the training set a subset of small molecule metabolites with a statistically significant abundance difference in the biosamples isolated from autistic subjects as compared to the biosamples isolated from control non-autistic control subjects;

wherein the subset of small molecules with a statistically significant abundance difference in the biosamples isolated from autistic subjects as compared to the biosamples isolated from control non-autistic control subjects comprises a metabolomic signature for autism.

In some aspects, biosamples are assayed by three or more, four or more, or all five of the methodologies of gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and hydrophilic interaction liquid chromatography coupled to electrospray ionization in negative ion polarity (HILICneg).

In some aspects, a method for identifying a metabolomic signature characteristic for autism in a human may include one or more of the steps:

a) assaying a collection of biosamples isolated from autistic subjects for one or a plurality of small molecule metabolites by gas chromatography mass spectrometry (GCMS);

b) assaying a collection of biosamples isolated from non-autistic control subjects for one or a plurality of small molecule metabolites by GCMS;

c) identifying one or a plurality of small molecule metabolites assayed by GCMS that are differentially produced in autistic subjects as compared to non-autistic control subjects;

d) assaying the collection of biosamples isolated from autistic subjects for one or a plurality of small molecule metabolites by one or more untargeted liquid chromatography-high resolution mass spectrometry methodologies (LC/HRMS);

e) assaying the collection of biosamples isolated from non-autistic control subjects for one or a plurality of small molecule metabolites by one or more untargeted LC/HRMS methodologies;

f) identifying one or a plurality of small molecule metabolites assayed by the one or more untargeted LC/HRMS methodologies that are differentially produced in autistic subjects as compared to non-autistic control subjects;

g) combining the plurality of small molecule metabolites identified by step c) and step f) to form a training set of small molecule metabolites; and h) selecting from the training set a subset of small molecule metabolites with a statistically significant abundance difference in the collection of biosamples isolated form autistic patients as compared to the collection of biosamples isolated from control non-autistic control subjects;

wherein the subset of small molecules of step h) comprises a metabolomic signature for autism in a human.

In some aspects, assaying biosamples by one or more untargeted liquid chromatography-high resolution mass spectrometry methodologies (LC/HRMS) includes assaying the biosamples by C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg).

The present invention includes methods for identifying a metabolomic signature characteristic for autism in a human including the steps of:

a) assaying a collection of biosamples isolated from autistic subjects for one or a plurality of small molecule metabolites by gas chromatography mass spectrometry (GCMS);

b) assaying a collection of biosamples isolated from non-autistic control subjects for one or a plurality of small molecule metabolites by GCMS;

c) identifying one or a plurality of small molecule metabolites assayed by GCMS that are differentially produced in autistic subjects as compared to non-autistic control subjects;

d) assaying the collection of biosamples isolated from autistic subjects for one or a plurality of small molecule metabolites by C8 liquid chromatography coupled to electrospray ionization in positive ion polarity (C8pos);

e) assaying the collection of biosamples isolated from non-autistic control subjects for one or a plurality of small molecule metabolites by C8pos;

f) identifying one or a plurality of small molecule metabolites assayed by C8pos that are differentially produced in autistic subjects as compared to non-autistic control subjects;

g) assaying the collection of biosamples isolated from autistic subjects for one or a plurality of small molecule metabolites by C8 liquid chromatography coupled to electrospray ionization in negative ion polarity (C8neg);

h) assaying the collection of biosamples isolated from non-autistic control subjects for one or a plurality of small molecule metabolites by C8neg;

i) identifying one or a plurality of small molecule metabolites assayed by C8neg that are differentially produced in autistic subjects as compared to non-autistic control subjects;

j) assaying the collection of biosamples isolated from autistic subjects for one or a plurality of small molecule metabolites by hydrophilic interaction liquid chromatography coupled to electrospray ionization in positive ion polarity (HILICpos);

k) assaying the collection of biosamples isolated from non-autistic control subjects for one or a plurality of small molecule metabolites by HILICpos;

l) identifying one or a plurality of small molecule metabolites assayed by HILICpos that are differentially produced in autistic subjects as compared to non-autistic control subjects;

m) assaying the collection of biosamples isolated from autistic subjects for one or a plurality of small molecule metabolites by hydrophilic interaction liquid chromatography coupled to electrospray ionization in negative ion polarity (HILICneg);

n) assaying the collection of biosamples isolated from non-autistic control subjects for one or a plurality of small molecule metabolites by HILICneg;

o) identifying one or a plurality of small molecule metabolites assayed by HILICneg that are differentially produced in autistic subjects as compared to non-autistic control subjects;

p) combining the plurality of small molecule metabolites identified by step c), step f), step I), step l), and step o) to form a training set of small molecule metabolites; and q) selecting from the training set a subset of small molecule metabolites with a statistically significant abundance difference in the collection of biosamples isolated form autistic patients as compared to the collection of biosamples isolated from control non-autistic control subjects; wherein the subset of small molecules of step q) comprises a metabolomic signature for autism in a human.

Metabolites, as set forth herein, can be detected using alternative spectrometry methods or other methods known in the art, in addition to any of those described herein.

In some aspects of the methods for identifying a metabolomic signature characteristic for autism in a human of the present invention, a training set a subset of small molecule metabolites with a statistically significant abundance difference in the collection of biosamples isolated from autistic patients as compared to the collection of biosamples isolated from control non-autistic control subjects may be identified by univariate analysis, multivariate analysis, machine learning analysis, support vector machine analysis (SVM), and/or partial least squares analysis (PLS).

The present invention provides for metabolomic signatures for autism produced according to the methods described above. Such a signature may include any of the metabolites described herein, taken alone, as a population, or in any informative combination, as biomarkers of autism.

For example, in some aspects, a metabolic signature of autism may include any one or more of the 179 metabolites listed in Table 6. For example, at least about 5 or more of the metabolites, at least about 10 or more of the metabolites, at least about 20 or more of the metabolites, at least about 30 or more of the metabolites, at least about 40 or more of the metabolites, at least about 50 or more of the metabolites, at least about 60 or more of the metabolites, at least about 70 or more of the metabolites, at least about 80 or more of the metabolites, at least about 90 or more of the metabolites, at least about 100 or more of the metabolites, at least about 110 or more of the metabolites, at least about 120 or more of the metabolites, at least about 130 or more of the metabolites, at least about 140 or more of the metabolites, at least about 150 or more of the metabolites, at least about 160 or more of the metabolites, or at least about 170 or more of the metabolites listed in Table 6.

In some aspects, for example, a metabolic signature of autism may include about 10 of the metabolites, about 20 of the metabolites, about 30 of the metabolites, about 40 of the metabolites, about 50 of the metabolites, about 60 of the metabolites, about 70 of the metabolites, about 80 of the metabolites, about 90 of the metabolites, about 100 of the metabolites, about 110 of the metabolites, about 120 of the metabolites, about 130 of the metabolites, about 140 of the metabolites, about 150 of the metabolites, about 160 of the metabolites, or about 170 of the metabolites listed in Table 6.

In some aspects, a metabolic signature of autism may include a range of the metabolites listed in Table 6, including, for example, about 10 to about 20 of the metabolites, about 10 to about 30 of the metabolites, about 10 to about 40 of the metabolites, about 10 to about 50 of the metabolites, about 10 to about 60 of the metabolites, about 10 to about 70 of the metabolites, about 10 to about 80 of the metabolites, about 10 to about 90 of the metabolites, about 10 to about 100 of the metabolites, about 10 to about 110 of the metabolites, about 10 to about 120 of the metabolites, about 10 to about 130 of the metabolites, about 10 to about 140 of the metabolites, about 10 to about 150 of the metabolites, about 10 to about 160 of the metabolites, about 10 to about 170 of the metabolites, about 20 to about 30 of the metabolites, about 20 to about 40 of the metabolites, about 20 to about 50 of the metabolites, about 20 to about 60 of the metabolites, about 20 to about 70 of the metabolites, about 20 to about 80 of the metabolites, about 20 to about 90 of the metabolites, about 20 to about 100 of the metabolites, about 20 to about 110 of the metabolites, about 20 to about 120 of the metabolites, about 20 to about 130 of the metabolites, about 20 to about 140 of the metabolites, about 20 to about 150 of the metabolites, about 20 to about 160 of the metabolites, about 20 to about 170 of the metabolites, about 30 to about 40 of the metabolites, about 30 to about 50 of the metabolites, about 30 to about 60 of the metabolites, about 30 to about 70 of the metabolites, about 30 to about 80 of the metabolites, about 30 to about 90 of the metabolites, about 30 to about 100 of the metabolites, about 30 to about 110 of the metabolites, about 30 to about 120 of the metabolites, about 30 to about 130 of the metabolites, about 30 to about 140 of the metabolites, about 30 to about 150 of the metabolites, about 30 to about 160 of the metabolites, about 30 to about 170 of the metabolites, about 40 to about 50 of the metabolites, about 40 to about 60 of the metabolites, about 40 to about 70 of the metabolites, about 40 to about 80 of the metabolites, about 40 to about 90 of the metabolites, about 40 to about 100 of the metabolites, about 40 to about 110 of the metabolites, about 40 to about 120 of the metabolites, about 40 to about 130 of the metabolites, about 40 to about 140 of the metabolites, about 40 to about 150 of the metabolites, about 40 to about 160 of the metabolites, about 40 to about 170 of the metabolites, about 50 to about 60 of the metabolites, about 50 to about 70 of the metabolites, about 50 to about 80 of the metabolites, about 50 to about 90 of the metabolites, about 50 to about 100 of the metabolites, about 50 to about 110 of the metabolites, about 50 to about 120 of the metabolites, about 50 to about 130 of the metabolites, about 50 to about 140 of the metabolites, about 50 to about 150 of the metabolites, about 50 to about 160 of the metabolites, about 50 to about 170 of the metabolites, about 60 to about 60 of the metabolites, about 60 to about 70 of the metabolites, about 60 to about 80 of the metabolites, about 60 to about 90 of the metabolites, about 60 to about 100 of the metabolites, about 60 to about 110 of the metabolites, about 60 to about 120 of the metabolites, about 60 to about 130 of the metabolites, about 60 to about 140 of the metabolites, about 60 to about 150 of the metabolites, about 60 to about 160 of the metabolites, about 60 to about 170 of the metabolites, about 70 to about 80 of the metabolites, about 70 to about 90 of the metabolites, about 70 to about 100 of the metabolites, about 70 to about 110 of the metabolites, about 70 to about 120 of the metabolites, about 70 to about 130 of the metabolites, about 70 to about 140 of the metabolites, about 70 to about 150 of the metabolites, about 70 to about 160 of the metabolites, about 70 to about 170 of the metabolites, about 80 to about 90 of the metabolites, about 80 to about 100 of the metabolites, about 80 to about 110 of the metabolites listed, about 80 to about 120 of the metabolites, about 80 to about 130 of the metabolites, about 80 to about 140 of the metabolites, about 80 to about 150 of the metabolites, about 80 to about 160 of the metabolites, about 80 to about 170 of the metabolites, about 90 to about 100 of the metabolites, about 90 to about 110 of the metabolites, about 90 to about 120 of the metabolites, about 90 to about 130 of the metabolites, about 90 to about 140 of the metabolites, about 90 to about 150 of the metabolites, about 90 to about 160 of the metabolites, about 90 to about 170 of the metabolites, about 100 to about 110 of the metabolites, about 100 to about 120 of the metabolites, about 100 to about 130 of the metabolites, about 100 to about 140 of the metabolites, about 100 to about 150 of the metabolites, about 100 to about 160 of the metabolites, about 100 to about 170 of the metabolites, about 110 to about 120 of the metabolites, about 110 to about 130 of the metabolites, about 110 to about 140 of the metabolites, about 110 to about 150 of the metabolites, about 110 to about 160 of the metabolites, about 110 to about 170 of the metabolites, about 120 to about 130 of the metabolites, about 120 to about 140 of the metabolites, about 120 to about 150 of the metabolites, about 120 to about 160 of the metabolites, about 120 to about 170 of the metabolites, about 130 to about 140 of the metabolites, about 130 to about 150 of the metabolites, about 130 to about 160 of the metabolites, about 130 to about 170 of the metabolites, about 130 to about 150 of the metabolites, about 130 to about 160 of the metabolites, about 130 to about 170 of the metabolites, about 140 to about 150 of the metabolites, about 140 to about 160 of the metabolites, about 140 to about 170 of the metabolites, about 150 to about 160 of the metabolites, about 150 to about 170 of the metabolites, or about 160 to about 170 of the metabolites listed in Table 6.

For example, a metabolic signature of autism may include one or more of the metabolites listed in Table 5. For example, a metabolic signature of autism may include any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one metabolites selected from homocitrulline, 2-hydroxyvaleric acid, cystine, aspartic acid, isoleucine, creatinine, serine, 4-hydroxyphenyllactic acid, citric acid, glutamic acid, lactic acid, DHEA sulfate, glutaric acid, 5-hydroxynorvaline, heptadecanoic acid, 5-aminovaleric acid lactam, succinic acid, myristic acid, 2-hydroxyvaleric acid, methylhexadecanoic acid, and/or 3-aminoisobutyric acid.

For example, a metabolic signature of autism may include one or more of the metabolites listed in Table 9; including, for example, any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, any twenty one or more metabolites, any twenty two or more metabolites, any twenty three or more metabolites, any twenty four or more metabolites, any twenty five or more metabolites, or twenty six metabolites selected from 2-aminooctanoic acid, acesulfame, ADMA, choline, CMPF, cysteine, cystine, DHEA sulfate (DHEAS), glycine, glycocholic acid, hypoxanthine, indoleacrylic acid, indoxyl sulfate, LysoPC(16:1(9Z)), LysoPE(0:0/18:1(9Z)), LysoPE(22:6(4Z,7Z,10Z,13Z,16Z,19Z)/0:0), LysoPE(22:6(4Z,7Z,10Z,13Z,16Z,19Z)/0:0), methionine, p-cresol sulfate, phenylalanine, phenyllactic acid, proline, serotonin, tryptophan, uric acid or valine.

For example, a metabolic signature of autism may include one or more of the metabolites listed in FIG. 13; including, for example, any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, any twenty one or more metabolites, any twenty two or more metabolites, any twenty three or more metabolites, any twenty four or more metabolites, any twenty five or more metabolites, any twenty six metabolites, any twenty seven or more of the metabolites, any twenty eight or more of the metabolites, or twenty nine of the metabolites selected from homocitrulline, glutaric acid, saccharopine, 5-aminovaleric acid, lactate, succinate, isocitrate, DHEAS, DHA, androsterone sulfate, 27-norcholesterol, Lyso PE, PE, long chain Fas, LysoPC, asparate, glutamate, acetylornithine, valine, isoleucine, ketoleucine, serine, homocysteic acid, valine, cystine, hydroxyacetone, phosphohydroxypyruvate, indole-3-lactate, and/or 3-amino isobutyrate.

Any one or more of such metabolites may be quantified gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), or hydrophilic interaction liquid chromatography coupled to electrospray ionization in negative ion polarity (HILICneg). In some aspects, any one or more of such metabolites may be quantified by the methodology indicated in Table 5, Table 6, or Table 9.

In some aspects of the methods of the present invention, the chemical identity of small molecules that exhibit statistically significant differences between autistic and non-autistic individuals are confirmed. The chemical structures of metabolites identified as statistically significantly different between autistic and non-autistic subjects may be confirmed using HRMS methods, using chromatographic conditions identical to those used for their discovery. HRMS-MS analyses may be performed on Agilent QTOF mass spectrometers for patient samples, reference compounds and samples spiked with reference compounds. Ionization and collision energy conditions may be optimized to obtain the highest quality MS-MS spectra. The resulting HRMS or HR-MS-MS ion fragmentation spectra may be compared to confirm annotated identities for each small molecule metabolite to establish a panel of validated candidate diagnostic biomarkers. The data may be compared to spectra available in several locations, including public databases database. If an MS-MS spectrum does not match available database spectra, a reference compound may be obtained for the putatively annotated compounds and MS-MS spectra will be obtained for the reference compound then compared with that of the sample.

In some aspects, a metabolic signature of autism is demonstrated by an increase or a decrease in abundance when compared to typical/normal controls. Including, for example, decreased homocitrulline, increased glutaric acid, increased saccharopine, increased 5-aminovaleric acid, increased lactate, increased succinate, decreased isocitrate, increased DHEAS, increased DHA, increased androsterone sulfate, increased 27-norcholesterol, decreased Lyso PE, decreased PE, decreased long chain Fas, decreased LysoPC, increased asparate, increased glutamate, increased acetylornithine, decreased valine, decreased isoleucine, increased ketoleucine, increased serine, decreased homocysteic acid, decreased valine, decreased cystine, increased hydroxyacetone, increased phosphohydroxypyruvate, decreased indole-3-lactate, and/or increased 3-amino isobutyrate in comparison to normal controls.

This may be measured as an average abundance ratio relative to a normal control. In some aspects, an average abundance ratio of other than about 1 may be indicative of autism. For example, an average abundance ratio of greater than about 1 (for example, including, but not limited to, about 1.01, about 1.02, about 1.03, about 1.04, about 1.05, about 1.06, about 1.07, about 1.08, about 1.09, about 1.1, about 1.11, about 1.12, about 1.13, about 1.14, about 1.15, about 1.16, about 1.17, about 1.18, about 1.19, about 1.2, about 1.21, about 1.22, about 1.23, about 1.24, about 1.25, about 1.26, about 1.27, about 1.28, about 1.29, about 1.3, about 1.31, about 1.32, about 1.33, about 1.34, about 1.35, about 1.36, about 1.37, about 1.38, about 1.39, about 1.4, about 1.41, about 1.42, about 1.43, about 1.44, about 1.45, about 1.46, about 1.47, about 1.48, about 1.49, or about 1.5) may be indicative of autism. In some aspects, an average abundance ratio of less than about 1 (for example, including, but not limited to, about 0.99, about 0.98, about 0.97, about 0.96, about 0.95, about 0.94, about 0.93, about 0.92, about 0.91, about 0.9, about 0.89, about 0.88, about 0.87, about 0.86, about 0.85, about 0.84, about 0.83, about 0.82, about 0.81, about 0.8, about 0.79, about 0.78, about 0.77, about 0.76, about 0.75, about 0.74, about 0.73, about 0.72, about 0.71, about 0.7, about 0.69, about 0.68, about 0.67, about 0.66, about 0.65, about 0.64, about 0.63, about 0.62, about 0.61, about 0.6, about 0.59, about 0.58, about 0.57, about 0.56, about 0.55, about 0.54, about 0.53, about 0.52, about 0.51, or about 0.5) may be indicative of autism.

The present invention relates to small molecules or metabolites found to have significantly different abundances or intensities between plasma samples from autistic children and typically developing, normal children. And, the present invention includes methods of assessing a subject's risk for developing autism and/or for the diagnosis of autism. A subject may be determined to be at risk for ASD or diagnosed with ASD based on a statistically significant (p<0.05) increase or decrease relative to the corresponding data of a reference sample from a non-ASD subject in the level of one or more of the small molecule metabolites of a metabolic signature identified by the methods described herein.

In some aspects, the quantification of one or more small molecule metabolites of a metabolic signature of autism may be assayed using a physical separation method, such as, for example, one or more methodologies selected from gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg). In some aspects, the determination of a metabolite may be by a methodology other than a physical separation method, such as for example, a colorimetric, enzymatic, immunological methodology.

In some aspects, a method of assessing a subject's risk for autism and for the diagnosis of autism may include assaying a biosample from the subject for one or a plurality of small molecule metabolites and quantifying the amount of one or more of the 179 small molecule metabolites listed in Table 6, wherein a statistically significant abundance difference as compared to non-autistic controls in one or more of the 179 small molecule metabolites listed in Table 6 indicates an increased risk of autism.

In some aspects, a method of assessing a subject's risk for autism and for the diagnosis of autism may include a step of assaying a biosample from the subject for one or a plurality of small molecule metabolites by one or more methodologies selected from gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg) and quantifying the amount of one or more of the 179 small molecule metabolites listed in Table 6, wherein a statistically significant abundance difference as compared to non-autistic controls in one or more of the 179 small molecule metabolites listed in Table 6 indicates an increased risk of autism.

In some aspects, one or more of the 179 metabolites listed in Table 6 may include, for example, at least about 5 or more of the metabolites, at least about 10 or more of the metabolites, at least about 20 or more of the metabolites, at least about 30 or more of the metabolites, at least about 40 or more of the metabolites, at least about 50 or more of the metabolites, at least about 60 or more of the metabolites, at least about 70 or more of the metabolites, at least about 80 or more of the metabolites, at least about 90 or more of the metabolites, at least about 100 or more of the metabolites, at least about 110 or more of the metabolites, at least about 120 or more of the metabolites, at least about 130 or more of the metabolites, at least about 140 or more of the metabolites, at least about 150 or more of the metabolites, at least about 160 or more of the metabolites, or at least about 170 or more of the metabolites listed in Table 6.

In some aspects, one or more of the 179 metabolites listed in Table 6 may include, for example, about 10 of the metabolites, about 20 of the metabolites, about 30 of the metabolites, about 40 of the metabolites, about 50 of the metabolites, about 60 of the metabolites, about 70 of the metabolites, about 80 of the metabolites, about 90 of the metabolites, about 100 of the metabolites, about 110 of the metabolites, about 120 of the metabolites, about 130 of the metabolites, about 140 of the metabolites, about 150 of the metabolites, about 160 of the metabolites, or about 170 of the metabolites listed in Table 6.

In some aspects, one or more of the 179 metabolites listed in Table 6 may include a range of the metabolites, including, for example, about 10 to about 20 of the metabolites, about 10 to about 30 of the metabolites, about 10 to about 40 of the metabolites, about 10 to about 50 of the metabolites, about 10 to about 60 of the metabolites, about 10 to about 70 of the metabolites, about 10 to about 80 of the metabolites, about 10 to about 90 of the metabolites, about 10 to about 100 of the metabolites, about 10 to about 110 of the metabolites, about 10 to about 120 of the metabolites, about 10 to about 130 of the metabolites, about 10 to about 140 of the metabolites, about 10 to about 150 of the metabolites, about 10 to about 160 of the metabolites, about 10 to about 170 of the metabolites, about 20 to about 30 of the metabolites, about 20 to about 40 of the metabolites, about 20 to about 50 of the metabolites, about 20 to about 60 of the metabolites, about 20 to about 70 of the metabolites, about 20 to about 80 of the metabolites, about 20 to about 90 of the metabolites, about 20 to about 100 of the metabolites, about 20 to about 110 of the metabolites, about 20 to about 120 of the metabolites, about 20 to about 130 of the metabolites, about 20 to about 140 of the metabolites, about 20 to about 150 of the metabolites, about 20 to about 160 of the metabolites, about 20 to about 170 of the metabolites, about 30 to about 40 of the metabolites, about 30 to about 50 of the metabolites, about 30 to about 60 of the metabolites, about 30 to about 70 of the metabolites, about 30 to about 80 of the metabolites, about 30 to about 90 of the metabolites, about 30 to about 100 of the metabolites, about 30 to about 110 of the metabolites, about 30 to about 120 of the metabolites, about 30 to about 130 of the metabolites, about 30 to about 140 of the metabolites, about 30 to about 150 of the metabolites, about 30 to about 160 of the metabolites, about 30 to about 170 of the metabolites, about 40 to about 50 of the metabolites, about 40 to about 60 of the metabolites, about 40 to about 70 of the metabolites, about 40 to about 80 of the metabolites, about 40 to about 90 of the metabolites, about 40 to about 100 of the metabolites, about 40 to about 110 of the metabolites, about 40 to about 120 of the metabolites, about 40 to about 130 of the metabolites, about 40 to about 140 of the metabolites, about 40 to about 150 of the metabolites, about 40 to about 160 of the metabolites, about 40 to about 170 of the metabolites, about 50 to about 60 of the metabolites, about 50 to about 70 of the metabolites, about 50 to about 80 of the metabolites, about 50 to about 90 of the metabolites, about 50 to about 100 of the metabolites, about 50 to about 110 of the metabolites, about 50 to about 120 of the metabolites, about 50 to about 130 of the metabolites, about 50 to about 140 of the metabolites, about 50 to about 150 of the metabolites, about 50 to about 160 of the metabolites, about 50 to about 170 of the metabolites, about 60 to about 60 of the metabolites, about 60 to about 70 of the metabolites, about 60 to about 80 of the metabolites, about 60 to about 90 of the metabolites, about 60 to about 100 of the metabolites, about 60 to about 110 of the metabolites, about 60 to about 120 of the metabolites, about 60 to about 130 of the metabolites, about 60 to about 140 of the metabolites, about 60 to about 150 of the metabolites, about 60 to about 160 of the metabolites, about 60 to about 170 of the metabolites, about 70 to about 80 of the metabolites, about 70 to about 90 of the metabolites, about 70 to about 100 of the metabolites, about 70 to about 110 of the metabolites, about 70 to about 120 of the metabolites, about 70 to about 130 of the metabolites, about 70 to about 140 of the metabolites, about 70 to about 150 of the metabolites, about 70 to about 160 of the metabolites, about 70 to about 170 of the metabolites, about 80 to about 90 of the metabolites, about 80 to about 100 of the metabolites, about 80 to about 110 of the metabolites listed, about 80 to about 120 of the metabolites, about 80 to about 130 of the metabolites, about 80 to about 140 of the metabolites, about 80 to about 150 of the metabolites, about 80 to about 160 of the metabolites, about 80 to about 170 of the metabolites, about 90 to about 100 of the metabolites, about 90 to about 110 of the metabolites, about 90 to about 120 of the metabolites, about 90 to about 130 of the metabolites, about 90 to about 140 of the metabolites, about 90 to about 150 of the metabolites, about 90 to about 160 of the metabolites, about 90 to about 170 of the metabolites, about 100 to about 110 of the metabolites, about 100 to about 120 of the metabolites, about 100 to about 130 of the metabolites, about 100 to about 140 of the metabolites, about 100 to about 150 of the metabolites, about 100 to about 160 of the metabolites, about 100 to about 170 of the metabolites, about 110 to about 120 of the metabolites, about 110 to about 130 of the metabolites, about 110 to about 140 of the metabolites, about 110 to about 150 of the metabolites, about 110 to about 160 of the metabolites, about 110 to about 170 of the metabolites, about 120 to about 130 of the metabolites, about 120 to about 140 of the metabolites, about 120 to about 150 of the metabolites, about 120 to about 160 of the metabolites, about 120 to about 170 of the metabolites, about 130 to about 140 of the metabolites, about 130 to about 150 of the metabolites, about 130 to about 160 of the metabolites, about 130 to about 170 of the metabolites, about 130 to about 150 of the metabolites, about 130 to about 160 of the metabolites, about 130 to about 170 of the metabolites, about 140 to about 150 of the metabolites, about 140 to about 160 of the metabolites, about 140 to about 170 of the metabolites, about 150 to about 160 of the metabolites, about 150 to about 170 of the metabolites, or about 160 to about 170 of the metabolites listed in Table 6.

In some aspects, a method of assessing a subject's risk for autism and/or for the diagnosis of autism may include assaying a biosample from the subject for one or a plurality of small molecule metabolites and quantifying the amount of one or more of the 21 small molecule metabolites listed in Table 5, wherein a statistically significant abundance difference as compared to non-autistic controls in one or more of the 21 small molecule metabolites listed in Table 5 indicates an increased risk of autism. For example, a statistically significant abundance difference as compared to non-autistic controls of any one or more any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one metabolites of homocitrulline, 2-hydroxyvaleric acid, cystine, aspartic acid, isoleucine, creatinine, serine, 4-hydroxyphenyllactic acid, citric acid, glutamic acid, lactic acid, DHEA sulfate, glutaric acid, 5-hydroxynorvaline, heptadecanoic acid, 5-aminovaleric acid lactam, succinic acid, myristic acid, 2-hydroxyvaleric acid, methylhexadecanoic acid, and/or 3-aminoisobutyric acid indicates an increased risk of autism.

In some aspects, a method of assessing a subject's risk for autism and for the diagnosis of autism may include assaying a biosample from the subject for one or a plurality of small molecule metabolites and quantifying the amount of one or more of the 26 small molecule metabolites listed in Table 9, wherein a statistically significant abundance difference as compared to non-autistic controls in one or more of the 26 small molecule metabolites listed in Table 9 indicates an increased risk of autism. For example, a statistically significant abundance difference as compared to non-autistic controls of any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one or more metabolites, any twenty two or more metabolites, any twenty three or more metabolites, any twenty four or more metabolites, any twenty five or more metabolites, and/or twenty six metabolites of 2-aminooctanoic acid, acesulfame, ADMA, choline, CMPF, cysteine, cystine, DHEA sulfate (DHEAS), glycine, glycocholic acid, hypoxanthine, indoleacrylic acid, indoxyl sulfate, LysoPC(16:1(9Z)), LysoPE(0:0/18:1(9Z)), LysoPE(22:6(4Z,7Z,10Z,13Z,16Z, 19Z)/0:0), LysoPE(22:6(4Z,7Z,10Z,13Z,16Z,19Z)/0:0), methionine, p-cresol sulfate, phenylalanine, phenyllactic acid, proline, serotonin, tryptophan, uric acid, and/or valine indicates an increased risk of autism.

In some aspects, a method of assessing a subject's risk for autism and for the diagnosis of autism may include assaying a biosample from the subject for one or a plurality of small molecule metabolites and quantifying the amount of one or more of the 29 small molecule metabolites listed in FIG. 13, wherein a statistically significant abundance difference as compared to non-autistic controls in one or more of the 29 small molecule metabolites listed in FIG. 13 indicates an increased risk of autism. For example, a statistically significant abundance difference as compared to non-autistic controls of any one or more of, any one or more of the metabolites, any two or more metabolites, any three or more metabolites, any four or more metabolites, any five or more metabolites, any six or more metabolites, any seven or more metabolites, any eight or more metabolites, any nine or more metabolites, any ten or more metabolites, any eleven or more metabolites, any twelve or more metabolites, any thirteen or more metabolites, any fourteen or more metabolites, any fifteen or more metabolites, any sixteen or more metabolites, any seventeen or more metabolites, any eighteen or more metabolites, any nineteen or more metabolites, any twenty or more metabolites, or twenty one or more metabolites, any twenty two or more metabolites, any twenty three or more metabolites, any twenty four or more metabolites, any twenty five or more metabolites, any twenty six metabolites or more metabolites, any twenty seven metabolites or more metabolites, any twenty eight metabolites or more metabolites, and/or twenty nine metabolites of homocitrulline, glutaric acid, saccharopine, 5-aminovaleric acid, lactate, succinate, isocitrate, DHEAS, DHA, androsterone sulfate, 27-norcholesterol, Lyso PE, PE, long chain Fas, LysoPC, asparate, glutamate, acetylornithine, valine, isoleucine, ketoleucine, serine, homocysteic acid, valine, cystine, hydroxyacetone, phosphohydroxypyruvate, indole-3-lactate, and/or 3-amino isobutyrate indicates an increased risk of autism.

In some aspects, a method of assessing a subject's risk for autism and for the diagnosis of autism may include assaying a biosample from the subject for decreased homocitrulline, increased glutaric acid, increased saccharopine, increased 5-aminovaleric acid, increased lactate, increased succinate, decreased isocitrate, increased DHEAS, increased DHA, increased androsterone sulfate, increased 27-norcholesterol, decreased Lyso PE, decreased PE, decreased long chain Fas, decreased LysoPC, increased asparate, increased glutamate, increased acetylornithine, decreased valine, decreased isoleucine, increased ketoleucine, increased serine, decreased homocysteic acid, decreased valine, decreased cystine, increased hydroxyacetone, increased phosphohydroxypyruvate, decreased indole-3-lactate, and/or increased 3-amino isobutyrate.

In some aspects, a method of assessing a subject's risk for autism and for the diagnosis of autism may include assaying a biosample from the subject for decreased glycine, serine, threonine, alanine, histidine, glutamyl amino acids, taurine, and/or carnosine.

In some aspects, a method of assessing a subject's risk for autism and for the diagnosis of autism may include assaying a biosample from the subject for decreased homocitrulline.

Biosamples may be from any of a variety of mammalian subjects. In preferred embodiments, a biosample is from a human subject. A biosample may be from an individual clinically diagnosed with ASD. ASD may be diagnosed by any of a variety of well-known clinical criteria. For example, diagnosis of autism spectrum disorder may be based on the DSM-IV criteria determined by an experienced neuropsychologist and/or the Autism Diagnostic Observation Schedule-Generic (ADOS-G) which provides observation of a child's communication, reciprocal social interaction, and stereotyped behavior including an algorithm with cutoffs for autism and autism spectrum disorders.

A biosample may be from an individual determined to be at some risk for ASD (for example by family history) with little or no current ASD symptoms. A biosample may be a suitable reference or control sample from an individual not suffering from ASD with or without a family history of ASD. In some aspects, a plurality of samples is obtained from a population, for example, a population of individuals with ASD, at risk for ASD, or normal, typically developing individuals. A biosample may be from an adult subject. A biosample may be from a child, for example, a child that is under about 6 years of age, under about 4 years of age, under about 2 years of age, or under about 1 year of age, about 1 to about 6 years of age, about 1 to about 5 years of age, about 1 to about 4 years of age, about 1 to about 2 years of age, about 2 to about 6 years of age, about 2 to about 4 years of age, or about 4 to about 6 years of age. A biosample may be from a phenotypic subpopulation of autism subjects, such as, for example, high functioning autism (HFA) or low functioning autism (LFA).

In accordance with the methods disclosed herein, any type of biological sample that originates from anywhere within the body of a subject may be tested, including, but not limited to, blood (including, but no limited to serum or plasma), cerebrospinal fluid (CSF), pleural fluid, urine, stool, sweat, tears, breath, saliva, a tissue sample, amniotic fluid, a chorionic villus sampling, brain tissue, a biopsy of any solid tissue including tumor, adjacent normal, smooth and skeletal muscle, adipose tissue, liver, skin, hair, brain, kidney, pancreas, lung, colon, stomach, or the like may be used. A blood sample may include, for example, a whole blood sample, a blood serum sample, a blood plasma sample, or other blood components, such as, for example, a subfraction of whole blood. A sample may be from a live subject. In some applications, samples may be collected post mortem.

When a blood sample is drawn from a subject, it can be processed in any of many known ways. The range of processing can be from little to none (such as, for example, frozen whole blood) or as complex as the isolation of a particular cell type. Common and routine procedures include the preparation of either serum or plasma from whole blood. All blood sample processing methods, including spotting of blood samples onto solid-phase supports, such as filter paper or other immobile materials, are contemplated by the present invention.

With the preparation of samples for analysis, metabolites may be extracted from their biological source using any number of extraction/clean-up procedures that are typically used in quantitative analytical chemistry.

A computer may be used for statistical analysis. Data for statistical analysis can be extracted from chromatograms (spectra of mass signals) using softwares for statistical methods known in the art. "Statistics" is the science of making effective use of numerical data relating to groups of individuals or experiments. Methods for statistical analysis are well-known in the art. In one embodiment a computer is used for statistical analysis. In one embodiment, the Agilent MassProfiler or MassProfilerProfessional software is used for statistical analysis. In another embodiment, the Agilent MassHunter software Qual software is used for statistical analysis. In other embodiments, alternative statistical analysis methods can be used. Such other statistical methods include the Analysis of Variance (ANOVA) test, Chi-square test, Correlation test, Factor analysis test, Mann-Whitney U test, Mean square weighted derivation (MSWD), Pearson product-moment correlation coefficient, Regression analysis, Spearman's rank correlation coefficient, Student's T test, Welch's T-test, Tukey's test, and Time series analysis. In different embodiments signals from mass spectrometry can be transformed in different ways to improve the performance of the method. Either individual signals or summaries of the distributions of signals (such as mean, median or variance) can be so transformed. Possible transformations include taking the logarithm, taking some positive or negative power, for example the square root or inverse, or taking the arcsin. In different embodiments, statistical classification algorithms are used to create a classification model in order to predict autism and non-autism. Machine learning-based classifiers have been applied in various fields such as machine perception, medical diagnosis, bioinformatics, brain-machine interfaces, classifying DNA sequences, and object recognition in computer vision. Learning-based classifiers have proven to be highly efficient in solving some biological problems.

"Sensitivity" and "specificity" are statistical measures of the performance of a binary classification test. Sensitivity measures the proportion of actual positives which are correctly identified as such (e.g. the percentage of sick people who are correctly identified as having the condition). Specificity measures the proportion of negatives which are correctly identified (e.g. the percentage of healthy people who are correctly identified as not having the condition). These two measures are closely related to the concepts of type I and type II errors. A theoretical, optimal prediction can achieve 100% sensitivity (i.e. predict all people from the sick group as sick) and 100% specificity (i.e. not predict anyone from the healthy group as sick). A specificity of 100% means that the test recognizes all actual negatives—for example, in a test for a certain disease, all disease free people will be recognized as disease free. A sensitivity of 100% means that the test recognizes all actual positives—for example, all sick people are recognized as being ill. Thus, in contrast to a high specificity test, negative results in a high sensitivity test are used to rule out the disease. A positive result in a high specificity test can confirm the presence of disease. However, from a theoretical point of view, a 100%-specific test standard can also be ascribed to a 'bogus' test kit whereby the test simply always indicates negative. Therefore the specificity alone does not tell us how well the test recognizes positive cases. Knowledge of sensitivity is also required. For any test, there is usually a trade-off between the measures. For example, in a diagnostic assay in which one is testing for people who have a certain condition, the assay may be set to overlook a certain percentage of sick people who are correctly identified as having the condition (low specificity), in order to reduce the risk of missing the percentage of healthy people who are correctly identified as not having the condition (high sensitivity). Eliminating the systematic error improves accuracy but does not change precision. This trade-off can be represented graphically using a receiver operating characteristic (ROC) curve.

The "accuracy" of a measurement system is the degree of closeness of measurements of a quantity to its actual (true) value. The "precision" of a measurement system, also called reproducibility or repeatability, is the degree to which repeated measurements under unchanged conditions show the same results. Although the two words can be synonymous in colloquial use, they are deliberately contrasted in the context of the scientific method. A measurement system can be accurate but not precise, precise but not accurate, neither, or both. For example, if an experiment contains a systematic error, then increasing the sample size generally increases precision but does not improve accuracy.

The term "predictability" (also called banality) is the degree to which a correct prediction or forecast of a system's state can be made either qualitatively or quantitatively. Perfect predictability implies strict determinism, but lack of predictability does not necessarily imply lack of determinism. Limitations on predictability could be caused by factors such as a lack of information or excessive complexity.

In some embodiments, the invention discloses a method for diagnosing autism with at least about 80% accuracy, at least about 81% accuracy, at least about 82% accuracy, at least about 83% accuracy, at least about 84% accuracy, at least about 85% accuracy, at least about 86% accuracy, at least about 87% accuracy, at least about 88% accuracy, at least about 89% accuracy, at least about 90% accuracy, at least about 91% accuracy, at least about 92% accuracy, at least about 93% accuracy, at least about 94% accuracy, at least about 95% accuracy, at least about 96% accuracy, at least about 97% accuracy, at least about 98% accuracy, or at least about 99% accuracy.

In some embodiments, the invention discloses a method for diagnosing autism with at least about 80% sensitivity, at least about 81% sensitivity, at least about 82% sensitivity, at least about 83% sensitivity, at least about 84% sensitivity, at least about 85% sensitivity, at least about 86% sensitivity, at least about 87% sensitivity, at least about 88% sensitivity, at least about 89% sensitivity, at least about 90% sensitivity, at least about 91% sensitivity, at least about 92% sensitivity, at least about 93% sensitivity, at least about 94% sensitivity, at least about 95% sensitivity, at least about 96% sensitivity, at least about 97% sensitivity, at least about 98% sensitivity, or at least about 99% sensitivity.

In some embodiments, the invention discloses a method for diagnosing autism with at least about 75% specificity, at least about 80% specificity, at least about 81% specificity, at least about 82% specificity, at least about 83% specificity, at least about 84% specificity, at least about 85% specificity, at least about 86% specificity, at least about 87% specificity, at least about 88% specificity, at least about 89% specificity, at least about 90% specificity, at least about 91% specificity, at least about 92% specificity, at least about 93% specificity, at least about 94% specificity, at least about 95% specificity, at least about 96% specificity, at least about 97% specificity, at least about 98% specificity, or at least about 99% specificity, In some embodiments, the invention discloses a method for diagnosing autism with any combination of accuracy, sensitivity, and specificity selected from those described above.

In some embodiments, the invention discloses a method for diagnosing autism with accuracy, sensitivity, and/or specificity as described in the example included herewith.

In some aspects, an average abundance ratio of the concentration of a signature metabolite indicative of autism in an autism sample in comparison to typically developing sample may be determined. Such an average abundance ratio may be utilized in the diagnosis of autism. Further, such an average abundance ratio may be indicative of a phenotypic subpopulation of autism. The average abundance ratio of any number of signature metabolites indicative of autism may be utilized in the determination of autism and/or a phenotypic subpopulation of autism. For example, an average abundance ratio may be determined for any one or any plurality of the metabolites described in Table 5, Table 6, and/or Table 9, as previously described herein. In some aspects, an average abundance of other than about 1 may be indicative of autism and/or a phenotypic subpopulation of autism. For example, a fold change ratio of greater than about 1 (for example, including, but not limited to, about 1.01, about 1.02, about 1.03, about 1.04, about 1.05, about 1.06, about 1.07, about 1.08, about 1.09, about 1.1, about 1.11, about 1.12, about 1.13, about 1.14, about 1.15, about 1.16, about 1.17, about 1.18, about 1.19, about 1.2, about 1.21, about 1.22, about 1.23, about 1.24, about 1.25, about 1.26, about 1.27, about 1.28, about 1.29, about 1.3, about 1.31, about 1.32, about 1.33, about 1.34, about 1.35, about 1.36, about 1.37, about 1.38, about 1.39, about 1.4, about 1.41, about 1.42, about 1.43, about 1.44, about 1.45, about 1.46, about 1.47, about 1.48, about 1.49, or about 1.5) may be indicative of autism and/or a phenotypic subpopulation of autism. For example, a fold change ratio of less than about 1 (for example, including, but not limited to, about 0.99, about 0.98, about 0.97, about 0.96, about 0.95, about 0.94, about 0.93, about 0.92, about 0.91, about 0.9, about 0.89, about 0.88, about 0.87, about 0.86, about 0.85, about 0.84, about 0.83, about 0.82, about 0.81, about 0.8, about 0.79, about 0.78, about 0.77, about 0.76, about 0.75, about 0.74, about 0.73, about 0.72, about 0.71, about 0.7, about 0.69, about 0.68, about 0.67, about 0.66, about 0.65, about 0.64, about 0.63, about 0.62, about 0.61, about 0.6, about 0.59, about 0.58, about 0.57, about 0.56, about 0.55, about 0.54, about 0.53, about 0.52, about 0.51, or about 0.5) may be indicative of autism and/or a phenotypic subpopulation of autism.

In some aspects, a ratio of the concentration in the same sample of one signature metabolite indicative of autism relative to the concentration of a second signature metabolite indicative of autism may be determined. Such a ratio may be utilized in the diagnosis of autism. Further, such a ratio may be indicative of a phenotypic subpopulation of autism. A ratio of any one signature metabolite described herein relative to any second signature metabolite described herein may be determined to indicative of autism and/or a phenotypic subpopulation of autism. Such a signature metabolite described herein includes, but is not limited to, any of those described in Table 5, Table 6, and/or Table 9.

In some aspects, a ratio of the concentration in the same sample of a signature metabolite indicative of autism as described herein relative to the concentration of another metabolite may be determined. Such a ratio may be utilized in the diagnosis of autism. Further, such a ratio may be indicative of a phenotypic subpopulation of autism. Such a signature metabolite described herein includes, but is not limited to, any of those described in Table 5, Table 6, and/or Table 9.

In some aspects, a method for diagnosing autism based on identification and/or quantification of one or more signature metabolites indicative of autism as described herein may further include the identification and/or quantification of one or more additional known markers of autism. For example, one or more of the markers and/or methodologies for their identification and/or quantification as described in US Patent Application 20120190055 ("Molecule Biomarkers of Autism"), which is hereby incorporated by reference in its entirety, may be used. One or more of the markers and/or the methodologies for their identification and/or quantification as described in U.S. Pat. No. 8,273,575 ("Methods for the diagnosis, risk assessment, and monitoring of autism spectrum disorders", which is hereby incorporated by reference in its entirety, may be used. In some aspects, the nucleic acids from a biological sample may be analyzed to determine the genotype and/or expression of genes associated with or relevant to autism.

The metabolic markers and signatures described herein may be utilized in tests, assays, methods, kits for diagnosing, predicting, modulating, or monitoring ASD, including ongoing assessment, monitoring, susceptibility assessment, carrier testing and prenatal diagnosis.

The present invention includes a kit for identifying and/or measuring one or more metabolites associated with the assessment of a risk for ASD. In some aspects, the kit may be for the determination of a metabolite by a physical separation method. In some aspects, the kit may be for the determination of a metabolite by a methodology other than a physical separation method, such as for example, a colorimetric, enzymatic, immunological methodology. In some aspects an assay kit may also include one or more appropriate negative controls and/or positive controls. Kits of the present invention may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by well-known methods, preferably to provide a sterile, contaminant-free environment. As used herein, the term "package" refers to a solid matrix or material such as glass, plastic, paper, foil, and the like. Kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like. In some aspects, a kit may be a packaged combination comprising the basic elements of a first container comprising, in solid form, a specific set of one or more purified metabolites, as described herein, and a second container comprising a physiologically suitable buffer for resuspending the specific subset of purified metabolites. Such a kit may be used by a medical specialist to determine whether or not a subject is at risk for ASD. Appropriate therapeutic intervention may be prescribed or initiated upon the determination of a risk of ASD. One or more of the metabolites described herein may be present in a kit.

The present invention is illustrated by the following examples. It is to be understood that the particular examples, materials, amounts, and procedures are to be interpreted broadly in accordance with the scope and spirit of the invention as set forth herein.

EXAMPLES

Example 1

Biomarkers of Autism Spectrum Disorder in the Blood Plasma of Children

The diagnosis of autism spectrum disorder (ASD) at the earliest age possible is important for initiating optimally effective intervention. Patients can be reliably diagnosed through behavioral testing at approximately two years of age. However, in the United States the average age of diagnosis is around four years. Increasing evidence indicates that ASD has many causes and a variety of genetic risk factors. Identifying metabolic biomarker signatures of ASD from blood samples offers an opportunity for developing early diagnostic tests.

With the present example, a study was undertaken to discover metabolic features from plasma samples that may be able to discriminate children with ASD from typically developing (TD) children. The ultimate goal of this research is to develop blood-based ASD biomarkers.

The etiology of the vast majority of cases of ASD are unknown and their genetics have proven to be incredibly complex (State and Sestan, 2012, *Science;* 337:1301-1303; and Berg and Geschwind, 2012, *Genome Biol;* 13:247). There is now widespread appreciation that there will be many causes of ASD with varying combinations of genetic and environmental risk factors at play. Numerous studies have attempted to identify the causes of the disorder by studying transcriptomics and genomics, leading to the identification of multiple genes associated with ASD (Berg and Geschwind, 2012, *Genome Biol;* 13:247; and Huguet et al., 2013, *Annu Rev Genomics Hum Genet;* 14:191-213). There are currently hundreds of observable genetic variants that account for about 20% of the cases of autism. These data are currently most useful in understanding the intra-familial genetics of autism. For this reason, clinical tests based on genomic measures often include genetic counseling to assess the chance of disease occurrence or recurrence within a family (Bucan et al., 2009, *PLoS Genet;* 5:e1000536; and Wang et al., 2009, *Nature;* 459:528-533). Prediction accuracies of ASD risk based on genomic approaches range from 56% to 70% depending largely on the population of patients assessed. Separate analyses of at least one of the genomic studies by Skafidas et al. has questioned whether the results have been confounded by biases due to ancestral origins (Belgard et al., 2014, *Mol Psychiatry;* 19(4):405-7; and Skafidas et al., 2014, *Mol Psychiatry;* 19(4):504-10). An additional limitation of genomic studies is that the results of environmental influences on the child and/or mother are not discernible. Metabolomics is more sensitive to biochemical changes caused by even subtle environmental influences and therefore can complement genomic approaches by addressing some of these factors that are closer to phenotype.

Given the complexities of the genetic environment of ASD, metabolomic profiling may provide an alternative path to developing early diagnostic tests. Previous metabolic studies of ASD have used biological matrices such as cells, organelles, urine and blood, and have implicated a wide number of metabolites including fatty acids, sterols, intermediary metabolites, phospholipids, and molecules associated with oxidative stress (El-Ansary et al., 2011, *Lipids Health Dis;* 10:62; James et al., 2009, *Am J Clin Nutr;* 89:425-430; Lee and Tierney, 2011, *Autism Res Treat;* 2011:653570; Damodaran and Arumugam, 2011, *Redox Rep;* 16:216-222; and Yap et al., 2010, *J Proteome Res;* 9:2996-3004). Two recent reports highlight the potential use of metabolomic analysis of urine to identify signatures of ASD. One study used 1H-NMR methods and showed changes in metabolites associated with the tryptophan/nicotinic acid metabolic pathway, sulphur and amino acid pathways, as well as microbial metabolites implicating the involvement of microbial metabolism in the etiology of ASD (Yap et al., 2010, *J Proteome Res;* 9:2996-3004). Ming et al. used a combination of liquid- and gas-chromatography based mass spectrometry methods to identify changes in a number of amino acids and antioxidants such as carnosine, as well as confirming the changes associated with altered gut microbiomes (Ming et al., 2012, *J Proteome Res;* 11:5856-5862).

Measurement of metabolites offers an excellent opportunity to identify differences in small molecule abundance that may have the ability to characterize some forms of ASD. High resolution mass spectrometry (HRMS) is not only a very sensitive detection method for small molecule metabolites, it also provides accurate mass data that aids in metabolite identification through molecular formulae determination (Dunn et al., 2005, *Analyst;* 130:606-625). HRMS offers an additional distinct advantage in the ability to distinguish between compounds with the same nominal mass (isobaric compounds), providing enhanced chemical formula and structure information (Gross, 1994, *J Am Soc Mass Spectrom;* 5:57).

Unfortunately there is not one universal chromatographic mass spectrometric technique capable of detecting all of the metabolites in blood. To identify novel potential biomarkers associated with ASD, it is necessary to facilitate broad metabolite detection coverage. Toward this goal, we applied an orthogonal approach to chromatographic separation, mass spectral ionization and detection (Bruce et al., 2008, *Anal Biochem;* 372:237-249). The current study employed multiple chromatographic mass spectrometric metabolomic methods including gas chromatography-mass spectrometry (GC-MS) and liquid chromatography-high resolution mass spectrometry (LC-HRMS) to discover a wide range of metabolites in blood plasma samples that were able to differentiate TD individuals from those with ASD. Subsequently, tandem mass spectrometry (MS-MS) experiments were employed to aid in structural confirmation of the metabolites discovered by LC-HRMS.

This example performed a broad evaluation of small molecules in blood plasma to discover metabolites that may lead to biomarkers associated with ASD. Univariate, multivariate and machine learning methods were employed to determine if metabolites or groups of metabolites exhibiting statistically significant abundance differences can be used as biomarkers to distinguish children with ASD from TD individuals.

Methods

Subject Samples

The experimental subjects were initially recruited through the UC Davis M.I.N.D. Institute Clinic, Regional Centers, referrals from clinicians, area school districts and community support groups such as Families for Early Autism Treatment (FEAT), and were limited to a narrow age range of 4-6 years (see Table 1). Typically developing participants (N=30) were recruited from area school districts and community centers. All facets of the original study were approved by the University of California at Davis Institutional Review Board (IRB). Written informed consent was obtained from the parent or guardian of each participant and data were analyzed without personal information identifiers. Following informed consent, subjects completed diagnostic and psychological measures. Study participants with ASD (N=52) were enrolled under inclusion criteria consisting of a diagnosis of autism spectrum disorder based on the DSM-IV criteria determined by an experienced neuropsychologist (BAC), which was further corroborated by the following measures using research reliable clinicians: the Autism Diagnostic Observation Schedule-Generic (ADOS-G) provides observation of a child's communication, reciprocal social interaction, and stereotyped behavior including an algorithm with cutoffs for autism and autism spectrum disorders.

TABLE 1

Patient demographic information.

| Demographic | | TD | ASD | Overall |
|---|---|---|---|---|
| Group Size | | 30 | 52 | 82 |
| Sex (male %) | | 86.67 | 78.85 | 81.7 |
| Age (Years) | Range | 4.17-6.92 | 4-6.92 | 4-6.92 |
| | Average | 5.6 | 5.37 | 5.46 |
| | Std. Dev. | 0.95 | 0.81 | 0.87 |
| IQ | Range | 88-137 | 40-110 | 40-137 |
| | Average | 114.3 | 67.48 | 80 |
| | Std. Dev. | 10.78 | 17.69 | 27.47 |

The Autism Diagnostic Interview-Research (ADI-R) is a comprehensive, semi-structured parent interview that assesses a child's developmental history and relevant behaviors characteristic of ASD and generates a diagnostic algorithm for children with ASD. Based on the DSM-IV criteria (American Psychiatric Association (2013) Desk Reference to the Diagnostic Criteria from DSM-5, 5th ed. Washington, D.C.: American Psychiatric Association), only children with strictly defined autistic disorder were enrolled whereas children with pervasive developmental disorder—not otherwise specified (PDD-NOS) or Asperger Syndrome were excluded from the study. The Social Communication Questionnaire (SCQ) was used as a screening tool to ensure the absence of symptoms of ASD in the TD control children. The patients recruited for this study were primarily Caucasian and the ages were similar between groups. However, the participants with autism had lower IQ scores than the typically developing subjects (Corbett et al., 2007, *Mol Psychiatry;* 12:292-306; and Ashwood et al., 2011, *PLoS One;* 6:e19299).

The exclusion criteria for all subjects included the presence of Fragile X or other serious neurological (for example, seizures), psychiatric (for example, bipolar disorder) or known medical conditions such as autoimmune disease and inflammatory bowel diseases/celiac disease. All subjects were screened via parental interview for current and past physical illness. Children with known endocrine, cardiovascular, pulmonary, and liver or kidney disease were excluded from enrollment in the study. Dietary restriction for participation in the study was not required with the exception of an overnight fast. Participation in the study required two clinical visits for behavioral assessment and blood draws.

Regarding patient medication, 18 out of 52 of the subjects with ASD in this study were taking medications which included risperidone (5 subjects), sertraline (3 subjects), aripiprazole (2 subjects), antihistamines (2 subjects), antivirals (2 subjects), antifungals (2 subjects), and various other less frequent drugs. Three of the 30 typical subjects were taking medications, which included methylphenidate (1 subject), albuterol (1 subject) and loratadine (1 subject). Ten of the 52 ASD subjects were on a gluten and/or casein-free (GFCF) diet. Importantly, blood draws were administered prior to morning administration of any medication.

Samples were collected on Thursday morning visits to the M.I.N.D. Institute over a period of 13 months. Blood was drawn into a 9.6 mL EDTA vaccutainer tube by an experienced pediatric phlebotomist between the hours of 8 and 10 AM following an overnight fast. Tubes were immediately inverted 6 to 8 times to assure mixing with the anticoagulant and placed on ice. Immediately after serum separation and aliquoting, samples were sent on the morning of the draw via courier with a barcode label, wrapped tube cap with a strip of parafilm; bubble wrapped then set in a biohazard bag which was placed inside a carrier between coolant packs. Samples were stored at $-80°$ C. This original sample set was derived from 87 children. Upon review, 5 samples were removed after visual inspection and observation of overt hemolysis. The final 82 samples used in these studies originated from 52 children with ASD and 30 children in the TD group. The children were chosen so that the age and gender distributions were similar across the groups. There was no statistical difference in age between ASD cases and the typical developing children for the current study (Welch's t-test P=0.25).

A training set of 61 of the 82 samples was used for univariate and multivariate analysis to build the classification models. The remaining 21 samples were designated as an independent, validation test set. These 21 samples were not utilized in the selection of features or the development of the classification models and represent an independent set of samples to assess the robustness of the classification model.

Sample Preparation for LC-MS

Plasma samples were split into 50 µl aliquots and stored at $-80°$ C. prior to metabolite extraction. Samples were kept on ice during these procedures. Samples were randomized into three batches for the LC-HRMS analysis such that diagnosis, IQ, age and ethnicity were equally distributed in each batch. Small molecules were extracted from 50 µL plasma aliquots using 450 µL of 8:1 methanol:water solution at $-20°$ C. (Jiye et al., 2005, *Anal Chem;* 77:8086-8094). The extraction solution also contained internal standards. The samples were agitated for 10 minutes at 2 to 8° C. then centrifuged at 18,400×G for 20 minutes at 4° C. to remove the precipitant. The supernatant was transferred to a fresh tube and the centrifugation step was repeated to remove any residual precipitate. After the final centrifugation, 450 µL of supernatant was transferred to a fresh tube then evaporated to dryness in a SpeedVac, then resolublized in 45 L of a 50:50 mixture of 0.1% formic acid in acetonitrile: 0.1% formic acid, also containing internal standards. This solution was then transferred to a high performance liquid chromatograph (HPLC) autosampler injection vial for LC-HRMS analysis.

Mass Spectrometry

Both targeted GC-MS as well as untargeted LC-HRMS were employed for better metabolome coverage. Four untargeted LC-HRMS methods were used including C8 or HILIC chromatography coupled to electrospray ionization in both positive and negative ion polarities, resulting in 4 separate data acquisitions per sample. LC-HRMS methods were developed and tested prior to the evaluation of the clinical patient samples to optimize the breadth of coverage of small molecule metabolites.

Liquid Chromatography High Resolution Mass Spectrometry

LC-HRMS was performed using an Agilent G6540 Quadrupole Time of Flight (QTOF) LC-HRMS system consisting of an Agilent 1290 HPLC coupled to a high resolution (QTOF) mass spectrometer. Electrospray ionization (ESI) in both positive and negative ion modes was employed using a dual ESI source under high-resolution exact mass conditions. For Hydrophilic Interaction Liquid Chromatography (HILIC), a Waters Acquity ultra high performance liquid chromatography (UPLC) BEH Amide column with dimensions 2.1×150 mm, 1.7 µM particle size was used and maintained at 40° C. Data was acquired for each sample for 29 minutes at a flow rate of 0.5 mL/minute using a solvent gradient with 0.1% formic acid in water and 0.1% formic acid in acetonitrile. A 2 µL aliquot of sample was injected. For C8 chromatography, data was acquired for each sample for 50 minutes at a flow rate of 0.5 ml/minute using a gradient with 0.1% formic acid in water and 0.1% formic acid in acetonitrile. An Agilent Zorbax Eclipse Plus C8 2.1×100 mm, 1.8 µM particle size column was used and maintained at 40° C. A 2 µL aliquot of sample was injected.

Gas Chromatography—Mass Spectrometry

GC-MS analyses were performed as described in Fiehn et al. (Fiehn et al., 2008, *Plant J;* 53:691-704). GC-MS data was acquired using an Agilent 6890 gas chromatograph coupled to a LECO Pegasus IV TOF mass spectrometer. Metabolite identification was done by comparing sample data to a database of over 1,000 compounds identified by GC-MS that includes mass spectra, retention indices, structures and links to external metabolic databases.

Metabolite Chemical Structure Confirmation by LC-HRMS-MS

The chemical structures of key metabolites were further confirmed using tandem mass spectrometry (LC-HRMS-MS) methods with chromatographic conditions identical to those used for their discovery. LC-HRMS-MS analyses were performed on an Agilent QTOF mass spectrometer for patient samples and/or, reference blood samples with collision energy conditions optimized to obtain the highest quality product ion spectra. The resulting product ion spectra were then compared to MS-MS spectra available in public spectral databases such as METLIN (Smith et al., 2005 *Ther Drug Monit;* 27:747-751), MassBank (Horai et al., 2010, *J Mass Spectrom;* 45:703-714) and Stemina's own SteminaMetDB database.

Data Analysis

LC-HRMS Data Preprocessing

Raw mass spectral data total ion chromatograms and internal standard extracted ion chromatograms were initially examined for quality criteria established during method development such as abundance thresholds, retention time peak shape consistency. Data files exhibiting chromatograms that met outlier criteria were removed from further analysis. Raw data were converted to open source mzData files (Orchard et al., 2007, *Proteomics;* 7:3436-3440). Peak picking and feature creation were performed using open source software library XCMS (Smith et al., 2006, *Anal Chem;* 78:779-787) then deviations in retention times were corrected using the obiwarp algorithm (Prince and Marcotte, 2006, *Anal Chem;* 78:6140-6152) based on a non-linear clustering approach to align the LC-HRMS data. Mass features were generated using the XCMS density based grouping algorithm then, missing features were integrated based on retention time and mass range of a feature bin using iterative peak filling. A "mass feature" (also abbreviated here as "feature") is a moiety detected by the mass spectrometer that is defined by the two properties of 1) the detected mass-to-charge ratio (n/z) and 2) the chromatographic retention time.

A series of data filters were then employed to remove features exhibiting low abundance levels and those resulting from background noise, fragments and contaminants from subsequent data analyses. To reduce LC-HRMS batch variations in feature detection, the abundance values were then normalized by sample to the experiment-wide median area of spiked-in internal reference standards. The integrated areas of the normalized mass features from the GC-MS and LC-HRMS platforms were combined into a single dataset. The 4572 features for the training set of samples that passed preprocessing filters.

Training and Independent Validation Sets

The 82 patient samples (52 ASD and 30 TD samples) were split into two sets, (1) a training set of 61 samples (39 ASD and 22 TD) for identification of statistically significant features and classification modeling and (2) a 21-sample independent validation set (13 ASD and 8 TD) used to evaluate performance of the classification models. This was accomplished by randomizing the samples using the diagnosis, patient IQ, and gender these training and validations sets so that each set contained a similar proportion of factors used in randomization. The validation sample set was withheld from the univariate filtering and model development process to act as an independent external sample set to evaluate model performance.

Univariate Filtering of Mass Features

T-tests were used to reduce the overall feature set, the potential for over-fitting, and increase the biological interpretability of the predictive signature (Haury et al., 2011, *PLoS One;* 6:e28210). The integrated areas of mass features normalized to internal standards (IS) from the GC-MS and LC-HRMS platforms were combined into a single dataset. The 4572 features passing the preprocessing filters for the training set of samples were further filtered using Welch T-tests under the null hypothesis that no difference in mean integrated areas of a mass feature is present between the experimental classes, and the alternative hypothesis that there is a difference in mean integrated areas between ASD and TD training set samples to identify differential features. For each feature that exhibited a statistically significant change with an uncorrected p value<0.05, its extracted ion chromatogram (EIC) of was reviewed for consistency of integration across samples, peak shape, and a minimum peak height requirement of >3000. Features passing this EIC quality review process were then utilized in the classification modeling. False discovery rates (FDRs) were calculated using the Benjamin-Hochberg method of p-value correction (Benjamini and Hochberg, 1995, *J R Stat Soc Ser B;* 57:289-300).

Classification Modeling

Model development was performed with two primary goals: to robustly rank the importance of metabolites in discriminating ASD using a VIP (Variable Importance in the Projection) score index and to identify the minimum set of predictive metabolites needed to reach the highest levels of differentiation of the ASD and TD experimental classes. Models were created by training a Partial Least Squares Discriminant Analysis (PLS-DA) or Support Vector Machine (SVM) classifier using the entire 61-sample training set. The modeling techniques PLS-DA as well as SVM with a linear kernel (Wold, 1985, "Partial least squares," In: Kotz S, Johnson N L, editors. *Encyclopedia of statistical sciences*. New York: Wiley, Vol. 6. pp. 581-591; and Cortes and Vapnik, 1995, *Mach Learn;* 20:273-297) were both utilized to demonstrate that the molecular signature can be predictive using multiple approaches. Partial Least Squares (PLS) and SVM classification models were created using the R package Classification and Regression Training "caret" version 5.17-7 (Kuhn, 2008, *J Stat Softw;* 28:1-26). Receiver operator Curve (ROC) analysis was performed using the R package ROCR version 1.0-5 (Sing et al., 2005, *Bioinformatics;* 21:3940-3941).

A nested cross validation (CV) approach (FIG. 1) was used to meet the first objective of model development—a robust measure of feature VIP scores. Feature robustness was measured by resampling the training set 100 times using an 80:20 split into 49-sample CV training and 12-sample CV test sets. VIP scores were calculated for each of the 100 resamples and the most informative features at each resample was identified by backwards recursive feature elimination (in 20-feature steps) using on Area Under the ROC Curve (AUC). The most informative set of features was then used to predict each CV test set. The VIP scores were averaged across the 100 resamples to create the VIP index for each feature. The classification performance metrics of the CV test sets were averaged across resamples to understand potential future performance.

The second objective of the classification modeling approach was to identify the minimum number of features with the highest level of classification accuracy. This objective was met using feature subsets based on the VIP score index and evaluating the subset performance in validation test set of samples. The classification models were created using the entire 61 sample training set and by stepping through features. The feature stepping process utilized the 20 top VIP features then added the next 20 highest weighted features until all 179 features were evaluated. Performance metrics (Accuracy, Sensitivity, Specificity, and ROC analysis) based on the prediction of the 21 sample independent validation set for assessment of the molecular signature at each feature subset bin size (see Table 4).

Feature annotation (assignment of putative chemical structures) was carried out for each of the features contained within the feature set(s) that performed best in the models(s). Annotation was accomplished by comparing n/z value of each mass feature to the m/z value of common ESI adducts contained in public chemical databases and/or Stemina's internal metabolite database. The molecular formulae of the mass features with putative annotations were then input into the "Find by Formula" (FBF) algorithm in the Agilent MassHunter Qualitative Analysis software which tests whether the mass spectra for a given feature is a reasonable match with the proposed formula. In most cases, the annotations for any feature with a median FBF score of less than 70, a retention time difference greater than 35 seconds or which was present in less than 50% of the data files were not included for further analysis due to lack of confidence in the annotation.

All mass features that were annotated with chemical identities in that the measured exact mass was consistent (within 20 ppm relative mass error) with one or more chemical structures. These annotations were considered to be putative until the chemical structure of the feature was further confirmed by LC-HRMS-MS.

Features from the GC-MS analysis were identified as described by (Fiehn et al., 2008, *Plant J;* 53:691-704). This procedure uses comparison of the sample data to spectra of metabolite reference standards that had been previously acquired by the same identical GC-MS method. Therefore, the data analysis and confirmation of the metabolite chemical structures was performed by a simple comparison of the acquired patient sample data to the database. GC-MS data also contained peaks that were unidentified that showed statistically significant changes depending on sample class.

Results

The use of multiple analytical methods provided a broad coverage of the metabolome and each method contributed mass features to the model for classification of the children with ASD from the TD controls. Each method was assessed for the unique features it provided. Initially, 10187 mass features were detected by the 5 analytical platforms together. The HILIC LC-HRMS method resulted in the highest number of distinctive mass features in the models, followed by C8 LC-HRMS then GC-MS. Univariate analysis filtering was performed on 4572 features that passed the previous filters. About 60% of the LC-HRMS features were putatively annotated with a chemical structure and 8% (503) of the annotated features passed the FBF procedural criteria. Approximately 36% (142) of the targeted GC-MS features were confirmed metabolites. A breakdown of these results is contained in Table 2.

TABLE 2

A breakdown of the numbers of features resulting from filtering and annotation processes, based on molecular formula. This table also helps to illustrate the orthogonality and contribution of each of the 5 analytical platforms. Molecular formulae are being used here only to approximate the method orthogonality, since any given molecular formula may be associated with multiple chemical structures.
*These annotations were confirmed in the GCMS platform and the formula were confirmed by using the KEGG database instead of the FBF procedure used in the 4 LCMS platforms.

| Platform | Raw Features | Annotated Features | Unique Formula within a Platform | Features Passing Preprocessing Filters | Features Passing Univariate Filter |
|---|---|---|---|---|---|
| HILIC+ | 3207 | 1985 | 146 | 1527 | 40 |
| HILIC− | 1865 | 1061 | 140 | 950 | 35 |
| C8+ | 3062 | 1902 | 140 | 1096 | 42 |
| C8− | 1568 | 847 | 77 | 514 | 23 |
| GC-MS | 485 | 178* | 142* | 485 | 39 |
| Total | 10187 | 5795 | 645 | 4572 | 179 |

Data across the 61-sample training set from all analytical platforms were used to identify and robustly rank the features that could be utilized to discriminate plasma samples from children with ASD from samples from typically developing (TD) children. The univariate analysis filtering, as described above, resulted in 389 statistically significant features. An additional 210 features were removed from the analysis after EIC review, leaving 179 features that were moved forward for inclusion in classification modeling. The 179 features comprised 3% of the LC-HRMS and 8% of the GC-MS preprocessed set of features and are shown in Table 6.

Training Set Model Performance

Figure 2:
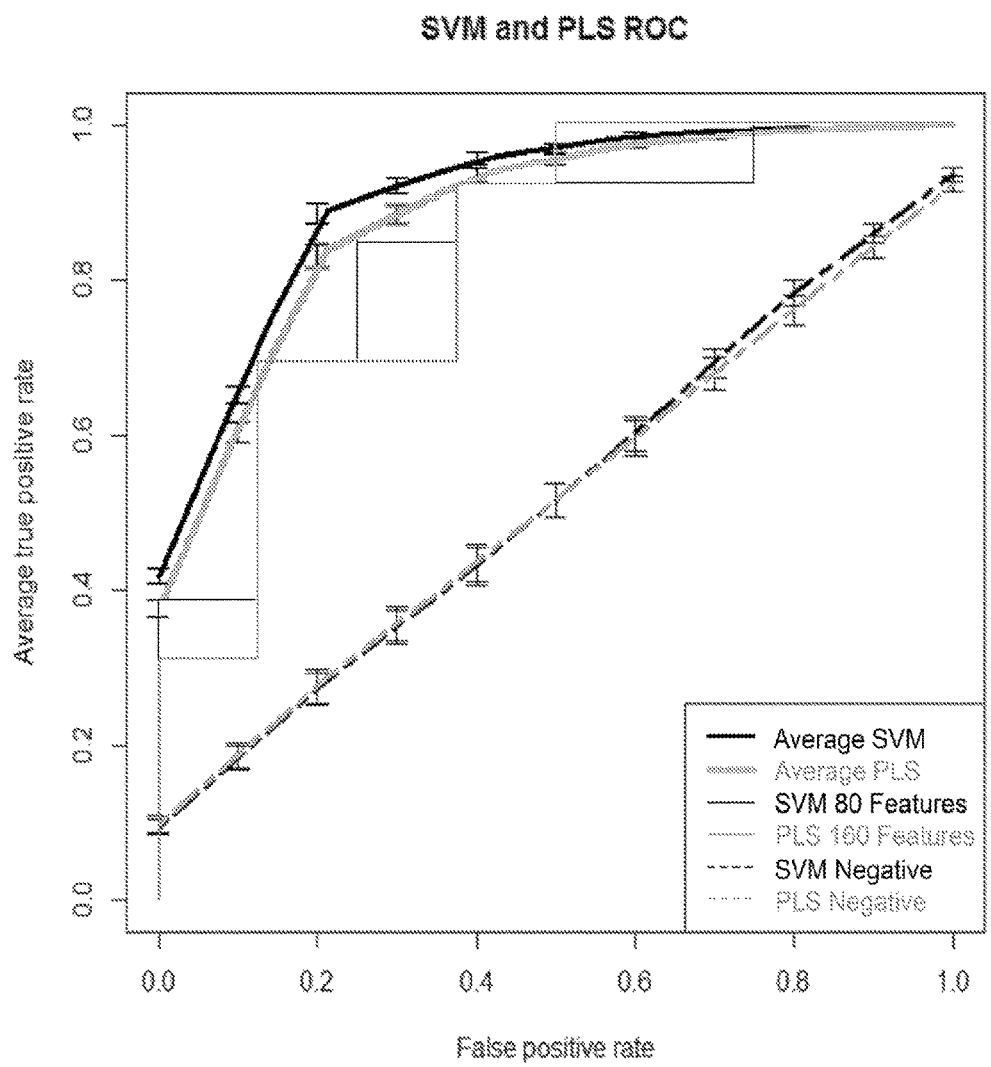
FIG. 2. Receiver operator Curve (ROC) curve performance of the classification models from the training and validation sets. The average of 100 iterations of the classifier for the best performing feature sets following recursive feature elimination comparing ASD vs. TD samples. The PLS (thin, gray) and SVM (thin, black) lines are ROC curves of the best performing validation feature subsets. Vertical bars represent the standard error of the mean.

SVM and PLS classification methods were used to discriminate between samples from children with ASD and TD children using the 179 selected features as variables and each feature's contribution toward classification was evaluated for future biomarker development efforts. Using the optimal scores from all of the 100 modeling iterations performed for each modeling method (CV Training Set), ROC plots were generated from both the training set and the independent validation test sets to understand model performance. The 100 models generated were averaged and plotted as a function of true response rate versus false positive rate. Both SVM and PLS modeling methods indicated that a metabolic signature could be detected that could classify children with ASD from TD individuals. The SVM model provided AUC values of 0.95 (95% confidence interval (CI) 0.94-0.96) and the PLS model gave AUC values of 0.92 (95% CI 0.91-0.94). To confirm that the model classification accuracies were not random results, the features were also modeled with random permutations of the group diagnosis class labels. These results showed near random classification, with AUC values between 0.52 (95% CI 0.48-0.57) and 0.52 (95% CI 0.49-0.56) for SVM and PLS, respectively, indicating that the features could not discriminate the classes using a randomized data set (FIG. 2).

Figure 3:
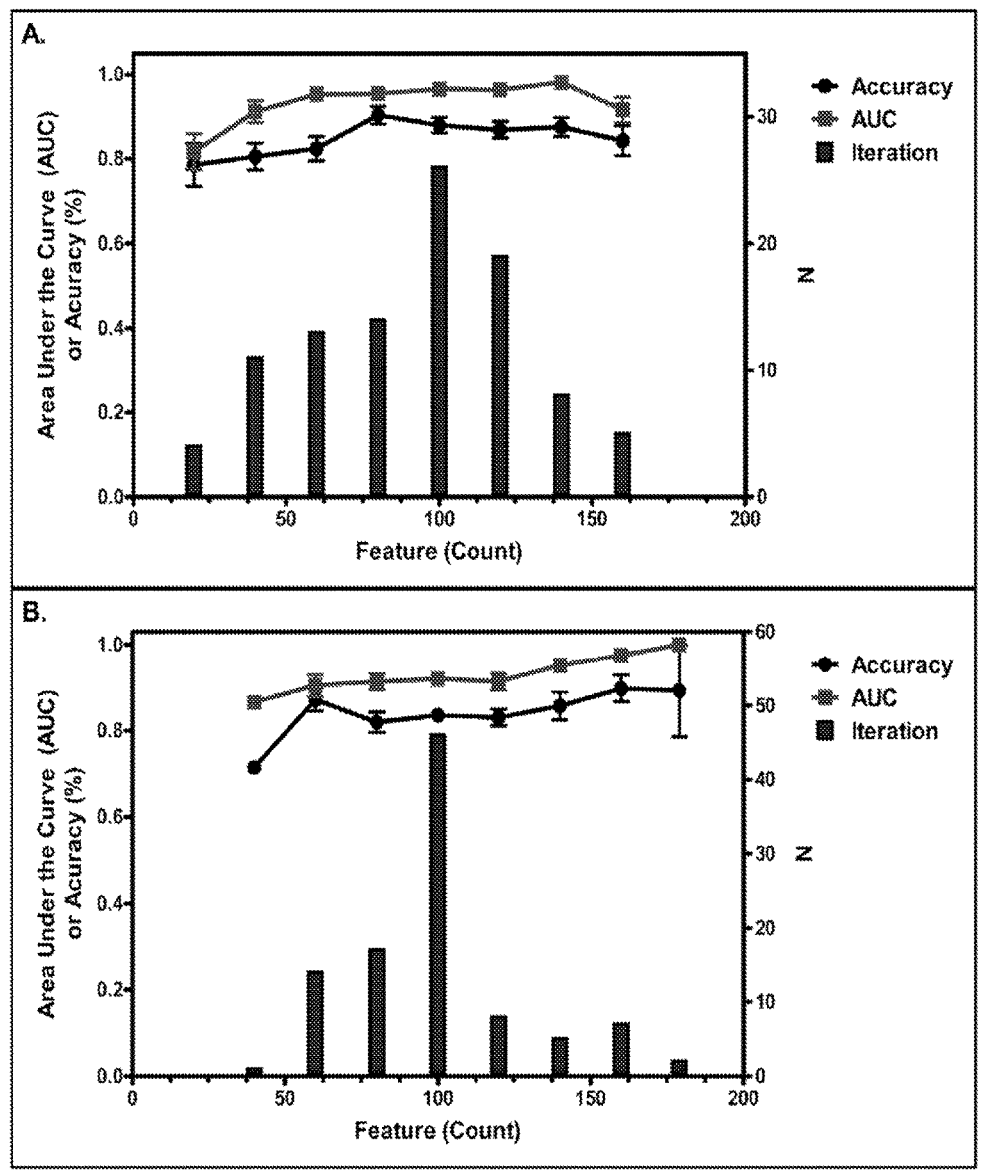
FIGS. 3A and 3B. Performance of the SVM and PLS models. Average AUC and accuracy of the SVM (FIG. 3A) and PLS (FIG. 3B) models containing different numbers of features. The bar graphs show the number of optimal models which were derived from the indicated number of features.
Figure 4:
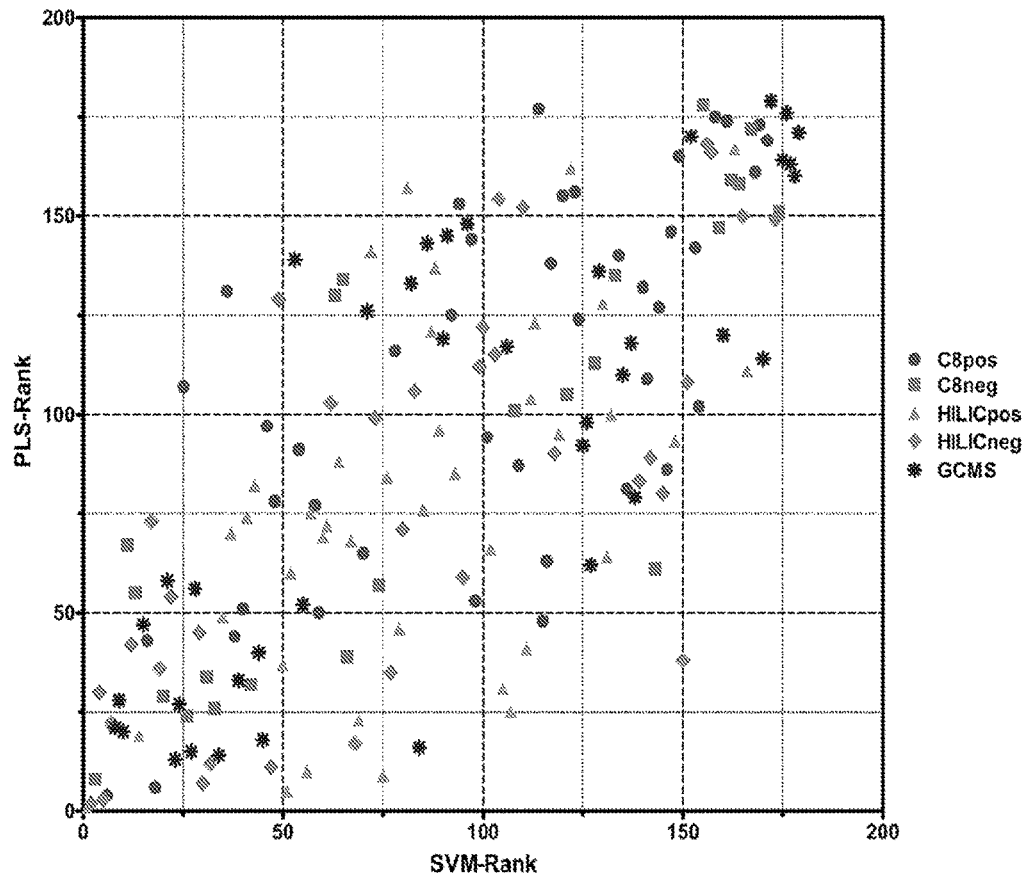
FIG. 4. Feature Importance Rankings. The top 179 features were compared for rank between SVM and PLS modeling methods. The lowest rank scores represent the most important features.

Anticipating that blood tests for ASD may be more efficient and less expensive if they measure an optimally lower number of metabolites, the classification modeling paradigm also included a feature number optimization in each model, based on the highest resulting AUC. The feature sets were evaluated with the VIP scores of individual features based on their contribution to the most predictive models (Table 4). These data together indicate that not all of the features contributed equally to the models and that the number of features could be reduced by removing those that contributed less while still retaining model accuracy and robustness. As a result, the entire set of 179 features was not required for optimal model performance for either of the modeling methods (FIG. 3). The SVM models that were trained using an 80 feature set exhibited the best combined classification performance metrics (when compared to PLS and other SVM results) with an average accuracy of 90%, an average sensitivity of 92%, an average specificity of 87%, and an average AUC of 0.95 (Table 3).

TABLE 3

Results from the cross-validation (CV) training sets showing the feature sets with the highest classification accuracy. N is the number of times the bin size performed the best in the training set with the corresponding number of features. Accuracy, sensitivity, specificity, and AUC are the averaged value of the feature bin size. Supplemental Table S2 shows the results for all feature sets.

| Model | Feature No. | N | Accuracy | Sensitivity | Specificity | AUC |
|---|---|---|---|---|---|---|
| PLS | 160 | 7 | 0.90 | 0.87 | 0.94 | 0.97 |
| SVM | 80 | 14 | 0.90 | 0.92 | 0.87 | 0.95 |

TABLE 4

Classifier performance metrics based on predictions on the independent 21-sample validation set, showing the feature sets with the highest accuracy. Feature No. corresponds to the number of the ordered, ranked VIP features that were evaluated. Supplemental Table S3 shows the results for all feature sets.

| Model | Feature No. | Accuracy | Sensitivity | Specificity | AUC |
|---|---|---|---|---|---|
| SVM | 80 | 0.81 | 0.85 | 0.75 | 0.84 |
| PLS | 160 | 0.81 | 0.92 | 0.63 | 0.81 |

Validation Set Model Performance

Different subsets of features, created based on the weighted VIP scores, were evaluated independently of the outer cross-validation loop using the 21-sample independent validation set. The 80-feature SVM model described above had a classification prediction accuracy of 81%, a sensitivity of 85%, a specificity of 75% and an AUC of 0.84 (FIG. 2, thin, black line). The best performing PLS model, comprised of 140 variables, had an accuracy of 81%, a sensitivity of 85%, a specificity of 75% and an AUC of 0.79 (FIG. 2; thin, gray line; Table 4). The results suggest that at least 40 features are needed to reach an accuracy of 70% and that a range of 80 to 160 features perform well with this independent validation data set.

Confirmation of Metabolite Chemical Structures

The chemical identities of the 7 LC-MS mass features that were confirmed by LC-HRMS-MS are shown in Table 5. Included in the metabolites confirmed by LC-HRMS-MS or targeted GC-MS was homocitrulline, which had the greatest statistical significance and the highest rank of all features in both SVM and PLS classification models in this study. Other metabolites showing significant up or down regulation include: aspartate, glutamate, dehydroepiandrosterone sulfate (DHEAS), citric acid, succinic acid, methylhexa-decanoic acid, tetra-decanoic acid, hepta-decanoic acid, isoleucine, glutaric acid, 3 aminoisobutyric acid, and creatinine. These are listed in Table 5 and represent a variety of molecular classes including amino acids, organic acids, sterols, and fatty acids.

Table 6 provides supplementary information of all 179 model features.

TABLE 5

Confirmed metabolites. Metabolites with chemical structures confirmed by LC-HRMS-MS or by GC-MS.

| Analytical Platform | Metabolite | Feature ID | HMDB ID [59] | Log2 (ASD/TD) | p-value (ASD vs. TD) | FDR | SVM Rank | PLS Rank |
|---|---|---|---|---|---|---|---|---|
| HILICpos | homocitrulline | M190T512 | HMDB00679 | −0.57 | <0.001 | 0.059 | 1 | 1 |
| C8neg | 2-hydroxyvaleric acid | M117T127 | HMDB01863 | −0.33 | 0.0289 | 0.53 | 33 | 26 |
| HILICpos | cystine | M241T774 | HMDB00192 | −0.13 | 0.0277 | 0.532 | 87 | 121 |
| GCMS | aspartic acid | GCMS_aspartic.acid | HMDB00191 | 0.41 | <0.001 | 0.086 | 34 | 14 |
| HILICpos | isoleucine | M132T248 | HMDB00172 | −0.40 | 0.0351 | 0.541 | 60 | 69 |
| HILICpos | creatinine | M114T262 | HMDB00562 | −0.18 | 0.0471 | 0.576 | 57 | 75 |
| GCMS | serine | GCMS_serine | HMDB00187 | 0.22 | 0.00275 | 0.267 | 137 | 118 |
| HILICneg | 4-hydroxyphenyllactic acid | M181T66 | HMDB00755 | −0.25 | 0.0344 | 0.541 | 47 | 11 |
| GC-MS | citric acid | GCMS_citric.acid | HMDB00094 | −0.13 | 0.0492 | 0.580 | 84 | 16 |
| GC-MS | glutamic acid | GCMS_glutamic.acid | HMDB00148 | 0.36 | 0.00144 | 0.188 | 15 | 47 |
| GC-MS | lactic acid | GCMS_indol.3.lactate | HMDB00671 | −0.20 | 0.0181 | 0.457 | 55 | 52 |
| C8neg | DHEA sulfate | M367T736 | HMDB01032 | 1.35 | 0.00152 | 0.188 | 11 | 67 |
| GC-MS | glutaric acid | GCMS_glutaric.acid | HMDB00661 | 0.44 | 0.00492 | 0.322 | 27 | 15 |
| GC-MS | 5-hydroxynorvaline | GCMS_X5.Hydroxy norvaline.NIST | HMDB31658 | 0.34 | 0.0457 | 0.576 | 177 | 163 |
| GC-MS | heptadecanoic acid | GCMS_heptadecanoic.acid.NIST | HMDB02259 | −0.31 | 0.0270 | 0.527 | 135 | 110 |
| GC-MS | 5-aminovaleric acid lactam | GCMS_X5.aminovaleric.acid.lactame | HMDB11749 | 1.28 | 0.00211 | 0.22 | 127 | 62 |
| GC-MS | succinic acid | GCMS_succinic.acid | HMDB00254 | 0.15 | 0.0457 | 0.576 | 175 | 164 |
| GG-MS | myristic acid | GCMS_myristic.acid | HMDB00806 | −0.40 | 0.00892 | 0.371 | 24 | 27 |
| GC-MS | 2-hydroxyvaleric acid | GCMS_X2.hydroxyvaleric.acid | HMDB01863 | 0.50 | 0.0406 | 0.564 | 179 | 171 |
| GC-MS | methylhexadecanoic acid | GCMS_methylhexadecanoic.acid | NA | −0.29 | 0.0399 | 0.564 | 160 | 120 |
| GC-MS | 3-aminoisobutyric acid | GCMS_X3.aminoisobutyric.acid | HMDB02166 | 0.25 | 0.0473 | 0.576 | 176 | 176 |

TABLE 6

Metabolic features used in the classification models.

| FEATURE.ID | FC | p value | FDR | SVM rank | PLS rank |
|---|---|---|---|---|---|
| HILICpos_M190T512 | −0.574294395 | 6.50E−05 | 0.058877 | 1 | 1 |
| HILICneg_M413T178 | 1.107678322 | 0.000306389 | 0.126148707 | 2 | 2 |
| C8neg_M383T543 | 1.906109679 | 1.52E−05 | 0.0344204 | 3 | 8 |
| HILICneg_M383T152 | 1.545564566 | 0.001204912 | 0.185773953 | 4 | 30 |
| HILICneg_M238T256 | 1.514299677 | 0.000149304 | 0.084524727 | 5 | 3 |
| C8pos_M356T899 | −0.537343958 | 0.004660165 | 0.319541094 | 6 | 4 |
| HILICneg_M526T303 | −0.600725412 | 0.00692685 | 0.337330147 | 7 | 22 |
| GCMS_X223597 | −0.418918276 | 4.33E−05 | 0.0516306 | 8 | 21 |
| GCMS_X693644 | −0.490633276 | 0.000131003 | 0.084524727 | 9 | 28 |
| GCMS_X223521 | −0.462404447 | 0.000677631 | 0.161525832 | 10 | 20 |
| C8neg_M367T736 | 1.345485468 | 0.001521481 | 0.188142372 | 11 | 67 |
| HILICneg_M151T65 | 1.575684512 | 0.001159 | 0.185773953 | 12 | 42 |
| C8neg_M395T896 | 0.901748936 | 0.000486227 | 0.153426385 | 13 | 55 |
| HILICpos_M548T308 | −0.716768799 | 0.000612072 | 0.161525832 | 14 | 19 |
| GCMS_glutamic.acid | 0.362717714 | 0.0014386 | 0.188142372 | 15 | 47 |
| C8pos_M211T1485 | −0.468895286 | 0.014514434 | 0.450249464 | 16 | 43 |
| HILICneg_M279T65 | −0.529975098 | 0.013693437 | 0.450249464 | 17 | 73 |
| C8pos_M330T796 | −0.526646348 | 0.008689495 | 0.367801148 | 18 | 6 |
| HILICneg_M447T64 | 1.289845187 | 4.56E−05 | 0.0516306 | 19 | 36 |
| C8neg_M181T126 | −0.339802658 | 0.030821593 | 0.532123728 | 20 | 29 |
| GCMS_X204426 | −0.3624895 | 0.04541231 | 0.575555143 | 21 | 58 |
| HILICneg_M495T64 | 0.607393566 | 0.001323022 | 0.185773953 | 22 | 54 |
| GCMS_X309540 | −0.464447081 | 0.001910193 | 0.213141589 | 23 | 13 |
| GCMS_myristic.acid | −0.397968839 | 0.008921749 | 0.370702763 | 24 | 27 |
| C8pos_M352T904 | −0.274675699 | 0.034121505 | 0.541334509 | 25 | 107 |
| C8neg_M512T1062 | −0.522436699 | 0.01308388 | 0.450249464 | 26 | 24 |
| GCMS_glutaric.acid | 0.441006305 | 0.00491769 | 0.322785768 | 27 | 15 |
| GCMS_X213253 | −0.318609139 | 0.006111376 | 0.326010174 | 28 | 56 |
| HILICneg_M544T296 | −0.383875334 | 0.023140178 | 0.509169018 | 29 | 45 |
| HILICneg_M514T118 | −0.717503186 | 0.003519318 | 0.306512617 | 30 | 7 |
| C8neg_M580T1062 | −0.553106823 | 0.015038304 | 0.455398076 | 31 | 34 |
| HILICneg_M363T117 | −0.752568195 | 0.001713805 | 0.204258496 | 32 | 12 |
| C8neg_M117T127 | −0.329612117 | 0.028909955 | 0.532123728 | 33 | 26 |
| GCMS_aspartic.acid | 0.414998766 | 0.000169944 | 0.085519597 | 34 | 14 |
| HILICpos_M150T533 | 0.371965838 | 0.004039007 | 0.307338695 | 35 | 49 |
| C8pos_M201T1299 | −0.442307309 | 0.028144878 | 0.532123728 | 36 | 131 |
| HILICpos_M671T64 | 0.611848657 | 0.001929522 | 0.213141589 | 37 | 70 |
| C8pos_M372T1041 | −0.333761235 | 0.02370961 | 0.51625396 | 38 | 44 |
| GCMS_X268083 | −0.423463755 | 0.004225759 | 0.313745287 | 39 | 33 |

TABLE 6-continued

Metabolic features used in the classification models.

| FEATURE.ID | FC | p value | FDR | SVM rank | PLS rank |
|---|---|---|---|---|---|
| C8pos_M468T1059 | −0.364427908 | 0.014680242 | 0.450249464 | 40 | 51 |
| HILICpos_M468T307 | −0.472929465 | 0.007701278 | 0.350562308 | 41 | 74 |
| C8neg_M680T1178 | −0.443495481 | 0.042825212 | 0.570406602 | 42 | 32 |
| HILICpos_M508T298 | −0.498854529 | 0.008414507 | 0.359521719 | 43 | 82 |
| GCMS_X233160 | 0.640627074 | 0.000812665 | 0.180384463 | 44 | 40 |
| GCMS_X698838 | −0.183447475 | 0.048398166 | 0.579774081 | 45 | 18 |
| C8pos_M183T1299 | −0.442000036 | 0.02517567 | 0.523186342 | 46 | 97 |
| HILICneg_M181T66 | −0.246564792 | 0.034437936 | 0.541334509 | 47 | 11 |
| C8pos_M223T1709 | 0.710198384 | 0.001537043 | 0.188142372 | 48 | 78 |
| HILICneg_M7287T413 | −0.252543749 | 0.028391725 | 0.532123728 | 49 | 129 |
| HILICpos_M346T65 | −0.753696321 | 0.044351383 | 0.57485727 | 50 | 37 |
| HILICpos_M873T405 | 0.468718461 | 0.006574659 | 0.331748696 | 51 | 5 |
| HILICpos_M175T475 | 0.565575316 | 0.016258095 | 0.457074144 | 52 | 60 |
| GCMS_X294986 | 0.510520927 | 0.036255086 | 0.544871073 | 53 | 139 |
| C8pos_M341T1299 | −0.423186625 | 0.029281886 | 0.532123728 | 54 | 91 |
| GCMS_indole.3.lactate | −0.203784132 | 0.018064975 | 0.457074144 | 55 | 52 |
| HILICpos_M464T700 | 0.381910575 | 0.010075892 | 0.40321393 | 56 | 10 |
| HILICpos_M114T262 | −0.180569242 | 0.047059654 | 0.575893992 | 57 | 75 |
| C8pos_M344T905 | −0.328022113 | 0.026453891 | 0.523186342 | 58 | 77 |
| C8pos_M3697T1485 | −0.341708984 | 0.047135734 | 0.575893992 | 59 | 50 |
| HILICpos_M132T248 | −0.403800509 | 0.035147147 | 0.541334509 | 60 | 69 |
| HILICpos_M521T65 | 0.531862981 | 0.001518851 | 0.188142372 | 61 | 72 |
| HILICneg_M502T307 | −0.484919972 | 0.034608612 | 0.541334509 | 62 | 103 |
| C8neg_M329T845 | −0.384424444 | 0.022420399 | 0.50388533 | 63 | 130 |
| HILICpos_M277T760 | 0.607928391 | 0.031162035 | 0.532123728 | 64 | 88 |
| C8neg_M369T806 | 1.052698625 | 0.020591784 | 0.484708528 | 65 | 134 |
| C8neg_M241T765 | −0.771728085 | 0.007836448 | 0.351398742 | 66 | 39 |
| HILICpos_M873T406 | −0.415668893 | 0.008043088 | 0.351449573 | 67 | 68 |
| HILICneg_M550T74 | −0.579390738 | 0.015342881 | 0.457074144 | 68 | 17 |
| HILICpos_M290T65 | −0.7261654 | 0.012969623 | 0.450249464 | 69 | 23 |
| C8pos_M131T75 | −0.376736619 | 0.02536123 | 0.523186342 | 70 | 65 |
| GCMS_X339455 | 0.193466902 | 0.012026572 | 0.450249464 | 71 | 126 |
| HILICpos_M295T760 | 0.549487987 | 0.036299861 | 0.544871073 | 72 | 141 |
| HILICneg_M825T764 | 0.436815546 | 0.01328374 | 0.450249464 | 73 | 99 |
| C8neg_M524T1171 | −0.447008938 | 0.049137377 | 0.579774081 | 74 | 57 |
| HILICpos_M849T272 | −0.591298113 | 0.028860138 | 0.532123728 | 75 | 9 |
| HILICpos_M471T65 | 0.675542835 | 0.002007717 | 0.216498817 | 76 | 84 |
| HILICneg_M732T346 | −0.353703608 | 0.048614774 | 0.579774081 | 77 | 35 |
| C8pos_M206T48 | −0.316315016 | 0.016943497 | 0.457074144 | 78 | 116 |
| HILICpos_M328T64 | −0.5161768 | 0.040438768 | 0.563740405 | 79 | 46 |
| HILICneg_M318T67 | 0.506598493 | 0.003135662 | 0.289824759 | 80 | 71 |
| HILICpos_M763T105 | 2.015769538 | 0.015692531 | 0.457074144 | 81 | 157 |
| GCMS_X200905 | 0.191496474 | 0.013021042 | 0.450249464 | 82 | 133 |
| HILICneg_M269T422 | 0.260928822 | 0.029710631 | 0.532123728 | 83 | 106 |
| GCMS_citric.acid | −0.129245802 | 0.04920581 | 0.579774081 | 84 | 16 |
| HILICpos_M328T426 | −0.433938776 | 0.014025888 | 0.450249464 | 85 | 76 |
| GCMS_X425495 | 0.41187022 | 0.041963199 | 0.570406602 | 86 | 143 |
| HILICpos_M241T774 | −0.133041838 | 0.027698614 | 0.532123728 | 87 | 121 |
| HILICpos_M390T65 | −0.402496331 | 0.048036569 | 0.579774081 | 88 | 137 |
| HILICpos_M86T248 | −0.380000043 | 0.031621418 | 0.532123728 | 89 | 96 |
| GCMS_X202681 | 0.368840704 | 0.010149346 | 0.40321393 | 90 | 119 |
| GCMS_X237799 | 0.532509177 | 0.00806289 | 0.351449573 | 91 | 145 |
| C8pos_M1130T967_2 | 0.311891453 | 0.042327868 | 0.570406602 | 92 | 125 |
| HILICpos_M490T307 | −0.378543083 | 0.026872403 | 0.5276391 | 93 | 85 |
| C8pos_M295T842 | −0.302349228 | 0.031372957 | 0.532123728 | 94 | 153 |
| HILICneg_M556T294 | 0.456952429 | 0.007402468 | 0.345626573 | 95 | 59 |
| GCMS_X285338 | 0.529051838 | 0.008348077 | 0.359521719 | 96 | 148 |
| C8pos_M269T936 | 0.297961296 | 0.044187761 | 0.57485727 | 97 | 144 |
| C8pos_M504T1130 | −0.501779408 | 0.025239235 | 0.523186342 | 98 | 53 |
| HILICneg_M127T101 | −0.377288743 | 0.042105075 | 0.570406602 | 99 | 112 |
| HILICneg_M174T58 | −0.310035741 | 0.044723792 | 0.57485727 | 100 | 122 |
| C8pos_M1126T979_4 | 0.336493611 | 0.006592489 | 0.331748696 | 101 | 94 |
| HILICpos_M1679T290 | −0.400321526 | 0.007082646 | 0.341247912 | 102 | 66 |
| HILICneg_M204T65_2 | −0.205412524 | 0.032099006 | 0.532123728 | 103 | 115 |
| HILICneg_M496T416 | 0.246550483 | 0.021537899 | 0.496847002 | 104 | 154 |
| HILICpos_M945T171 | −0.694456956 | 0.023213348 | 0.509169018 | 105 | 31 |
| GCMS_X208557 | −0.48618147 | 0.023070139 | 0.509169018 | 106 | 117 |
| HILICpos_M486T64 | −0.333084126 | 0.016410405 | 0.457074144 | 107 | 25 |
| C8neg_M337T656 | 0.66173541 | 0.001342588 | 0.185773953 | 108 | 101 |
| C8pos_M595T1801 | 0.784588835 | 0.003631332 | 0.307338695 | 109 | 87 |
| HILICneg_M267T64 | 0.280103928 | 0.043580931 | 0.570406602 | 110 | 152 |
| HILICpos_M474T414_2 | −0.336031825 | 0.027524674 | 0.532123728 | 111 | 41 |
| HILICpos_M558T288 | −0.298044087 | 0.018031652 | 0.457074144 | 112 | 104 |
| HILICpos_M270T95 | 0.944788491 | 0.005622595 | 0.326010174 | 113 | 123 |
| C8pos_M1071T1248 | 0.569224393 | 0.036773716 | 0.54605954 | 114 | 177 |
| C8pos_M227T1367 | −0.517028459 | 0.016848111 | 0.457074144 | 115 | 48 |

TABLE 6-continued

Metabolic features used in the classification models.

| FEATURE.ID | FC | p value | FDR | SVM rank | PLS rank |
|---|---|---|---|---|---|
| C8pos_M229T1485 | −0.418462585 | 0.03805523 | 0.554186935 | 116 | 63 |
| C8pos_M251T935 | 0.265455182 | 0.048768627 | 0.579774081 | 117 | 138 |
| HILICneg_M73T67 | 0.326189387 | 0.005145869 | 0.323689454 | 118 | 90 |
| HILICpos_M381T414 | 0.21045061 | 0.037411169 | 0.549411091 | 119 | 95 |
| C8pos_M1001T979_3 | 0.301770134 | 0.036532009 | 0.544871073 | 120 | 155 |
| C8neg_M311T1209 | −0.531893373 | 0.047217285 | 0.575893992 | 121 | 105 |
| HILICpos_M594T65 | 0.605783038 | 0.03498926 | 0.541334509 | 122 | 162 |
| C8pos_M286T910 | 1.813765734 | 0.014069447 | 0.450249464 | 123 | 156 |
| C8pos_M1001T979_2 | 0.350307878 | 0.014300976 | 0.450249464 | 124 | 124 |
| GCMS_X470909 | 0.318129031 | 0.028586421 | 0.532123728 | 125 | 92 |
| GCMS_X445906 | 0.291632714 | 0.018810455 | 0.467671816 | 126 | 98 |
| GCMS_X5.aminovaleric.acid.lactame | 1.2786866 | 0.002106809 | 0.221900883 | 127 | 62 |
| C8neg_M453T1277 | 0.624873146 | 0.021500832 | 0.496847002 | 128 | 113 |
| GCMS_X199802 | 0.361361333 | 0.027290638 | 0.530469097 | 129 | 136 |
| HILICpos_M185T98 | 0.374182075 | 0.032571754 | 0.532123728 | 130 | 128 |
| HILICpos_M530T298 | −0.493681111 | 0.032457099 | 0.532123728 | 131 | 64 |
| HILICpos_M129T414 | −0.34306608 | 0.015370168 | 0.457074144 | 132 | 100 |
| C8neg_M1039T75 | 0.415375478 | 0.034607409 | 0.541334509 | 133 | 135 |
| C8pos_M300T801 | 0.27128485 | 0.043073093 | 0.570406602 | 134 | 140 |
| GCMS_heptadecanoic.acid.NIST | −0.30737434 | 0.027028543 | 0.5276391 | 135 | 110 |
| C8pos_M181T112 | 1.956197149 | 0.000996772 | 0.185773953 | 136 | 81 |
| GCMS_serine | 0.221379646 | 0.002752061 | 0.267052774 | 137 | 118 |
| GCMS_X218839 | 0.435697244 | 0.015082736 | 0.455398076 | 138 | 79 |
| HILICneg_M334T415 | 0.317010358 | 0.013152756 | 0.450249464 | 139 | 83 |
| C8pos_M998T974_3 | 0.27754853 | 0.025632082 | 0.523186342 | 140 | 132 |
| C8pos_M1123T974_2 | 0.321877985 | 0.035379778 | 0.541334509 | 141 | 109 |
| HILICneg_M117T67 | 0.337299144 | 0.005985641 | 0.326010174 | 142 | 89 |
| C8neg_M303T1597 | −0.738181929 | 0.046948765 | 0.575893992 | 143 | 61 |
| C8pos_M522T1224 | 0.247931369 | 0.04587253 | 0.575555143 | 144 | 127 |
| HILICneg_M640T295 | 0.405353741 | 0.031355798 | 0.532123728 | 145 | 80 |
| C8pos_M595T1829 | 0.744572146 | 0.005608327 | 0.326010174 | 146 | 86 |
| C8pos_M2237T654 | 0.43734315 | 0.02247402 | 0.50388533 | 147 | 146 |
| HILICpos_M330T66 | 0.458066037 | 0.008070381 | 0.351449573 | 148 | 93 |
| C8pos_M357T1063 | 0.713531183 | 0.038393615 | 0.555542116 | 149 | 165 |
| HILICneg_M229T265 | −0.455668048 | 0.03256453 | 0.532123728 | 150 | 38 |
| HILICneg_M223T66 | 0.831910698 | 0.00584487 | 0.326010174 | 151 | 108 |
| GCMS_X226908 | 0.394498037 | 0.046397709 | 0.575893992 | 152 | 170 |
| C8pos_M308T909 | 1.573072007 | 0.027006037 | 0.5276391 | 153 | 142 |
| C8pos_M530T1273 | 0.470742538 | 0.019608746 | 0.477462423 | 154 | 102 |
| C8neg_M462T541 | 1.609500966 | 0.031136443 | 0.532123728 | 155 | 178 |
| HILICneg_M187T130 | 0.462864731 | 0.043703045 | 0.570406602 | 156 | 168 |
| HILICneg_M369T65 | 0.360434738 | 0.042832506 | 0.570406602 | 157 | 166 |
| C8pos_M522T1248_2 | 0.352199506 | 0.040613754 | 0.563740405 | 158 | 175 |
| C8neg_M201T540 | −0.462316603 | 0.030495675 | 0.532123728 | 159 | 147 |
| GCMS_methylhexadecanoic.acid | −0.289244684 | 0.039870602 | 0.563740405 | 160 | 120 |
| C8pos_M464T538 | 1.450346822 | 0.039541227 | 0.563151626 | 161 | 174 |
| C8neg_M437T1066 | 0.762176096 | 0.035659118 | 0.543771533 | 162 | 159 |
| HILICpos_M567T65 | 0.355470678 | 0.025579731 | 0.523186342 | 163 | 167 |
| C8neg_M118T75 | 0.392787495 | 0.045715554 | 0.575555143 | 164 | 158 |
| HILICneg_M463T66 | 0.859469342 | 0.010803174 | 0.418184402 | 165 | 150 |
| HILICpos_M766T271 | 0.560594828 | 0.040954447 | 0.565496008 | 166 | 111 |
| C8neg_M463T1076 | 0.768616713 | 0.016963396 | 0.457074144 | 167 | 172 |
| C8pos_M207T106 | 0.21917152 | 0.046128622 | 0.575893992 | 168 | 161 |
| C8pos_M621T1248 | 0.238013685 | 0.038935656 | 0.559662088 | 169 | 173 |
| GCMS_X616746 | −0.187096114 | 0.049130936 | 0.579774081 | 170 | 114 |
| C8pos_M1044T1248 | 0.390078003 | 0.049582099 | 0.579774081 | 171 | 169 |
| GCMS_X407371 | 0.275023999 | 0.032319676 | 0.532123728 | 172 | 179 |
| HILICneg_M259T782 | 0.286454425 | 0.049887676 | 0.579774081 | 173 | 149 |
| C8neg_M499T823 | 0.586972189 | 0.020539391 | 0.484708528 | 174 | 151 |
| GCMS_succinic.acid | 0.152656686 | 0.045686793 | 0.575555143 | 175 | 164 |
| GCMS_X3.aminoisobutyric.acid | 0.245250518 | 0.047282867 | 0.575893992 | 176 | 176 |
| GCMS_X5.hydroxynorvaline.NIST | 0.338339404 | 0.045670716 | 0.575555143 | 177 | 163 |
| GCMS_X302365.similar.to.beta.alanine.minor | 0.343275026 | 0.040702829 | 0.563740405 | 178 | 160 |
| GCMS_X2.hydroxyvaleric.acid | 0.497484089 | 0.040571309 | 0.563740405 | 179 | 171 |

Table 7 is a table of the results from the cross-validation (CV) training sets. N is the number of times the bin size performed the best in the training set with the corresponding number of features. Accuracy, sensitivity, specificity, and AUC are the averaged value of the feature bin size.

TABLE 7

Results from the cross-validation (CV) training sets. N is the number of times the bin size performed the best in the training set with the corresponding number of features. Accuracy, sensitivity, specificity, and AUC are the averaged value of the feature bin size.

| Feature No. | N | Accuracy | Sensitivity | Specificity | AUC |
|---|---|---|---|---|---|
| PLS Training Set Results | | | | | |
| 40 | 1 | 0.71 | 0.56 | 1.00 | 0.87 |
| 60 | 14 | 0.87 | 0.91 | 0.80 | 0.90 |
| 80 | 17 | 0.82 | 0.85 | 0.76 | 0.91 |
| 100 | 46 | 0.84 | 0.87 | 0.77 | 0.92 |
| 120 | 8 | 0.83 | 0.82 | 0.85 | 0.91 |
| 140 | 5 | 0.86 | 0.93 | 0.72 | 0.95 |
| 160 | 7 | 0.90 | 0.87 | 0.94 | 0.97 |
| 179 | 2 | 0.89 | 0.83 | 1.00 | 1.00 |
| Average | | 0.84 | 0.87 | 0.79 | 0.92 |
| SVM Training Set Results | | | | | |
| 20 | 4 | 0.79 | 0.86 | 0.65 | 0.82 |
| 40 | 11 | 0.81 | 0.82 | 0.78 | 0.91 |
| 60 | 13 | 0.82 | 0.88 | 0.72 | 0.95 |
| 80 | 14 | 0.90 | 0.92 | 0.87 | 0.95 |
| 100 | 26 | 0.88 | 0.91 | 0.83 | 0.96 |
| 120 | 19 | 0.87 | 0.89 | 0.83 | 0.96 |
| 140 | 8 | 0.88 | 0.89 | 0.85 | 0.98 |
| 160 | 5 | 0.84 | 0.89 | 0.76 | 0.92 |
| Average | | 0.86 | 0.89 | 0.81 | 0.95 |

Table 8 is a table showing classifier performance metrics based on predictions on the independent 21-sample validation set. Classifier performance metrics based on predictions on the independent 21-sample validation set. Feature No. corresponds to the number of the ordered, ranked VIP features that were evaluated.

TABLE 8

Classifier performance metrics based on predictions on the independent 21-sample validation set. Feature No. corresponds to the number of the ordered, ranked VIP features that were evaluated.

| Feature No. | Accuracy | Sensitivity | Specificity | AUC |
|---|---|---|---|---|
| SVM Validation Set Results | | | | |
| 20 | 0.57 | 0.77 | 0.25 | 0.61 |
| 40 | 0.67 | 0.85 | 0.38 | 0.58 |
| 60 | 0.76 | 0.85 | 0.63 | 0.86 |
| 80 | 0.81 | 0.85 | 0.75 | 0.84 |
| 100 | 0.71 | 0.77 | 0.63 | 0.84 |
| 120 | 0.76 | 0.85 | 0.63 | 0.85 |
| 140 | 0.76 | 0.85 | 0.63 | 0.81 |
| 160 | 0.81 | 0.92 | 0.63 | 0.83 |
| 179 | 0.76 | 0.85 | 0.63 | 0.83 |
| PLS Validation Set Results | | | | |
| 20 | 0.57 | 0.62 | 0.5 | 0.58 |
| 40 | 0.71 | 0.77 | 0.63 | 0.68 |
| 60 | 0.71 | 0.69 | 0.75 | 0.71 |
| 80 | 0.76 | 0.77 | 0.75 | 0.71 |
| 100 | 0.71 | 0.69 | 0.75 | 0.73 |
| 120 | 0.76 | 0.85 | 0.63 | 0.8 |
| 140 | 0.81 | 0.85 | 0.75 | 0.79 |
| 160 | 0.81 | 0.92 | 0.63 | 0.81 |
| 179 | 0.71 | 0.85 | 0.5 | 0.78 |

Discussion

The untargeted metabolomic approach described in this example did not possess bias toward possible pathways other than the separation and detection limits of the analytical methods used. This approach has resulted in the discovery of a biochemically diverse set of metabolites that might be useful in distinguishing individuals at risk for ASD.

Identification of Metabolites Previously Associated with ASD

Examples of metabolites showing significant up or down regulation in our study that have been previously associated with autism include:

Tricarboxylic acid cycle associated molecules including citric acid (decreased) and succinic acid (increased) were found to be significantly altered in the ASD participants. Elevations in urinary succinate (Yap et al., 2010, *J Proteome Res;* 9:2996-3004; and Ming et al., 2012, *J Proteome Res;* 11:5856-5862) and decreased urinary citrate (Frye et al., 2013, *Transl Psychiatry;* 3:e220) in children with autism have been reported by others;

Fatty acids have previously been observed to be decreased in the plasma of children with ASD, similar to our observations for methylhexa-, tetra- and hepta-decanoic acids (El-Ansary et al., 2011, *Lipids Health Dis;* 10:62). Links between saturated fatty acid metabolism and oxidative stress have been reported in erythrocytes in children with ASD (Ghezzo et al., 2013, *PLoS One;* 8:e66418);

3 aminoisobutyric acid was increased in samples from participants with ASD. This is also consistent with previous findings (Adams et al., 2011, *Nutr Metab (Lond);* 8:34); and Creatinine was decreased in children with ASD and is consistent with the findings of Whitely et al., observing similar changes in urinary creatinine in children diagnosed with PDD (Whiteley et al., 2006, *Pediatr Int;* 48:292-297).

Evidence for a Role in Mitochondrial Dysfunction in ASD

Many of the confirmed metabolites are directly associated both with ASD and with aspects of mitochondrial biology. Mitochondrial disease or dysfunction has been proposed to be potentially involved in autism (Marazziti et al., 2012, *Eur Rev Med Pharmacol Sci;* 16:270-275). In addition, several metabolites are associated with other processes already proposed to be involved in ASD including oxidative stress (Rossignol and Frye, 2012, *Mol Psychiatry;* 17:389-401) and energy production (Blaylock, 2009, *Altern Ther Health Med;* 15:60-67).

Aspartate and glutamate levels in blood were significantly elevated, as has been observed in previous ASD studies (Shinohe et al., 2006, *Prog Neuropsychopharmacol Biol Psychiatry;* 30:1472-1477; and Moreno-Fuenmayor et al., 1996, *Invest Clin;* 37:113-128). Mutations in the aspartate/glutamate mitochondrial transporter, SLC25A12, have been previously associated with ASD. This transporter is an important component of the malate/aspartate shuttle, a crucial system supporting oxidative phosphorylation, adenosine triphosphate production, and key metabolites for the urea cycle (Napolioni et al., 2011, *Mol Neurobiol;* 44:83-92).

DHEAS, the predominant plasma sterol, was found to be increased in children with ASD. DHEA is known to affect mitochondrial energy production through inhibition of enzymes associated with the respiratory chain (Safiulina et al., 2006. *Toxicol Sci;* 93:348-356) with variable findings in children with ASD (Strous et al., 2005, *Eur Neuropsychopharmacol;* 15:305-309; and Tordjman et al., 1995, *J Autism Dev Disord;* 25:295-304).

The branched chain amino acid isoleucine was reduced in samples from children with ASD versus TD children. This has also been observed by others (Arnold et al., 2003, *J Autism Dev Disord;* 33:449-454). Possible molecular mechanisms would include mutation in the branched chain amino acid kinase dehydrogenase (BCKD-kinase), a mitochondrial enzyme (Novarino et al., 2012, *Science;* 338:394-397) as well as a role for these amino acids in energy metabolism (Valerio et al., 2011, *Aging* (Albany N.Y.); 3:464-478).

Glutaric acid levels were elevated. Increased urinary glutaric acid occurs in a variety of neuronal deficiencies such as glutaryl-CoA dehydrogenase (GCDH) deficiency. A significant portion of the glutaric acid metabolism takes place in the mitochondria (Miller and Kölker, 2004, *J Inherit Metab Dis;* 27:903-910).

The Potential Relationship of the Gut Microbiome with ASD

This potential connection between the gut microbiome and ASD is also receiving considerable attention (Mulle et al., 2013. *Curr Psychiatry Rep;* 15:337). Metabolomic studies of urine from individuals with ASD have identified molecules such as dimethylamine, hippurate or phenylacetylglutamine that have been associated with the microbiome (Yap et al., 2010, *J Proteome Res;* 9:2996-3004; and Ming et al., 2012, *J Proteome Res;* 11:5856-5862). In this study, decreased plasma levels of p-hydroxyphenyllactate were observed. p-hydroxyphenyllactate is a metabolite associated with bifidobacteria and lactobacilli that is known to serve as an antioxidant both in the circulation and tissues (Beloborodova et al., 2012, *J Biomed Sci;* 19:89).

In addition, levels of aspartate, citrate, creatinine, DHEA-S, hydroxyphenyllactate, indoleacetate, isoleucine glutamate and glutarate were all found to have significant changes distinguishing between ASD and TD individuals, whereas in previous studies of urine metabolites, changes in these compounds were not significant (Ming et al., 2012, *J Proteome Res;* 11:5856-5862).

Identification of Previously Unidentified Metabolic Alterations in ASD

This study has also identified new, previously undescribed potential ASD biomarkers such as homocitrulline, which had the greatest statistical significance and the highest rank of all features in both SVM and PLS classification models. Homocitrulline is a poorly understood molecule which is known to be formed inside the mitochondria from lysine and carbamoyl phosphate. Homocitrullinuria (HHH) syndrome patients, with a urea cycle deficiency related to ornithine translocase (SLC25A15) deficiency, have higher urinary homocitrulline levels, and can exhibit behavioral abnormalities similar to ASD such as developmental delay, ataxia, spasticity, learning disabilities, cognitive deficits and/or unexplained seizures (Palmieri, 2004, *Pflugers Arch;* 447: 689-709). From these data it is plausible to suggest that changes in the urea cycle function may be related to the decreases in homocitrulline we observed in plasma.

Physicians and clinicians with specialized training are currently able to diagnose children with ASD by two years of age using behavioral characteristics. It is increasingly recognized, however, that detection of ASD at an earlier age results in better patient and family outcomes (Payakachat et al., 2012, *Expert Rev Pharmacoecon Outcomes Res;* 12:485-503; and Thompson, 2013, *J Appl Res Intellect Disabil;* 26:81-107). Therefore, a biologically-based blood test for ASD that can be administered at an early age would be highly beneficial to patients, families and medical providers. The current study profiled metabolites in blood plasma to evaluate the possibility that differences in the abundance of identified metabolites might provide a signature that could prove useful in distinguishing individuals at high risk for developing ASD. The cohort of subjects enrolled in this study was carefully assembled to reflect a diagnosis of ASD by strict research criteria. Beyond careful clinical diagnosis, great pains were taken to insure that fasting blood collection was obtained at the same time for all study participants and that complicating factors such as illness were minimized.

Metabolomics determines changes in small molecule metabolites that are reactants and products of endogenous biochemical processes as well as small molecules derived from diet, the gut microbiome and contact with the environment. Perturbations in their abundance can result not only from genomic and proteomic influences, but environmental and epigenetic influences as well. A metabolomic approach may therefore provide enhanced predictive results by keying in on common, end stage metabolites rather than on specific genomic or proteomic determinants. Since no single analytical method is capable of assessing all metabolites, we optimized and employed chromatographic methods linked to multiple mass spectrometric ionization methods that separate and detect molecules based on different chemical properties. Each of these methods provided features used by the classification models in our study.

Two independent statistical classification methods (PLS and SVM) were employed to determine the most influential metabolites and mass features that could be used to discriminate between ASD and TD individuals. Both classification modeling methods yielded relatively similar results with respect to maximum prediction accuracy of about 81% as evaluated by an independent validation sample set. Having established that predictive classification models could be obtained, we then used the recursive feature elimination approach to establish the minimal numbers of features needed for a predictive model. Interestingly, several of the key features for classification were common between the two methods indicating their importance in the development of future blood based diagnostics.

Conclusions

This example demonstrates that a profile of altered metabolites in the blood plasma of children can be detected by the combination of several MS-based metabolomic analyses. Statistical models developed from the derived metabolic data distinguished children with ASD from TD individuals with accuracy better than 80%. The study used a well curated set of samples from clinically diagnosed children with ASD and typically developing individuals between 4 and 6 years of age. Further research is being carried out to confirm the chemical structures of more of the discovered metabolites and to determine which are the most robust for determining ASD risk by evaluating them in larger and younger patient populations.

Example 2

Additional Confirmed Metabolites

Using the procedures described in more detail in Example 1, a second set of ASD samples (the MIND2 study) was assayed. This study population included samples from 180 typical (69% male; average age 3.1 years; developmental status 106) and 93 autistic subjects (83% male; average age 3 years; developmental status 62). The dietary status of all subjects when samples were taken was fed. Citrate was used as an anticoagulant.

The additional metabolites listed in Table 9 below exhibit a statistically significant difference between autistic and non-autistic individuals have been confirmed. Briefly, for sample preparation and mass spectrometry: small molecules were extracted using 8:1 methanol:water solution at −20° C.; samples were centrifuged to remove precipitate, evaporated to dryness then solubilized for LC-HRMS analysis; targeted GC-MS and untargeted LC-HRMS (C8 or HILIC chromatography) methods were optimized for metabolome coverage. LC-HRMS was performed using an Agilent G6540 QTOF LC-HRMS system; and electrospray ionization (ESI) in both positive and negative ion modes under high resolution exact mass conditions; and GC-MS data was acquired using an Agilent 6890 gas chromatograph coupled to a LECO Pegasus IV TOF MS.

A comparison of the metabolic features identified in the present example with those identified in Example 1 shows the identification of DHEAS, lysophospholipids, oxidized fatty acids, isoleucine, succinic acid, and cysteine as associated with ASD in both studies.

Using the non-targeted, MS-based metabolomic analysis of blood plasma, as described in more detail Example 1, a larger set of patients will be studied to identify and validate biomarkers for diagnostic tests to detect ASD earlier and improve patient outcomes. The biomarkers will be used to gain new insight into biochemical mechanisms involved in metabolic subtypes of ASD.

The biomarkers described herein will be used to as biomolecular targets will for the identification of new modes of therapy, and will be used to obtain insights into personalized treatment recommendations.

TABLE 9

Additional Confirmed Metabolites

| Metabolite | Method |
| --- | --- |
| 2-Aminooctanoic acid | C8pos |
| Acesulfame | C8neg |
| ADMA | HILICpos |
| Choline | C8pos |
| CMPF | C8neg |
| Cysteine | HILICpos |
| Cystine | HILICpos |
| DHEA sulfate (DHEAS) | C8neg |
| Glycine | HILICpos |
| Glycocholic Acid | C8neg |
| Hypoxanthine | HILICpos |
| Indoleacrylic acid | C8neg |
| Indoxyl sulfate | HILICneg |
| LysoPC(16:1(9Z)) | HILICpos |
| LysoPE(0:0/18:1(9Z)) | C8neg |
| LysoPE(22:6(4Z,7Z,10Z,13Z,16Z,19Z)/0:0) | C8neg |
| LysoPE(22:6(4Z,7Z,10Z,13Z,16Z,19Z)/0:0) | C8pos |
| Methionine | C8pos |
| p-cresol sulfate | C8neg |
| Phenylalanine | C8pos |
| Phenyllactic acid | C8neg |
| Proline | C8pos |
| Serotonin | HILICpos |
| Tryptophan | HILICpos |
| Uric Acid | HILICpos |
| Valine | C8pos |

Example 3

Metabolic Signatures for High Functioning Autism and Low Functioning Autism

As described in more detail in Example 1, using a number of supervised and unsupervised statistical methods, a metabolic signature that was highly predictive of ASD was identified. In samples from a population of 70 patients with ASD and 30 typically developing age-matched controls, the samples Model Accuracy Sensitivity Specificity were divided into High Functioning Autism (HFA) (IQ>70; n=33), Low Functioning Autism (LFA) (IQ<70, n=36), and Typically developing (TD) children (n=34) with an age range of 4-6 years (average 5.4 years).

Briefly, for this our analysis, 80% of the samples were included as a model training set, with the remaining 20% reserved for the blinded test set. Samples were analyzed using 5 different chromatographic-mass spectrometry based methods designed to orthogonally measure a broad range of small molecules that can ultimately be associated with metabolites and biomarkers. The top 266 statistically significant unique metabolic features were used to develop classification models that were evaluated relative to the test set. The models evaluate the predictive capacity of metabolic signatures to discriminate between individuals with autism and typical individuals, LFA and typical individuals, and HFA and typical individuals (Table 10).

TABLE 10

Performance of the classification models as evaluated on the test set. Autism predictivity results.

| Model | Accuracy | Sensitivity | Specificity |
| --- | --- | --- | --- |
| Autistic vs. Typical | 0.81 | 0.84 | 0.75 |
| LFA vs. Typical | 0.87 | 0.71 | 1.00 |
| HFA vs. Typical | 0.71 | 0.66 | 0.75 |

Figure 5:
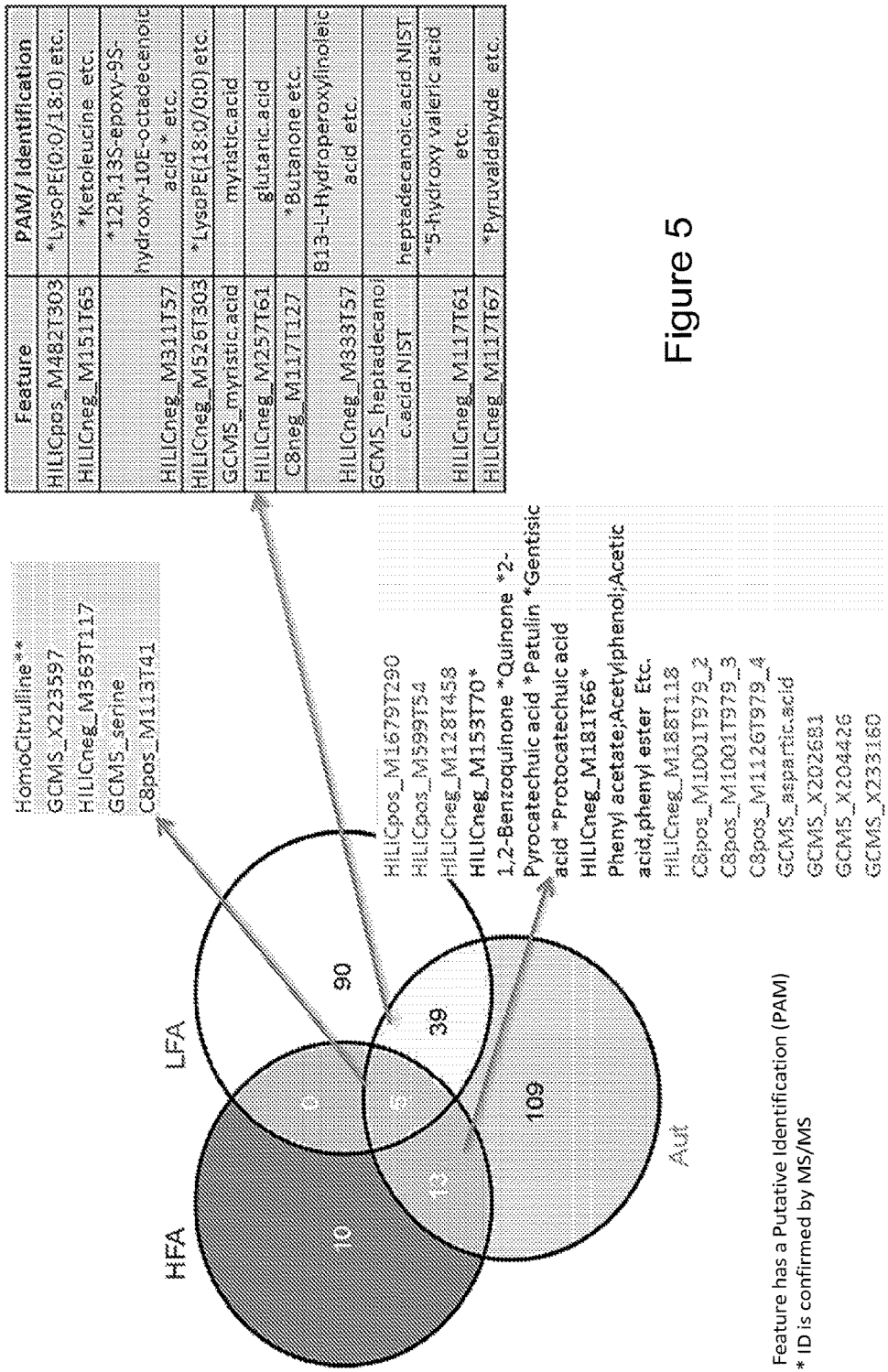
FIG. 5. Feature overlap between High Functioning Autism (HFA) and Low Functioning Autism (LFA) populations, Autism (Aut) and HFA populations, and Autism and LFA populations. * Feature has a Putative Identification (PAM). ** ID is confirmed by MS/MS.

FIG. 5 shows the overlap of biometabolic signatures between High Functioning Autism (HFA) and Low Functioning Autism (LFA) populations, Autism (Aut) and HFA populations, and Autism and LFA populations.

For 11 of the 39 features of the overlap of LFA with Aut shown in FIG. 5, additional putative identifications (PAMs) include:

HILICneg_M526T303: LysoPE(18:0/0:0), GPEtn(18:0/0:0), and LysoPE(0:0/18:0).

HILICneg_M151T65: 2-Hydroxyethyl methacrylate, HEMA 3-Oxohexanoic acid; 3-Oxohexanoate, 3-Oxohexanoic acid, 2-Ketohexanoic acid, 3-keto-n-caproic acid, (R)-3-methyl-2-oxo-Pentanoic acid, 2-Oxohexanoic acid; 2-Oxohexanoate, 2-Methyl-3-ketovaleric acid, Adipate semialdehyde, Hexan-1-one-6-carboxylate; 6-Oxohexanoate, Ketoleucine, 2-oxo-3-methylvaleric acid, 5-Oxohexanoic acid, 5-Oxohexanoate, 4-Acetylbutyric acid, 3-Methyl-2-oxovaleric acid, 6-Hydroxyhexan-6-olide, 6-Hydroxy-6-hexanolactone, 1-Oxa-2-oxo-3-hydroxycycloheptane, 5-keto-n-caproic acid, 3-oxo-4-methyl-pentanoic acid, 4-keto-n-caproic acid, Ethyl 3-oxobutanoate, Ethyl acetoacetate, Mevalonolactone, 2oxo-3R-methyl-pentanoic acid, (R)-Pantolactone, (R)-Pantoyl lactone, (3R)-Dihydro-3-hydroxy-4,4-di methyl-2(3H)-Furanone, and 2-oxoisocaproic acid.

C8neg_M117T127: Butanone, Butanal, Tetrahydrofuran, beta-hydroxybutyrate, 2-Hydroxyvaleric acid, b-Hydroxyisovaleric acid, 3-Hydroxy-2-methyl-[R-(R,R)]-butanoic acid, 3-Hydroxy-2-methyl-[R-(R,S)]-butanoic acid, DL-a-Hydroxyvaleric acid, L-alpha-Hydroxyisovaleric acid, (S)-2-Ethyl-3-hydroxypropionic acid, a-hydroxyisovalerate, 2-Ethylhydracrylic acid, 2-Methyl-3-hydroxybutyric, acid 4-hydroxy-valeric acid, 5-Hydroxypentanoate, and 5-hydroxy valeric acid.

HILICneg_M117T61: Tetrahydrofuran, Butanone, Butanal, 5-hydroxy valeric acid, 5-Hydroxypentanoate, 2-Methyl-3-hydroxybutyric acid, 2-Ethylhydracrylic acid, 2-Hydroxyvaleric acid, DL-a-Hydroxyvaleric acid, L-alpha-Hydroxyisovaleric acid, 4-hydroxy-valeric acid, b-Hydroxyisovaleric acid, beta-hydroxybutyrate, 3-Hydroxy-2- methyl-[R-(R,S)]-butanoic acid, a-hydroxyisovalerate, 3-Hydroxy-2-methyl-[R-(R,R)]-butanoic acid, and (S)-2-Ethyl-3-hydroxypropionic acid.

HILICneg_M117T67: Pyruvaldehyde, Acrylic acid, Malondialdehyde, Propenoate, Acrylic acid, Acrylate, 2-Propenoic acid, Vinylformic acid, Erythrono-1,4-lactone, Methyl oxalate, Methylmalonic acid, 2(3H)-Furanone, dihydro-3,4-dihydroxy, Threonolactone, and Succinic acid.

Figure 6:
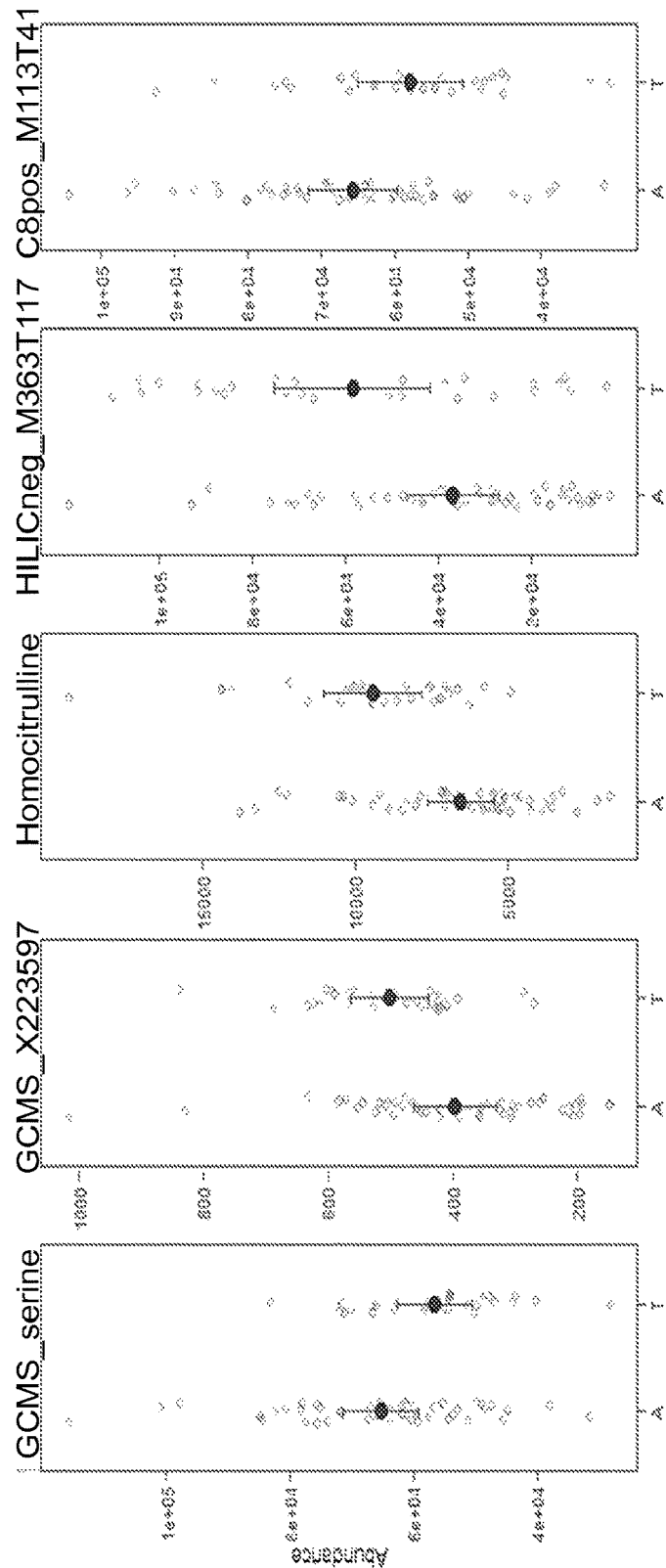
FIG. 6. Abundance in autistic (A) and typical (T) subjects of the five biometabolic features in common between HFA, LFA, and Aut populations.

FIG. 6 shows the abundance in both autistic (A) and typical (T) subjects of the five biometabolic features in common between HFA, LFA, and Aut populations for use in diagnosis of autism.

Figure 7:
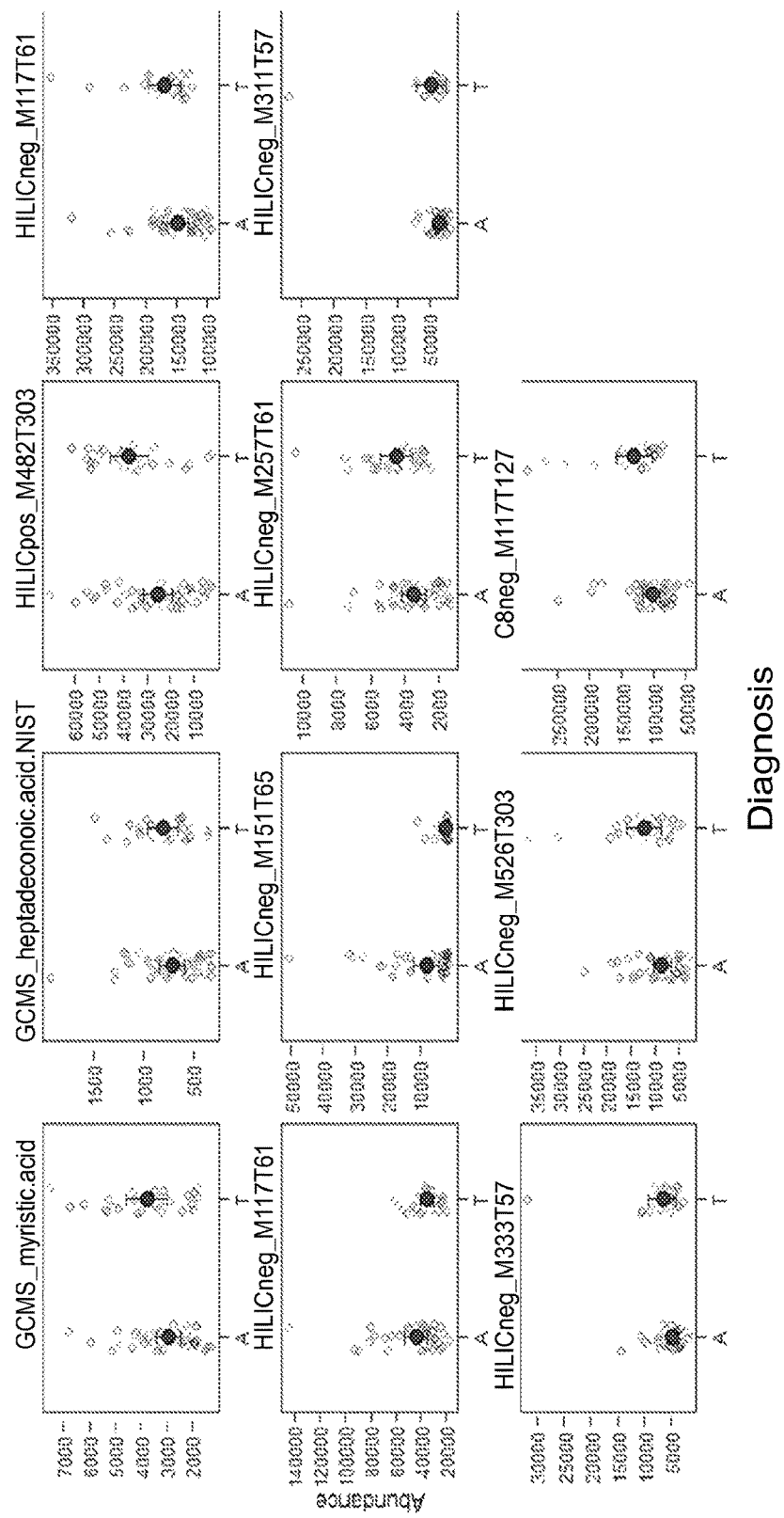
FIG. 7. Abundance in autistic (A) and typical (T) subjects of eleven of the thirty-nine biometabolic features in common between LFA and Aut populations.

FIG. 7 shows the abundance in autistic (A) and typical (T) subjects of eleven of the thirty-nine biometabolic features in common between LFA and Aut populations for use in diagnosis of autism.

Figure 8:
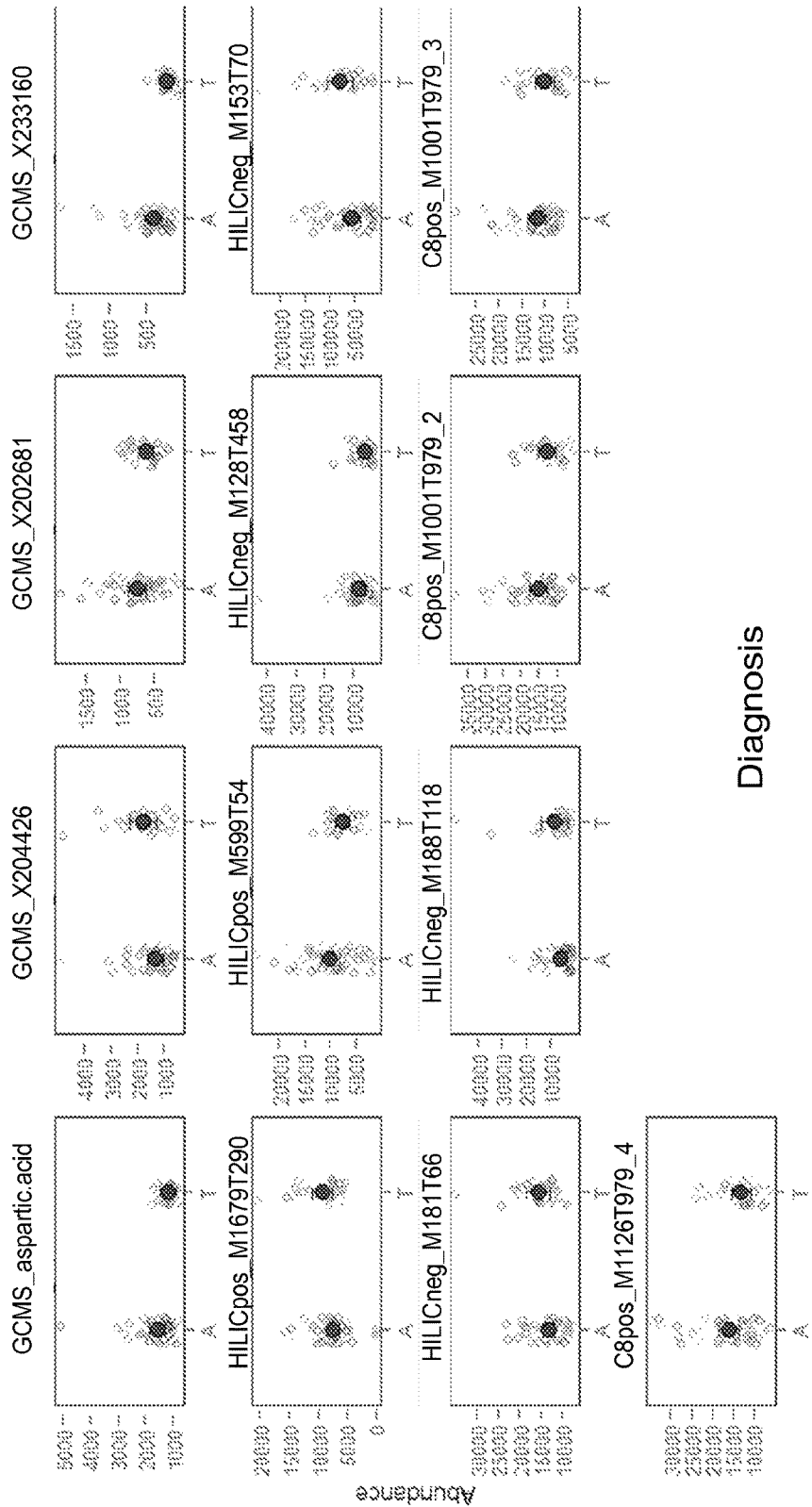
FIG. 8. Abundance in autistic (A) and typical (T) subjects of the thirteen biometabolic features in common between HFA and Aut populations.
Figure 9:
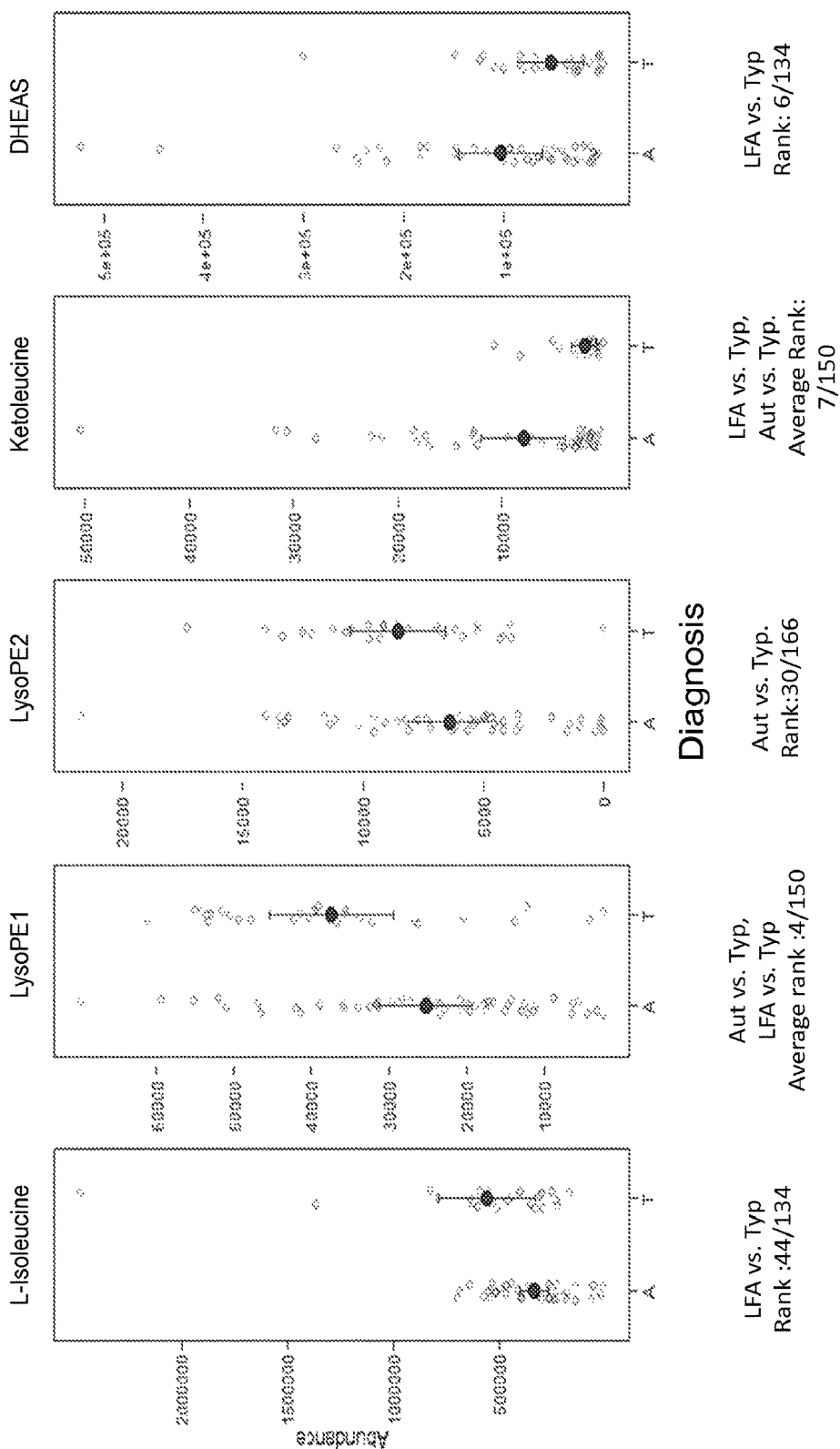
FIG. 9. Abundance of additional biometabolic features in High Functioning Autism (HFA), Low Functioning Autism (LFA), Autism (Aut), and typical populations.
Figure 10:
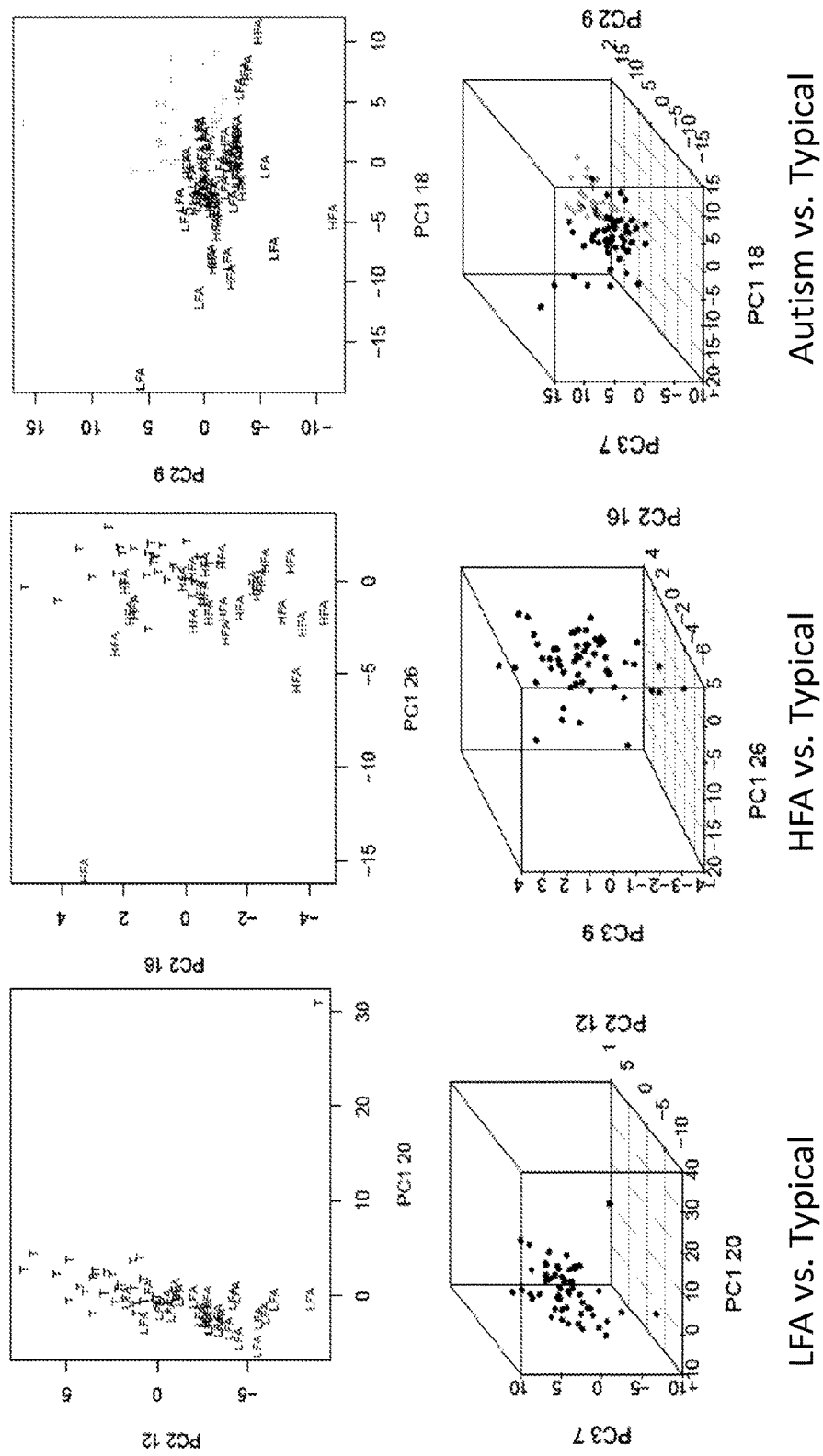
FIG. 10. Combined features from all analytical methods.
Figure 11:
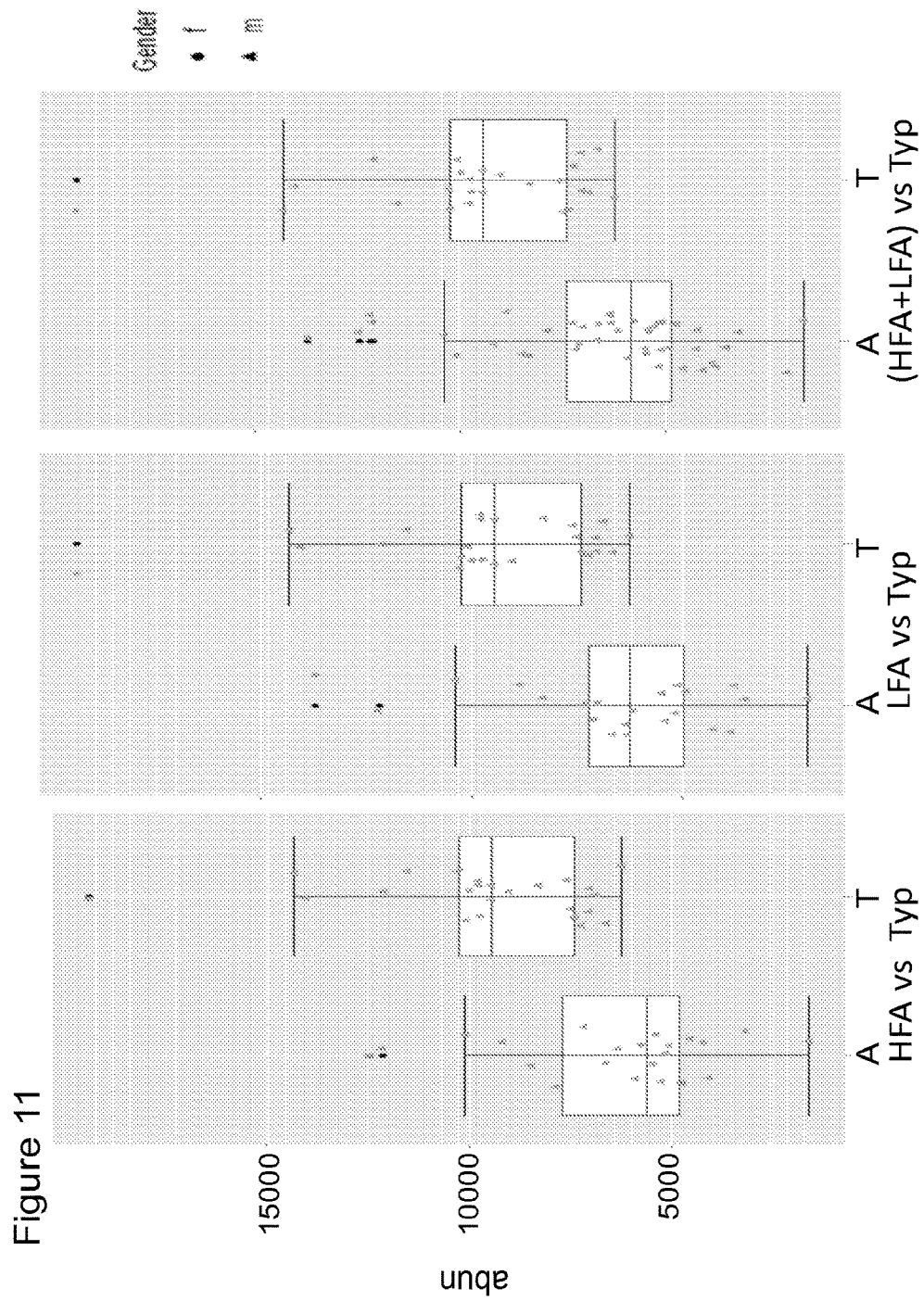
FIG. 11. The HILIC(+) distribution for feature M190T512 (homocitrulline) in High Functioning Autism (HFA) versus typical developing (Typ) populations, Low Functioning Autism (LFA) versus Typ populations, and LFA+LFA versus Typ populations.
Figure 12:
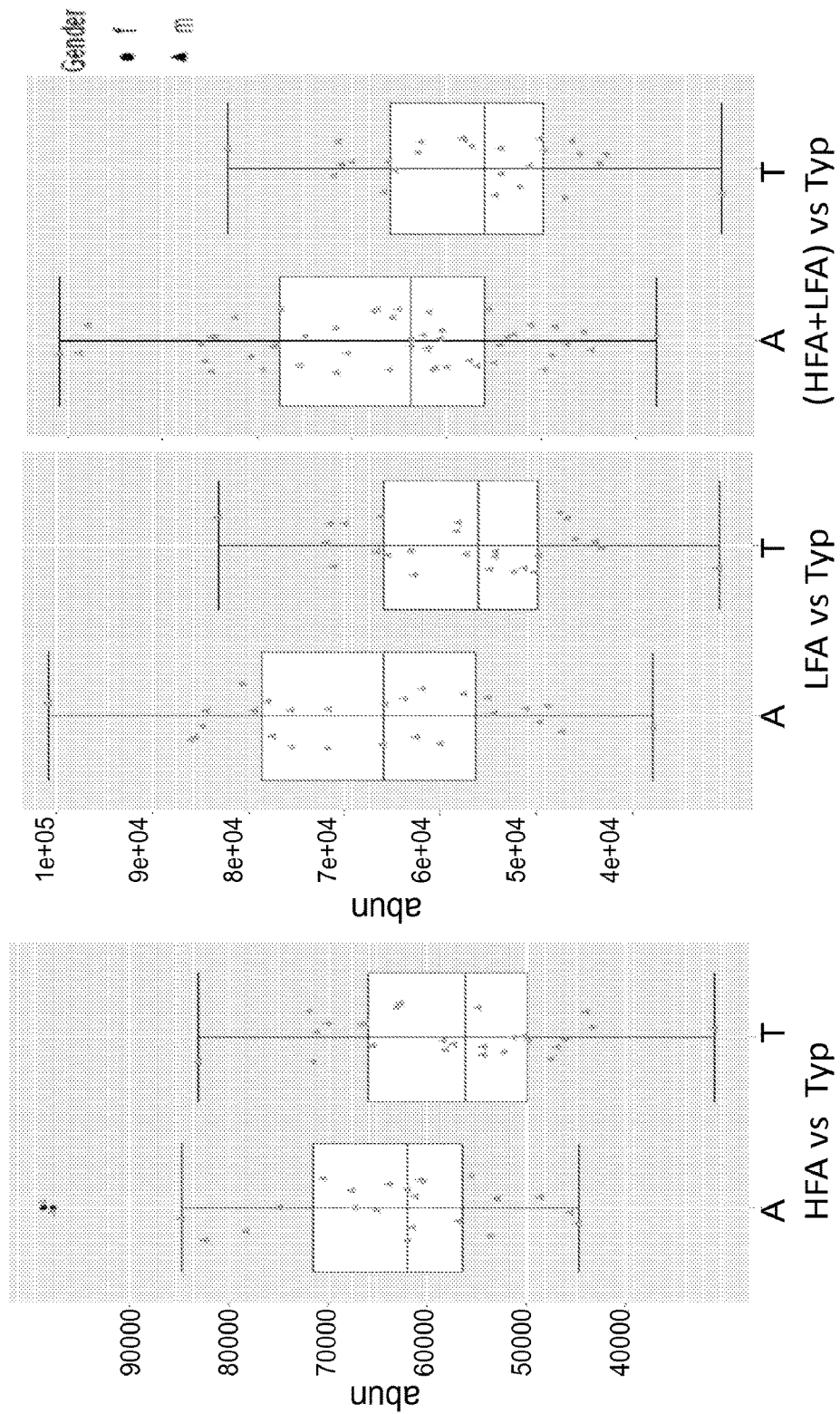
FIG. 12. The GCMS distribution for feature S123 in in High Functioning Autism (HFA) versus typical developing (Typ) populations, Low Functioning Autism (LFA) versus Typ populations, and LFA+LFA versus Typ populations.

FIG. 8 shows the abundance in autistic (A) and typical (T) subjects of the thirteen biometabolic features in common between HFA and Aut populations for use in diagnosis of autism. FIG. 9 shows the abundance of additional biometabolic features in High Functioning Autism (HFA), Low Functioning Autism (LFA), Autism (Aut), and typical populations. And, FIG. 10 shows combined features from all analytical methods. FIG. 11 shows the distribution for citrulline (the HILIC(+) feature M190T512) in HFA versus typical populations, LFA versus typical populations, and LFA+LFA versus typical populations. FIG. 12 shows the GCMS distribution for feature S123 in HFA versus typical populations, LFA versus typical populations, and LFA+LFA versus typical populations.

The increase in classification accuracy observed in LFA versus TD which was 16% greater the HFA versus TD model suggests that more severe forms of the disorder have a marked impact on metabolism. The overall classification accuracy is a global measure of the model's performance toward accurate diagnoses. Sensitivity is the percentage of individuals correctly classified as diagnosed with ASD and higher values indicate the probability that an individual with ASD will be correctly diagnosed, leading to fewer false negative diagnosis. The measure of specificity indicates the probability that a typical individual will be correctly classified as typical and not as having ASD. Putative annotation of the mass features shows a broad variety of metabolites are represented in the models including fatty acids, phospholipids, amino acids, intermediary, and others. For example, isoleucine was observed at significantly lower levels in the ASD patients, showing an average abundance ratio of 0.55 for LFA/TD and 0.70 for HFA/TD. This is consistent with the identification of a point mutation in a gene encoding the branched-chain amino acid dehydrogenase kinase (BCKDK), which causes degradation and depletion of the branched chain amino acids leucine, isoleucine and valine, leading to a form of autism with epilepsy (Novarino et al., 2012, *Science;* 338:394-397).

This example has identified a metabolic signature in blood plasma able to classify high and/or low functioning autistic individuals from typical individuals through a comprehensive metabolomic analysis.

Additional blood samples from 295 additional patients obtained as part of the Autism Phenome Project (APP) will be evaluated (⅔ are diagnosed with ASD and the remaining third are typically developing children). These samples are from children aged 2 to 3.5 years. Evaluating patient samples from these younger children will allow the identification of biomarkers which will diagnose patients at an earlier age providing potentially greater impact on patient outcomes. The APP is a longitudinal study, plasma samples have been collected from these children when they reached 5 years of age. These samples will provide a valuable resource for future studies to investigate the stability of metabolomics signatures of ASD over early childhood. Inclusion criteria for APP subjects are ambulatory, no suspected vision or hearing problems, motor milestones not significantly delayed, and body weight greater than 20 pounds. Exclusion criteria included presence of a fragile health condition preventing valid participation in the assessment, any family disorders or diseases that might complicate the comparison group (for example, a parent with bipolar disease, cousin or sibling with autism), and typically developing children with abnormal MSEL scores.

Example 4

Additional Cohorts

This example will continue the work of the previous examples, which successfully discovered 179 metabolites (or groups of metabolites) in blood that can identify patients with ASD with over 80% accuracy. Biomarkers that can be measured in the blood of patients may allow a metabolic understanding of the disorder and earlier diagnosis than behavioral analysis which is the primary method of diagnosis today. This example will directly measure hundreds to thousands of metabolites in the plasma of individuals with ASD and compare these measurements to those obtained from non-autistic individuals of a similar age. A non-targeted metabolomic analysis approach will be used to study banked blood samples from a very well characterized set of samples at the MIND Institute at UC-Davis. Ultimately, this example will inform whether abnormal levels of some metabolites are present in the plasma of individuals with ASD compared to typical patients. The metabolites will be identified and will be mapped to metabolic pathways that will simultaneously help develop a better understanding of the mechanisms of ASD and provide potential targets for future therapeutic development. Ultimately, the identified metabolites can be transferred to other types of platforms such as a clinical diagnostic kit.

As shown in the previous examples, samples from these cohorts demonstrated that combinations of metabolites found in plasma samples form signatures which can identify individuals with ASD. With this example additional samples from several cohorts of well-characterized subjects with ASD and age-matched typically developing control children will be assayed.

The complete disclosure of all patents, patent applications, and publications, and electronically available material (including, for instance, nucleotide sequence submissions in, e.g., GenBank and RefSeq, and amino acid sequence submissions in. e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. All headings are for the convenience of the reader and should not be used to limit the meaning of the text that follows the heading, unless so specified.

What is claimed is:

1. A method comprising:
   assaying a biosample from a subject for a plurality of small molecule metabolites by mass spectrometry; and
   quantifying the amount of 2-aminooctanoic acid, acesulfame, asymmetric dimethylarginine (ADMA), choline, 3-carboxy-4-methyl-5-propyl-2-furanpropanoic acid (CMPF), cysteine, cystine, dehydroepiandrosterone sulfate (DHEAS), glycine, glycocholic acid, hypoxanthine, indoleacrylic acid, indoxyl sulfate, LysoPC(16:1(9Z)), LysoPE(0:0/18:1(9Z)), LysoPE(22:6(4Z,7Z,10Z,13Z,16Z,19Z)/0:0), LysoPE(22:6(4Z,7Z,10Z,13Z,16Z,19Z)/0:0), methionine, p-cresol sulfate, phenylalanine, phenyllactic acid, proline, serotonin, tryptophan, uric acid, and valine in the biosample.

2. The method of claim 1, wherein mass spectrometry comprises gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg).

3. The method of claim 1, wherein the subject is less than two years of age.

4. The method of claim 1, wherein the biosample is plasma.

5. A method comprising:
   assaying a biosample from a subject for a plurality of small molecule metabolites by mass spectrometry; and
   quantifying the amount of homocitrulline, 2-hydroxyvaleric acid, cystine, aspartic acid, isoleucine, creatinine, serine, 4-hydroxyphenyllactic acid, citric acid, glutamic acid, lactic acid, dehydroepiandrosterone sulfate (DHEAS), glutaric acid, 5-hydroxynorvaline, heptadecanoic acid, 5-aminovaleric acid lactam, succinic acid, myristic acid, 2-hydroxyvaleric acid, methylhexadecanoic acid, and 3-aminoisobutyric acid in the biosample.

6. The method of claim 5, wherein mass spectrometry comprises gas chromatography mass spectrometry (GCMS), C8 liquid chromatography coupled to electrospray ionization in positive ion polarity (C8pos), C8 liquid chromatography coupled to electrospray ionization in negative ion polarity (C8neg), hydrophilic interaction liquid chromatography coupled to electrospray ionization in positive ion polarity (HILICpos), and/or hydrophilic interaction liquid chromatography coupled to electrospray ionization in negative ion polarity (HILICneg).

7. The method of claim 5, wherein the subject is less than two years of age.

8. The method of claim 5, wherein the biosample is plasma.

* * * * *